United States Patent
Hopkins

(10) Patent No.: US 11,167,085 B2
(45) Date of Patent: Nov. 9, 2021

(54) SYRINGE SYSTEMS AND METHODS FOR MULTI-STAGE FLUID DELIVERY

(71) Applicant: TRUE CONCEPTS MEDICAL TECHNOLOGIES, LLC, Springboro, OH (US)

(72) Inventor: Michael Hopkins, Springboro, OH (US)

(73) Assignee: TRUE CONCEPTS MEDICAL TECHNOLOGIES, LLC, Springboro, OH (US)

( * ) Notice: Subject to any disclaimer, the term of this patent is extended or adjusted under 35 U.S.C. 154(b) by 77 days.

(21) Appl. No.: 15/984,257

(22) Filed: May 18, 2018

(65) Prior Publication Data

US 2018/0264195 A1    Sep. 20, 2018

Related U.S. Application Data

(63) Continuation-in-part of application No. 15/949,607, filed on Apr. 10, 2018, now Pat. No. 11,116,904.
(Continued)

(51) Int. Cl.
| | |
|---|---|
| *A61M 5/19* | (2006.01) |
| *A61M 5/315* | (2006.01) |
| *A61M 5/32* | (2006.01) |
| *A61M 5/31* | (2006.01) |
| *A61M 5/178* | (2006.01) |

(52) U.S. Cl.
CPC .......... *A61M 5/19* (2013.01); *A61M 5/31513* (2013.01); *A61M 5/31596* (2013.01); *A61M 5/32* (2013.01); *A61M 2005/1787* (2013.01); *A61M 2005/3128* (2013.01); *A61M 2202/04* (2013.01)

(58) Field of Classification Search
CPC .. A61M 5/19; A61M 5/31596; A61M 5/3243; A61M 5/32; A61M 2005/1787; A61M 2005/3128; A61M 2202/04
See application file for complete search history.

(56) References Cited

U.S. PATENT DOCUMENTS

| | | |
|---|---|---|
| 3,739,947 A | 6/1973 | Baumann et al. |
| 4,340,068 A | 7/1982 | Kaufman |

(Continued)

FOREIGN PATENT DOCUMENTS

WO    2013112579 A1    8/2013

OTHER PUBLICATIONS

Stephen Sheehan, Sagent Pharmaceutical's Sequential Syringes, Medgadget (Sep. 29, 2008), https://www.medgadget.com/2008/09/sagent_pharmaceuticals_sequential_syringes_1.html.

(Continued)

*Primary Examiner* — Rebecca E Eisenberg
*Assistant Examiner* — John A Doubrava
(74) *Attorney, Agent, or Firm* — Ulmer & Berne LLP

(57) ABSTRACT

Embodiments include a syringe-based apparatus for delivering fluid, the apparatus comprising a housing having an open proximal end and a distal end defining an inner volume, a needle, an actuator mechanism coupled with the housing, the actuator mechanism comprising a syringe body and a plunger, a medicament reservoir, and a reconstitution fluid reservoir.

18 Claims, 47 Drawing Sheets

Related U.S. Application Data which is a continuation of application No. 15/624,593, filed on Jun. 15, 2017, now Pat. No. 9,962,489.

(60) Provisional application No. 62/350,341, filed on Jun. 15, 2016.

(56) References Cited

U.S. PATENT DOCUMENTS

| | | |
|---|---|---|
| 4,512,768 A | 4/1985 | Rangaswamy |
| 4,832,682 A | 5/1989 | Sarnoff |
| 5,053,019 A | 10/1991 | Duffy |
| 5,181,909 A | 1/1993 | McFarlane |
| 5,232,439 A | 8/1993 | Campbell et al. |
| 5,342,313 A | 8/1994 | Campbell et al. |
| 5,411,482 A | 5/1995 | Campbell |
| 5,423,759 A | 6/1995 | Campbell |
| 5,472,420 A | 12/1995 | Campbell |
| 5,545,143 A | 8/1996 | Fischell |
| 6,017,328 A | 1/2000 | Fischell et al. |
| 6,074,371 A | 6/2000 | Fischell |
| 6,768,811 B2 | 7/2004 | Dinstein et al. |
| 6,997,910 B2 | 2/2006 | Howlett et al. |
| 7,018,089 B2 | 3/2006 | Wenz et al. |
| 7,048,720 B1 | 5/2006 | Thorne, Jr. et al. |
| 7,101,354 B2 | 9/2006 | Thorne, Jr. et al. |
| 7,367,358 B2 | 5/2008 | Malcolm |
| 7,896,017 B2 | 3/2011 | Malcolm |
| 7,998,106 B2 | 8/2011 | Thorne, Jr. et al. |
| 8,038,656 B2 | 10/2011 | Lloyd et al. |
| 8,043,864 B2 | 10/2011 | Stroup |
| 8,119,419 B2 | 2/2012 | Stroup |
| 8,197,420 B2 | 6/2012 | Patton |
| 8,231,546 B2 | 7/2012 | Patton |
| 8,337,418 B2 | 12/2012 | Patton |
| 8,491,537 B2 | 7/2013 | Kosinski et al. |
| 8,535,241 B2 | 9/2013 | Bullington et al. |
| 8,647,286 B2 | 2/2014 | Patton |
| 8,864,684 B2 | 10/2014 | Bullington et al. |
| 8,876,734 B2 | 11/2014 | Patton |
| 9,022,950 B2 | 5/2015 | Bullington et al. |
| 9,022,951 B2 | 5/2015 | Bullington et al. |
| D731,643 S | 6/2015 | Bullington et al. |
| 9,060,724 B2 | 6/2015 | Bullington et al. |
| 9,060,725 B2 | 6/2015 | Bullington et al. |
| 9,149,576 B2 | 10/2015 | Bullington et al. |
| 9,155,495 B2 | 10/2015 | Bullington et al. |
| 9,204,864 B2 | 12/2015 | Bullington et al. |
| 9,694,134 B2 | 7/2017 | Bradley et al. |
| D794,779 S | 8/2017 | Bullington et al. |
| 9,718,080 B1 | 8/2017 | Gonzalez et al. |
| 9,788,774 B2 | 10/2017 | Bullington et al. |
| 9,788,775 B2 | 10/2017 | Bullington et al. |
| 9,855,001 B2 | 1/2018 | Patton |
| 9,855,002 B2 | 1/2018 | Patton |
| 9,861,306 B2 | 1/2018 | Patton |
| 9,872,645 B2 | 1/2018 | Patton |
| 9,931,466 B2 | 4/2018 | Bullington et al. |
| 9,950,084 B2 | 4/2018 | Bullington et al. |
| 9,962,489 B2 | 5/2018 | Hopkins |
| 9,999,383 B2 | 6/2018 | Bullington et al. |
| 10,028,687 B2 | 7/2018 | Patton |
| 10,028,688 B2 | 7/2018 | Patton |
| 10,028,689 B2 | 7/2018 | Patton |
| 10,039,483 B2 | 8/2018 | Bullington et al. |
| 10,045,724 B2 | 8/2018 | Patton |
| 10,047,209 B2 | 8/2018 | Yorde et al. |
| 10,052,053 B2 | 8/2018 | Patton |
| 10,123,783 B2 | 11/2018 | Bullington et al. |
| D841,151 S | 2/2019 | Bullington et al. |
| 10,194,853 B2 | 2/2019 | Bullington et al. |
| 10,206,613 B2 | 2/2019 | Bullington et al. |
| 10,220,139 B2 | 3/2019 | Bullington et al. |
| 10,251,590 B2 | 4/2019 | Bullington et al. |
| 2004/0122359 A1 | 6/2004 | Wenz et al. |
| 2004/0171984 A1 | 9/2004 | Greenfield |
| 2006/0052747 A1* | 3/2006 | Nishimura ......... A61M 5/31596 604/85 |
| 2007/0073267 A1 | 3/2007 | Muller |
| 2008/0082055 A1 | 4/2008 | Lloyd et al. |
| 2010/0241067 A1* | 9/2010 | Magrini ............ A61M 5/31596 604/82 |
| 2010/0286513 A1 | 11/2010 | Pollard, Jr. et al. |
| 2010/0286609 A1 | 11/2010 | Mahurkar |
| 2011/0009830 A1 | 1/2011 | Kosinski et al. |
| 2012/0016313 A1 | 1/2012 | Nalesso et al. |
| 2012/0220950 A1 | 8/2012 | Carlyon |
| 2013/0274716 A1 | 10/2013 | Nelson et al. |
| 2014/0074062 A1 | 3/2014 | Caffey et al. |
| 2014/0163419 A1 | 6/2014 | Bullington et al. |
| 2015/0025454 A1* | 1/2015 | Wetzel .............. A61M 5/31501 604/91 |
| 2016/0106584 A1* | 4/2016 | Andino ................. A61M 5/19 604/87 |
| 2018/0056022 A1* | 3/2018 | Liu ................. A61M 15/0035 |
| 2018/0193564 A1* | 7/2018 | Dahmani ............ A61M 5/315 |

OTHER PUBLICATIONS

Thomas, Shane; International Search Report and Written Opinion of the International Searching Authority, issued in International Application No. PCT/2017/037788; dated Sep. 6, 2017; 11 pages.

Thomas, Shane; International Search Report and Written Opinion of the International Searching Authority, issued in International Application No. PCT/2017/037789; dated Sep. 6, 2017; 9 pages.

European Extended Search Report of the European Patent Office, Issued in European Application No. 17814134.7; dated Jan. 23, 2020; 5 pages.

European Extended Search Report of the European Patent Office, Issued in European Application No. 17814139.6; dated Jan. 23, 2020; 6 pages.

* cited by examiner

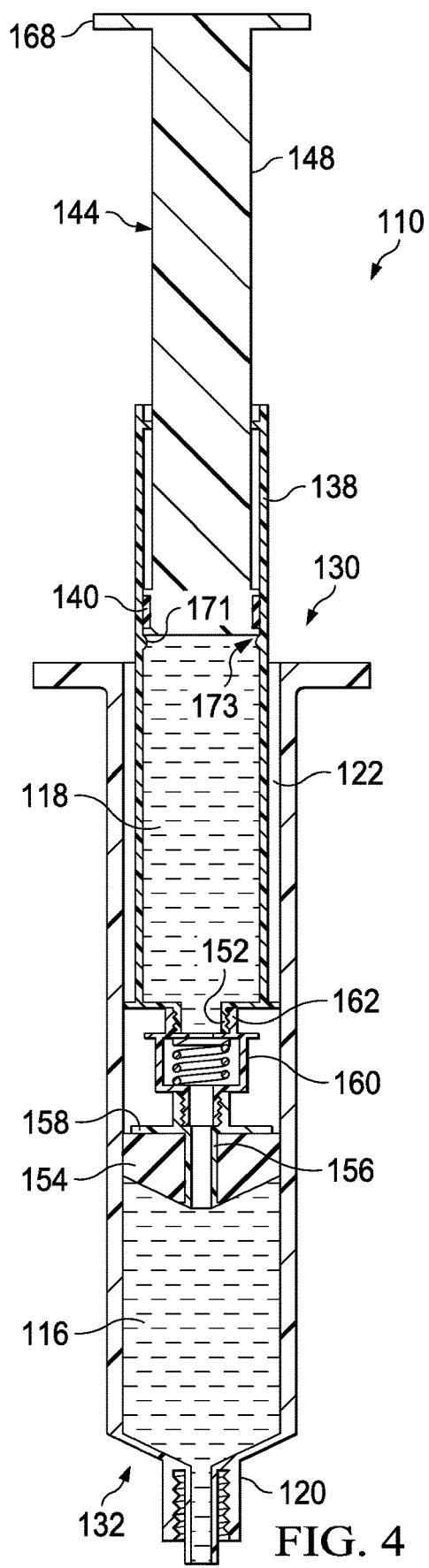
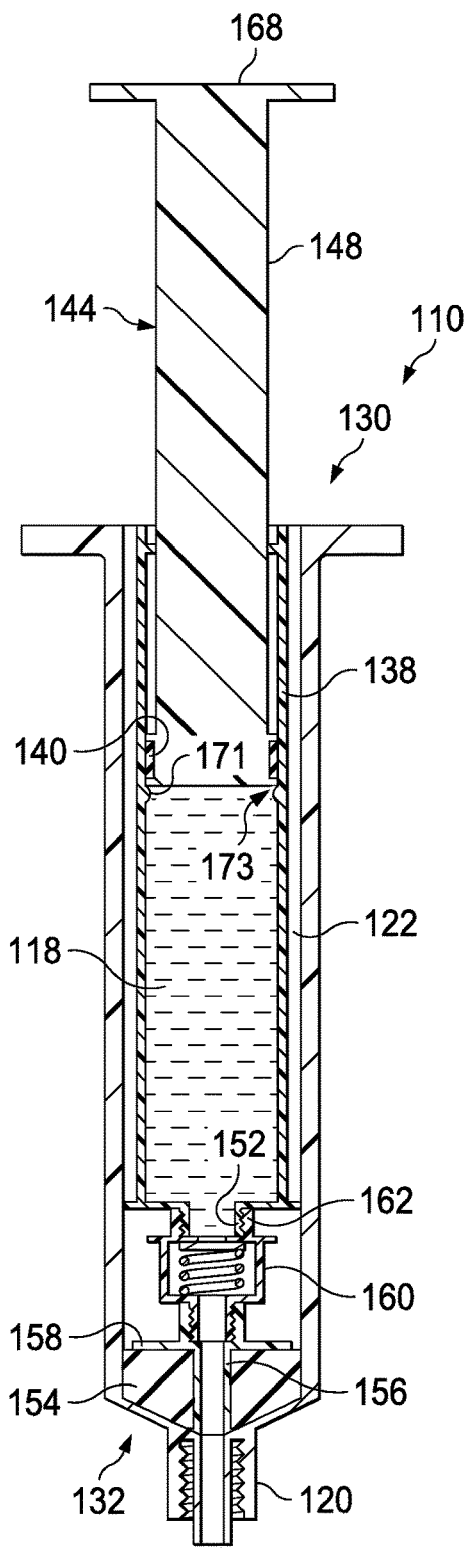
FIG. 4
FIG. 5

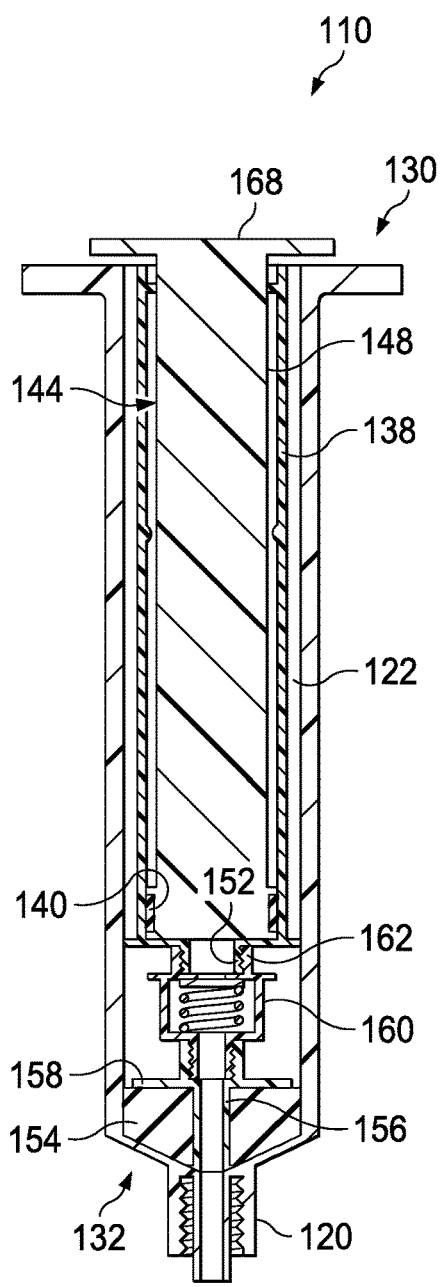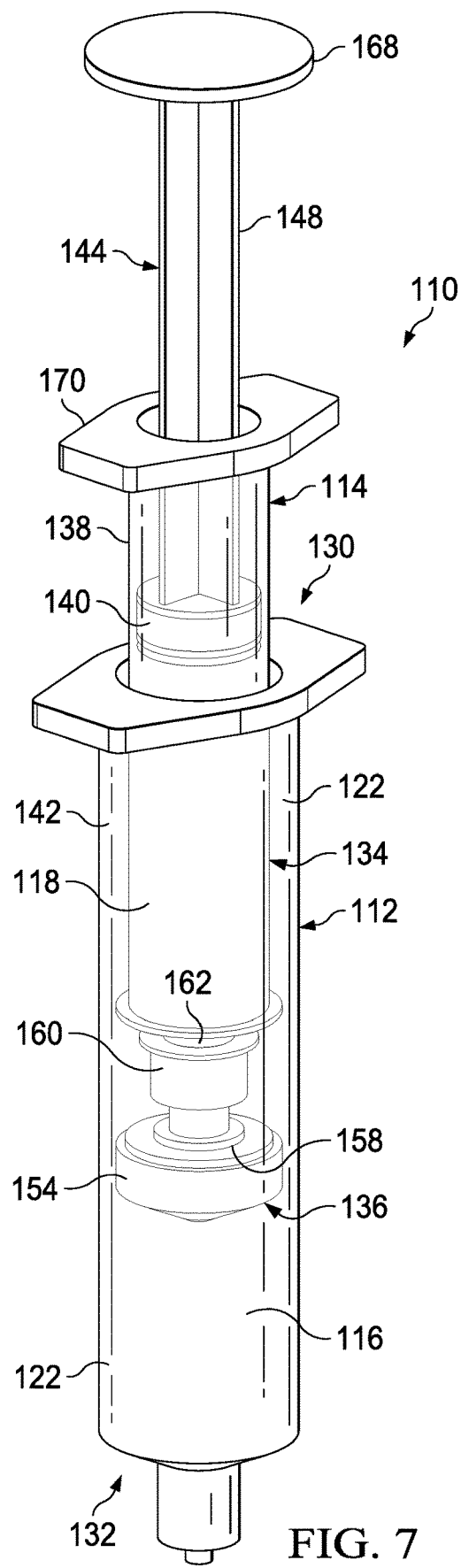
FIG. 6
FIG. 7

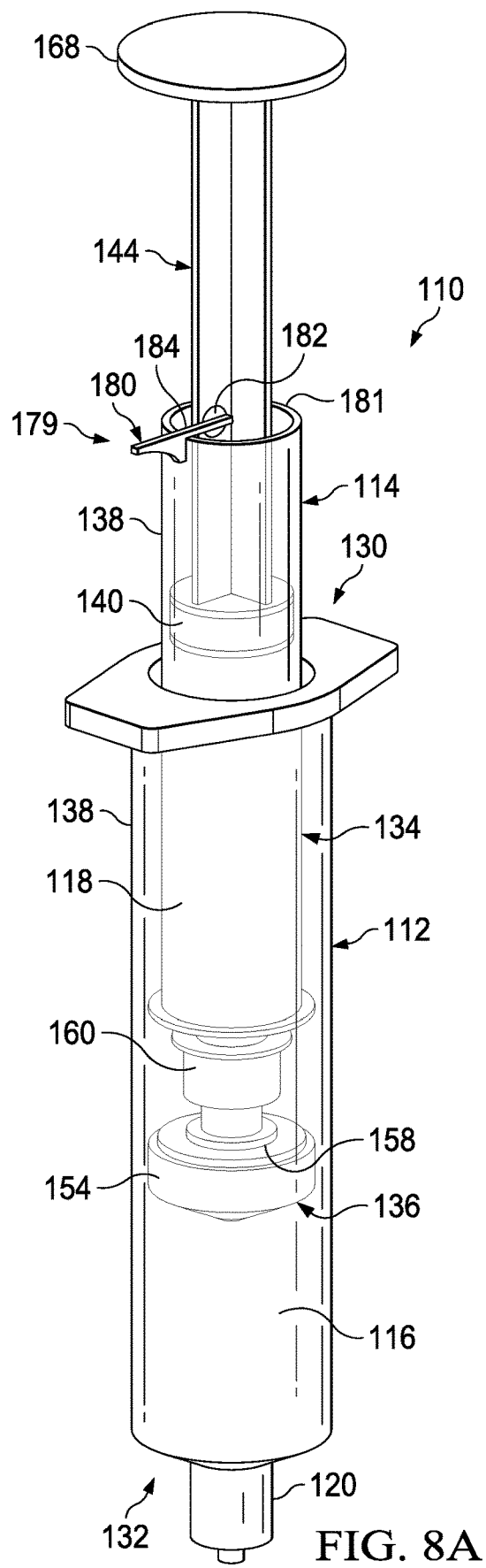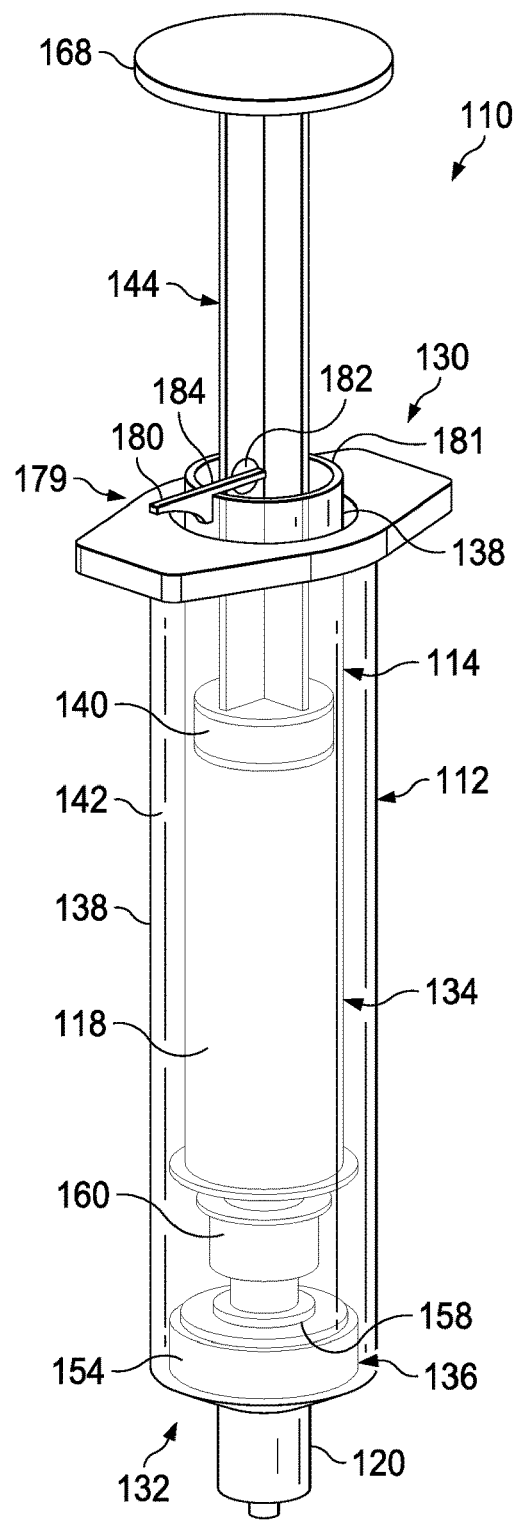
FIG. 8A
FIG. 8B

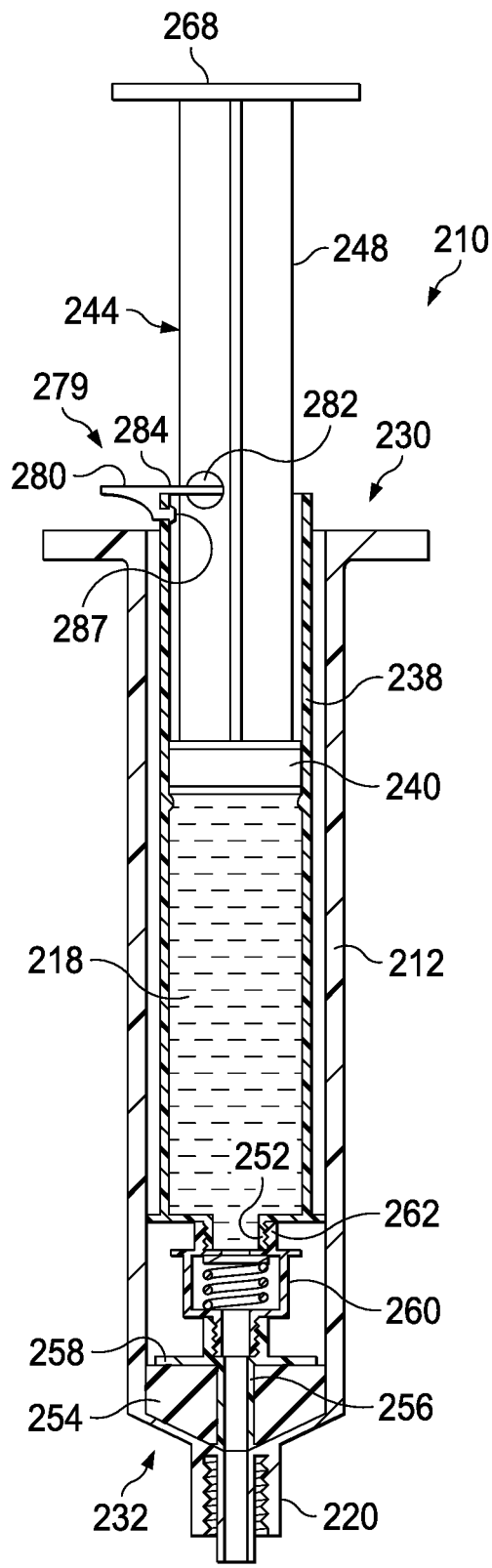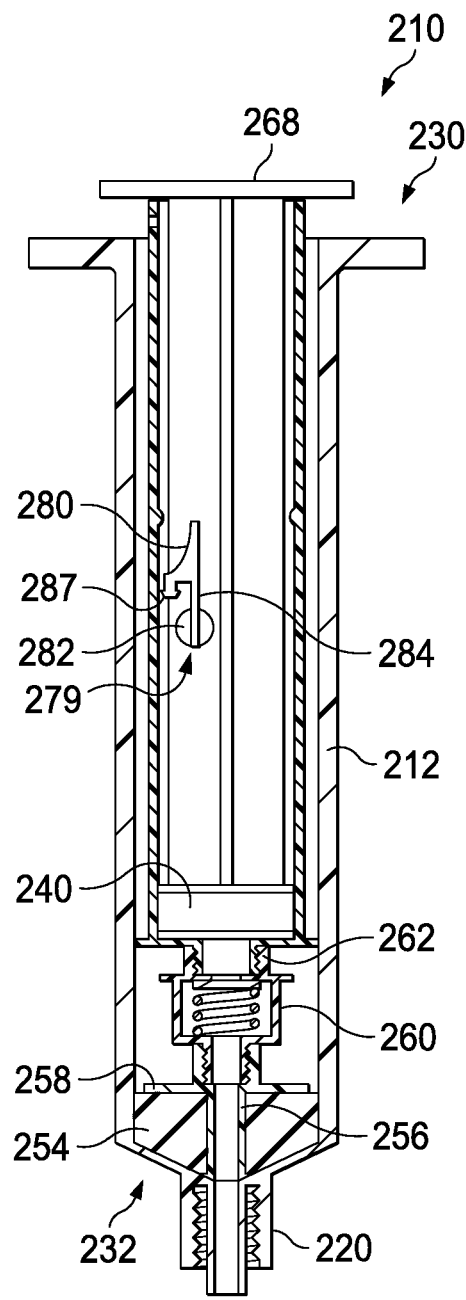
FIG. 15
FIG. 16

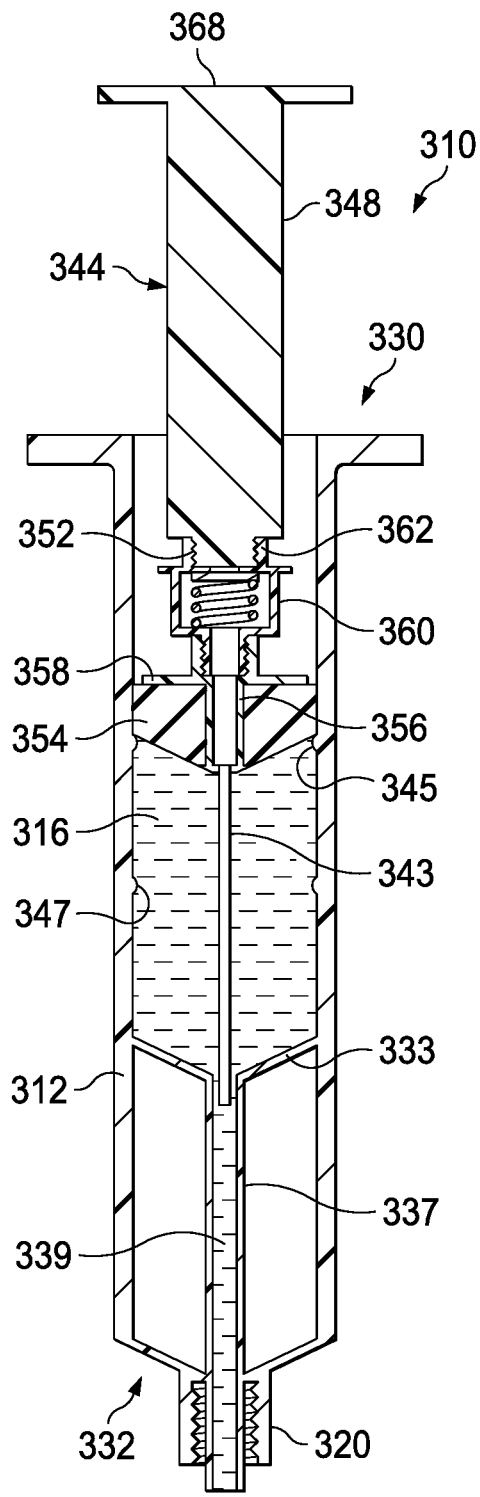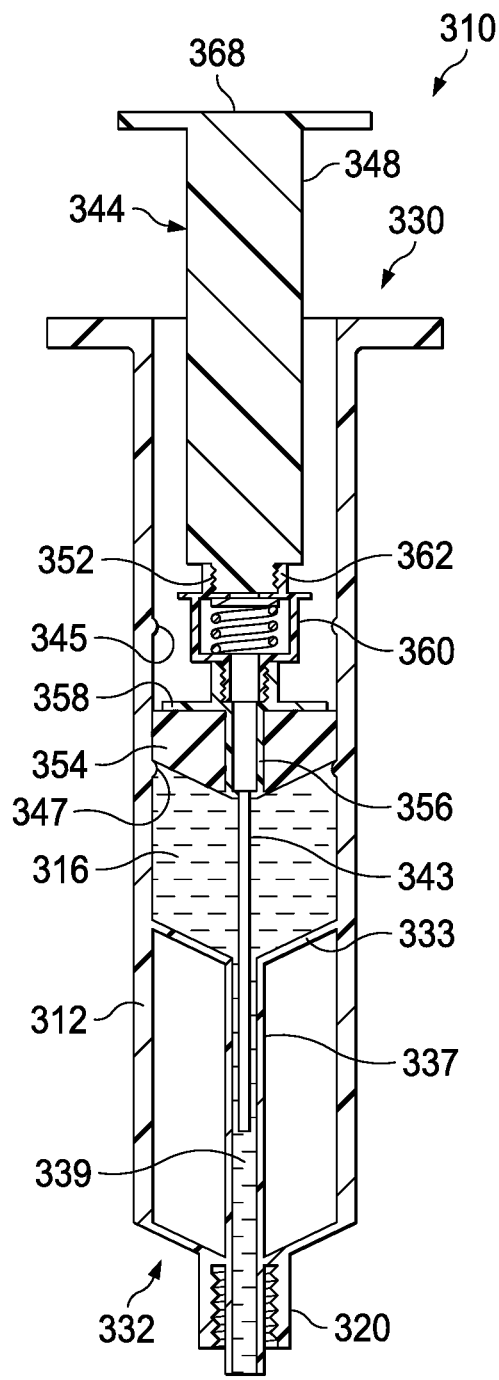
FIG. 19
FIG. 20

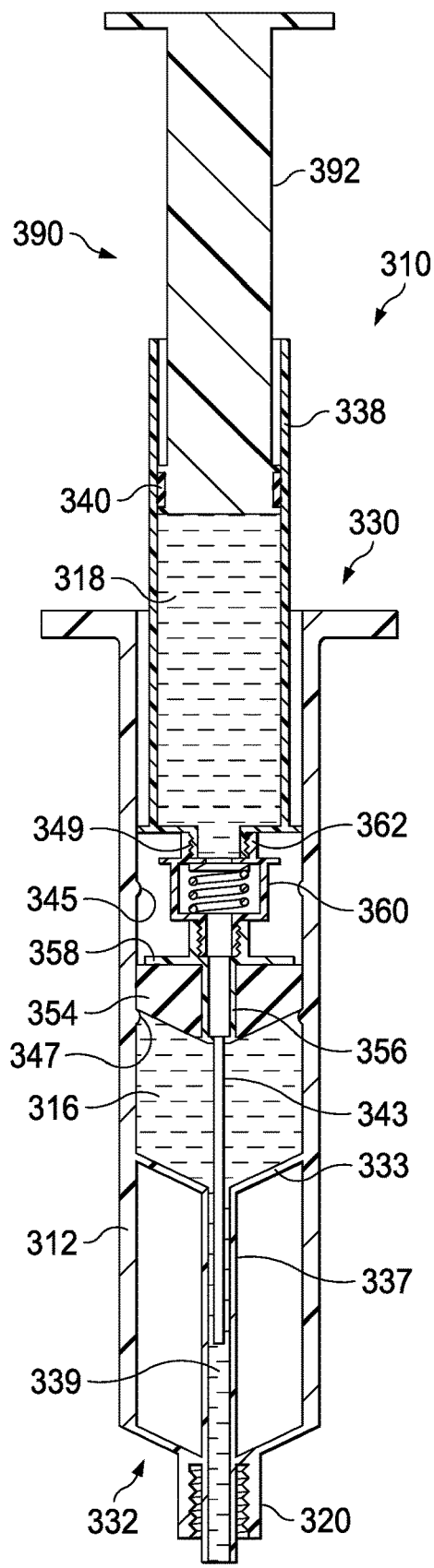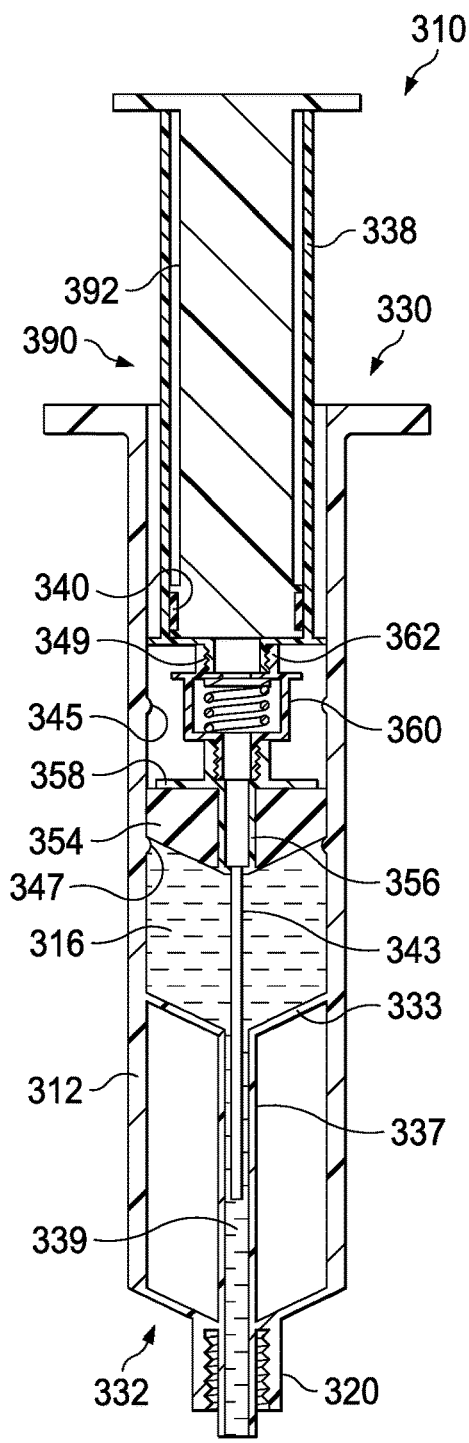
FIG. 21
FIG. 22

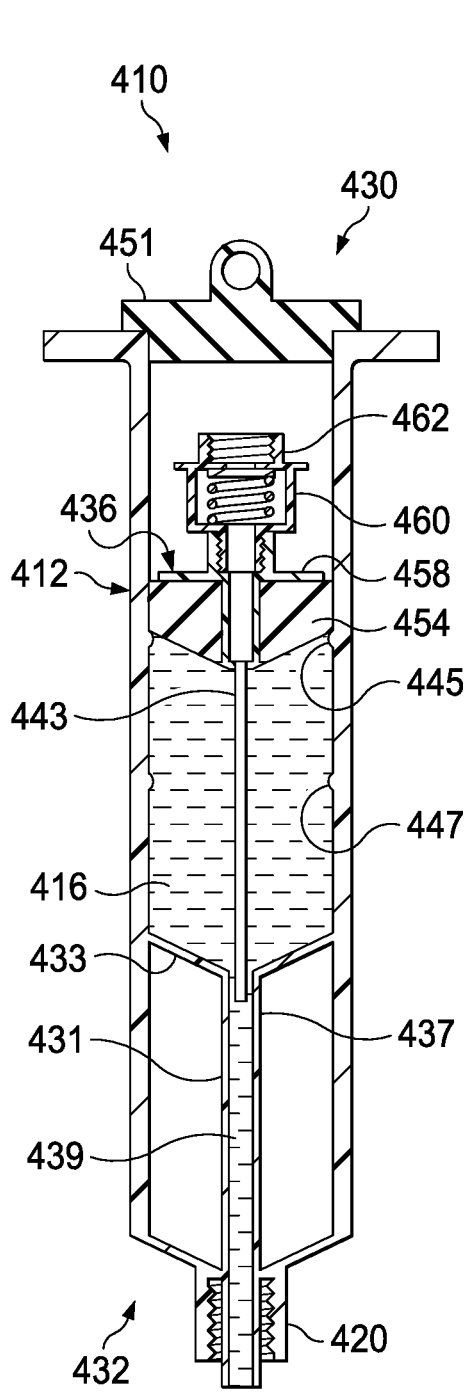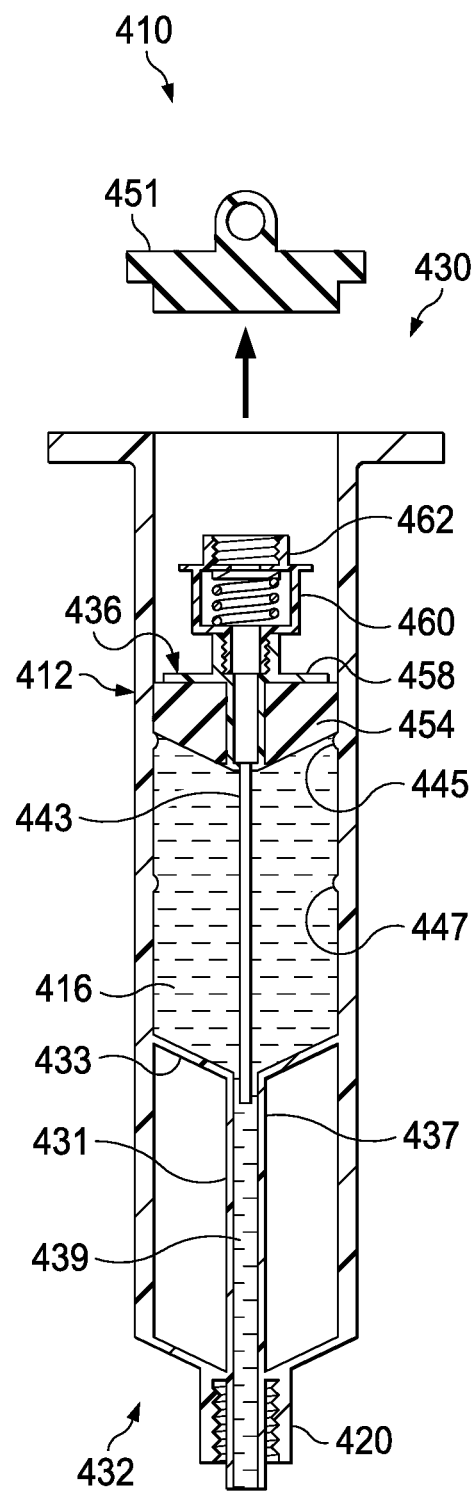
FIG. 26
FIG. 27

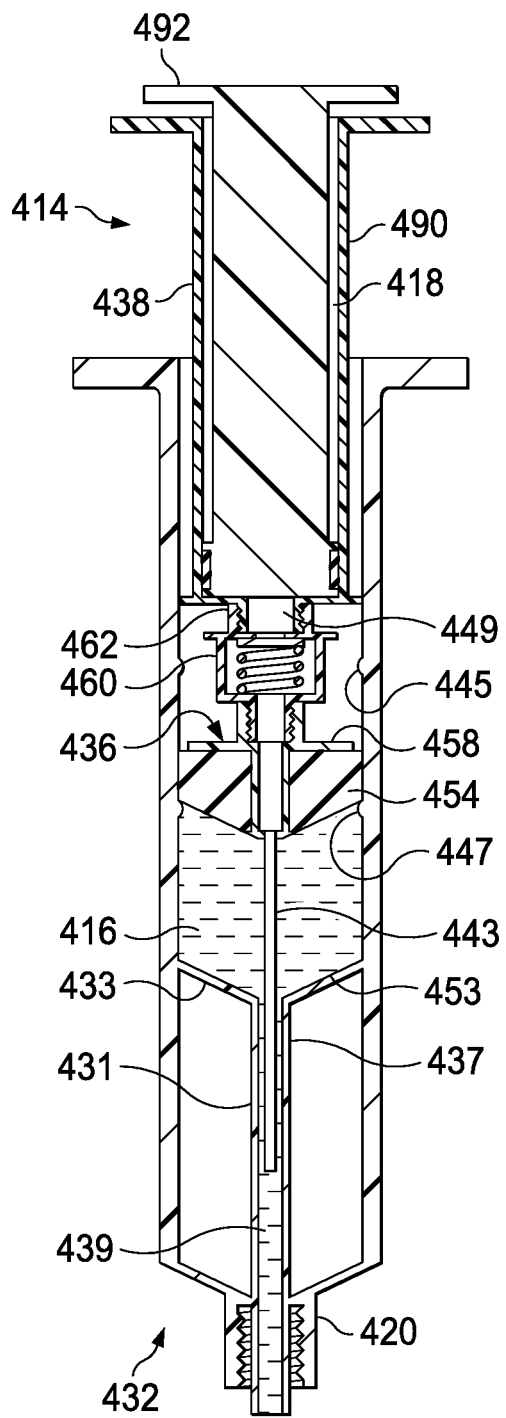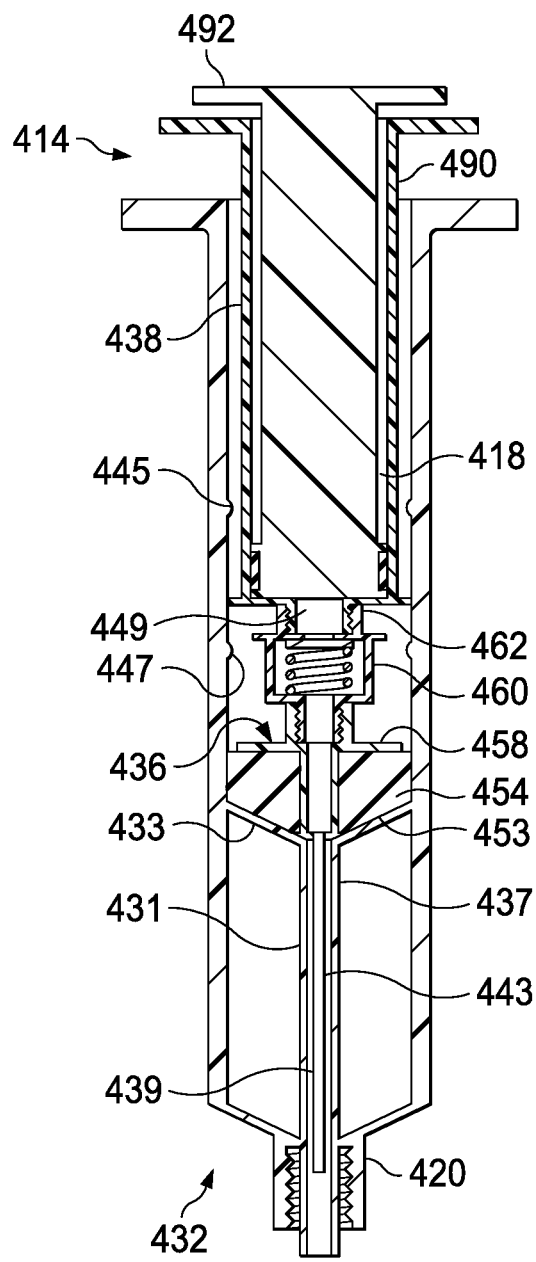
FIG. 30
FIG. 31

SYRINGE SYSTEMS AND METHODS FOR MULTI-STAGE FLUID DELIVERY

REFERENCE TO RELATED APPLICATIONS

This application is a Continuation-in-Part of U.S. Non-Provisional application Ser. No. 15/949,607, filed Apr. 10, 2018, which is a continuation of U.S. Non-Provisional application Ser. No. 15/624,593, filed Jun. 15, 2017, now U.S. Pat. No. 9,962,489 which claims priority to U.S. Provisional Patent Application No. 62/350,341, filed Jun. 15, 2016, which are incorporated by reference herein in their entirety.

TECHNICAL FIELD

Embodiments of the technology relate, in general, to syringe technology, and in particular to syringe systems for the delivery of a medicament followed by the delivery of a saline flush.

BACKGROUND

Supraventricular tachycardia (SVT) is a series of rapid heartbeats that begin in or involve the upper chambers (atria) of the heart. SVT can cause the heart to beat very rapidly or erratically. As a result, the heart may beat inefficiently, and the body may receive an inadequate blood supply. In controlled studies in the United States, bolus doses of 3, 6, 9, and 12 mg of adenosine were studied to determine the effectiveness of the medication on converting SVT to normal sinus rhythm. A cumulative 60% of patients with SVT converted to normal sinus rhythm within one minute after an intravenous bolus dose of 6 mg adenosine, and a cumulative 92% converted after a bolus dose of 12 mg of adenosine. Adenosine slows conduction time through the A-V node, can interrupt the reentry pathways through the A-V node, and can restore normal sinus rhythm in patients with SVT, including SVT associated with Wolff-Parkinson-White Syndrome. Intravenously administered adenosine is rapidly cleared from the circulation via cellular uptake, primarily by erythrocytes and vascular endothelial cells. Adenosine has a half-life of less than 10 seconds in whole blood.

Adenosine injections are generally given as a rapid bolus via a peripheral I.V. route. The bolus dose is then generally followed with a rapid saline flush to facilitate urging the adenosine towards the patient's heart before degrading due to the short half-life. The recommended doses for adults are 6 mg given as a rapid I.V. bolus, administered over a 1-2 second period, followed by a 12 mg bolus dose of adenosine if the first dose does not result in elimination of the SVT in 1-2 minutes. The 12 mg dose can be repeated a second time if required. The recommended neonatal dose is 0.05-0.1 mg/kg, followed by increased doses in 0.05-0.1 mg/kg increments every 1-2 minutes until termination of the SVT. In adults, the bolus adenosine dose is generally followed with a 20 ml saline flush and, for neonatal applications, the dose is generally followed by a 5-10 ml saline flush.

Current systems for delivering first the adenosine dose and then the saline flush include the use of two syringes connected to a T-connector or stopcock. A stopcock is attached to a capped I.V. line with an adenosine syringe on one port and a saline syringe (e.g., 10 ml) on a second open port. The adenosine is then administered over 1-2 seconds, the stopcock is adjusted to access the second syringe, and the saline flush is then delivered to the patient. Such systems can have limitations because of the time needed to transition the T-connector or stopcock from the first syringe to the second syringe. Because the half-life of adenosine is so rapid (i.e., less than 10 seconds), even small amounts of time lost can make a significant difference whether the patient is able to return to a normal sinus rhythm. There are also frequent user errors associated with the stopcock or T-connector systems. If the wrong syringe is initially depressed, the full amount is not administered from one or both syringes, the stopcock is not fully adjusted to transition to the second syringe, or a variety of other issues occur, the consequences for the patient can be severe. The current system also involves a relatively large number of steps to set up and deliver, where improved time efficiency and reduced steps may be advantageous.

Adenosine is described by way of example, where numerous other medications and biologics, such as epinephrine, are delivered in a similar manner. Such other medications frequently have a short-half life, can result in life-threatening consequences if administered improperly, and/or can be inoperative if improperly administered.

BRIEF DESCRIPTION OF THE DRAWINGS

The present disclosure will be more readily understood from a detailed description of some example embodiments taken in conjunction with the following figures:

FIG. 4 depicts a cross-sectional view of the syringe-based delivery device of FIG. 2 taken along reference line A-A and shown in a pre-use configuration;

FIG. 5 depicts a cross-sectional view of the syringe-based delivery device of FIG. 2, shown with a plunger depressed to expel the medicament from the distal reservoir;

FIG. 6 depicts a cross-sectional view of the syringe-based delivery device of FIG. 2, shown with the plunger depressed to expel the flush fluid from the proximal reservoir.

FIG. 7 depicts a perspective view of a syringe-based delivery device having finger pads on a syringe portion according to an alternate embodiment.

FIG. 8A depicts a perspective view of a syringe-based delivery device having a locking mechanism according to one embodiment shown in a first position.

FIG. 8B depicts a perspective view of the syringe-based delivery device of FIG. 8, shown in a second position.

FIG. 15 depicts a cross-sectional view of the syringe-based delivery device of FIG. 2, shown with the plunger depressed to expel the medicament from the distal reservoir;

FIG. 16 depicts a cross-sectional view of the syringe-based delivery device of FIG. 2, shown with the plunger depressed to expel the flush fluid from the proximal reservoir.

FIG. 19 depicts a cross-sectional view of the syringe-based delivery device of FIG. 17 taken along reference line C-C and shown in a pre-use configuration.

FIG. 20 depicts a cross-sectional view of the syringe-based delivery device of FIG. 17, shown with a plunger urged distally to urge a first amount of fluid from a first fluid reservoir;

FIG. 21 depicts a cross-sectional view of the syringe-based delivery device of FIG. 17, shown with the plunger removed and a syringe attached having a second fluid reservoir;

FIG. 22 depicts a cross-sectional view of the syringe-based delivery device of FIG. 17, shown with a plunger of the syringe actuated distally to expel fluid from the second reservoir.

FIG. 26 depicts a cross-sectional view of the syringe-based delivery device of FIG. 24 taken along reference line D-D and shown in a pre-use configuration.

FIG. 27 depicts a cross-sectional view of the syringe-based delivery device of FIG. 24, shown with a seal removed from a housing of the delivery device.

FIG. 30 depicts a cross-sectional view of the syringe-based delivery device of FIG. 24, shown with a plunger of actuator mechanism actuated distally to expel fluid from the second reservoir.

FIG. 31 depicts a cross-sectional view of the syringe-based delivery device of FIG. 24, shown with the actuator mechanism urged distally to urge a second amount of fluid from the first fluid reservoir.

DETAILED DESCRIPTION

Figure 1:
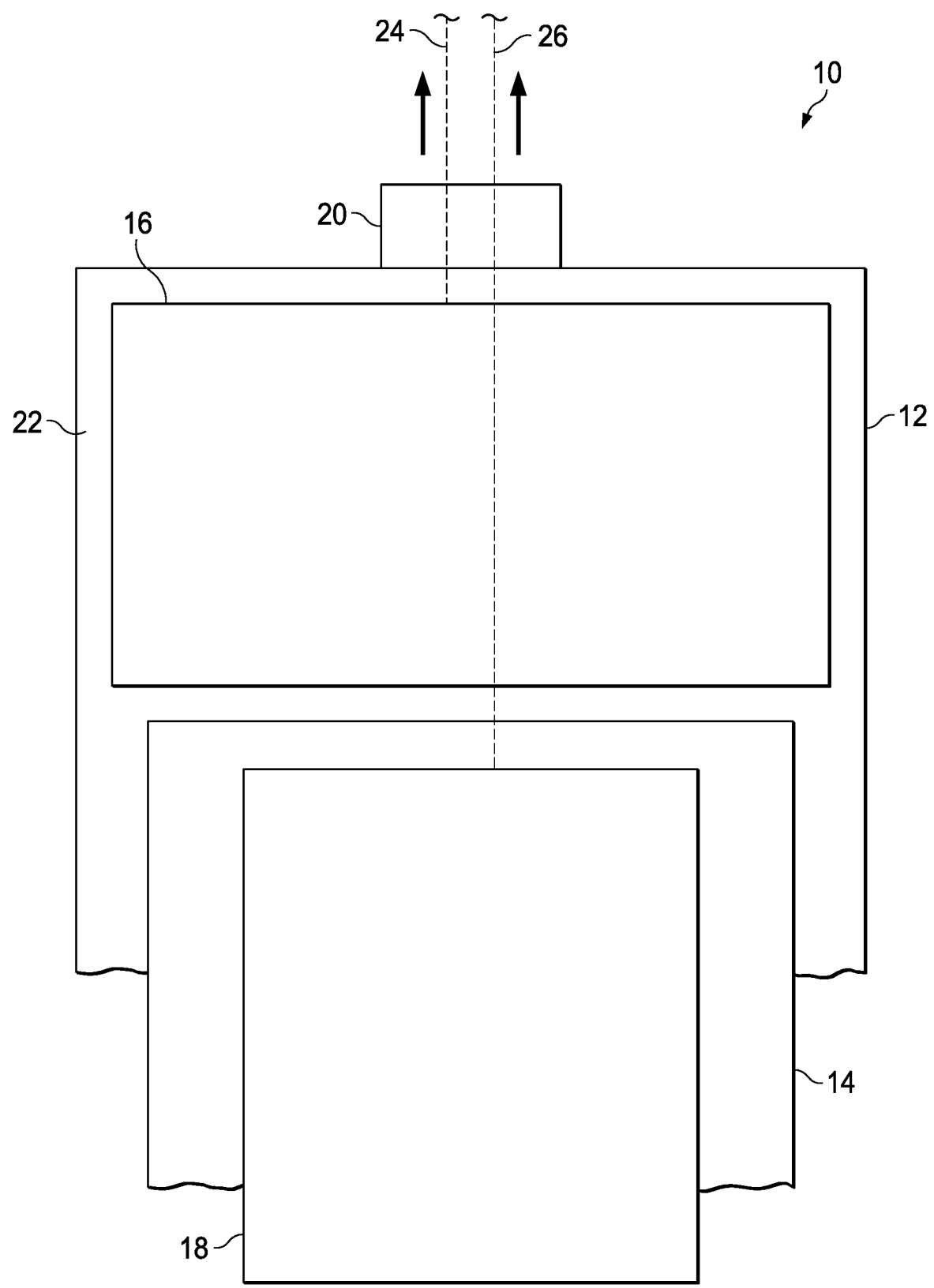
FIG. 1 is a schematic illustration of a syringe-based delivery device according to one embodiment.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure. Although embodiments in the figures as illustrated are shown as transparent or semi-transparent, it will be appreciated that any suitable features can be opaque, colored, or the like.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Described herein are example embodiments of apparatuses, systems, and methods for fluid delivery. In one example embodiment, a syringe-based fluid delivery system or syringe-based device can be provided that can deliver a first fluid that can include a medicament or biologic. In some embodiments, the syringe-based fluid delivery system can include a fluid flush that can be delivered to a patient immediately after the medicament or biologic is delivered. In some embodiments, the syringe-based fluid delivery system can include a pre-filled saline portion and a pre-filled medicament or biologic portion, where the saline flush can be delivered immediately following the medicament or biologic delivery. Embodiments of a syringe-based fluid delivery system can be configured to deliver a first portion of a flush fluid, deliver a medicament or biologic, and then deliver a second portion of a flush fluid. Some embodiments can include a syringe-based fluid delivery system that can be used to first draw a medicament or biologic into a first reservoir, deliver the medicament or biologic to the patient, and then administer a fluid flush. Embodiments of a syringe-based fluid delivery system can be used to deliver epinephrine, adenosine, or any other suitable fluid, component, drug, biologic or material. Embodiments of the syringe-based fluid delivery system can deliver any suitable flush such as, for example, 10 ml of saline, 20 ml of saline, heparin, or the like.

Referring now to FIG. 1, a schematic illustration of a portion of a syringe-based transfer device 10 is shown according to an embodiment. Generally, the syringe-based transfer device 10 (also referred to herein as "fluid transfer device," "integrated flush device," or "transfer device") can be designed or configured to facilitate the delivery of fluid to a patient such that a first type of fluid to be delivered as a medicament or biologic is fluidically isolated from a second type of fluid to be delivered as a fluid flush. The transfer device 10 can be configured to deliver a first, predetermined or selected amount of fluid from a first reservoir and a second amount of a different type of fluid from one or more reservoirs (e.g., fluid flush reservoirs) fluidically isolated from the first reservoir. Many drugs, such as adenosine, have a relatively short half-life (e.g., less than 10 seconds) and are used in potentially life threatening situations such as, for example, when a patient is experiencing supraventricular tachycardia (SVT). SVT can cause the heart to bear very rapidly or erratically, which can result in the heart beating inefficiently such that the body receives an inadequate blood supply. Delivery of a bolus amount of adenosine, such as 3, 6, 9, or 12 mg, can result in a conversion from SVT to a normal sinus rhythm. For such a bolus administration to reach the patient's heart it may be advantageous to provide, for example, a 20 ml saline flush as quickly as possible following the bolus adenosine delivery. Embodiments described herein may integrated the drug delivery (e.g., adenosine) with the fluid flush (e.g., saline) into a single device such that the fluid flush is delivered immediately or substantially immediately after delivery of the drug. In the illustrated example, adenosine can be provided in the first fluid reservoir 16 and the saline fluid flush can be provided in the second fluid reservoir 18. In an alternate embodiment, epinephrine (e.g., 1 mg) can be provided in the first fluid reservoir 16 and a fluid flush (e.g., 20 ml saline) can be provided in the second fluid reservoir 18.

The transfer device 10 can include a housing 12, an actuator mechanism 14, a first fluid reservoir 16 (also referred to herein as "first reservoir", "medicament reservoir", or "biologic reservoir"), and a second fluid reservoir 18 (also referred to herein as "second reservoir", "fluid flush reservoir", or "flush reservoir"), different from the first reservoir 16. The housing 12 can be any suitable shape, size, or configuration and is described in further detail herein with respect to specific embodiments. As shown in FIG. 1, the housing 12 can include a port 20 that can be at least temporarily physically and fluidically coupled to a medical device defining a pathway for delivering the first and second fluids from the transfer device 10. For example, the port 20 can be a LUER-LOK or the like configured to be physically and fluidically coupled to a peripheral intravenous line, a Central Venous Catheter (CVC) line, a needle, a cannula, other lumen-containing devices, or the like. In other embodiments, the port 20 can be monolithically formed with at least a portion of the lumen-containing device.

In example embodiments, the port 20 can include a one-way valve such that fluid flow is unidirectional out of the transfer device 10 in the direction shown by the arrows of FIG. 1. The one-way valve can be monolithically formed with the port 20, fixedly coupled with the port 20, or selectively coupled with the port 20. In certain embodiments, the one-way valve can be threadedly coupled with the port 20, attached with a press fit, or can be formed as a one piece, unitary construction with the port 20. During use, the one-way valve can prevent fluid, such as fluid from a peripheral IV, from being accidentally drawn into the port 20 and the transfer device 10.

As shown in FIG. 1, the housing 12 can define an inner volume 22 that can be configured to receive a portion of the actuator mechanism 14. More specifically, the actuator mechanism 14 can be at least partially disposed within the inner volume 22 defined by the housing 12 and can be movable between a first configuration and a second configuration relative to the housing 12. The housing 12 can also be configured to define at least a portion of the first reservoir 16 as will be described in more detail herein.

The first reservoir 16 can be at least partially defined by a set of walls of the housing 12 that define the inner volume 22. For example, the first reservoir 16 can be a cavity defined by the distal end or plunger of the actuator mechanism 14 and the housing 12, where the plunger and housing 12 can cooperate to form a substantially fluidically sealed chamber. The first reservoir 16 can have a variable volume, where urging or drawing the actuator mechanism 14 proximally such as, for example, when the transfer device 10 is being pre-filled, can correspondingly increase the volume of the first reservoir 16. A portion of the piston or plunger can form a substantially fluid tight seal with the walls of the housing 12 defining the inner volume 22. In this manner, the housing 12 and the actuator mechanism 14 can collectively form a sealed, air-tight cavity (e.g., a syringe) such that the actuator mechanism 14 (or at least a portion of the actuator mechanism 14) can urge outward and expel fluid contained within the inner volume 22.

In certain embodiments, the second reservoir 18 can be housed within a portion of the actuator mechanism 14 and can be configured to retain and dispense any suitable fluid, such as a 10 ml or 20 ml saline flush. The second reservoir 18 can be defined by any suitable structure or combination of structures such as, for example, a syringe having a plunger and a threaded distal end that is selectively coupled with a one-way valve. The syringe can be used to expel fluid, such as a fluid flush, out of the second reservoir 18, where the syringe defining the second reservoir 18 can be selectively removable from the actuator mechanism 14 in one embodiment.

There are circumstances in which it may be advantageous to selectively attach the second reservoir 18 from the transfer device 10. For example, in neonatal applications it may be desirable to provide a lower volume of saline flush (e.g., 5 ml) such that a smaller syringe and/or smaller second reservoir 18 can be provided. Providing a selectively attachable second reservoir 18 in the form of a selectively attachable syringe can allow for any suitable volume or type of fluid to be coupled with the transfer device 10 as needed. Any suitable mechanism to expel the fluid from the second reservoir 18 is contemplated where, for example, the syringe can include a plunger that can be used to expel such fluid.

The actuator mechanism 14 can have any suitable shape, size, or configuration and can include any suitable number or type of components. For example, in some embodiments, the shape and size of at least a portion of the actuator mechanism 14, such as the outer portion, can substantially correspond to the shape and size of the walls of the housing 12 defining the inner volume 22. As described above, at least a portion of the actuator mechanism 14 can be movably disposed within the inner volume 22 of the housing 12. For example, in some embodiments, a distal end portion of the actuator mechanism 14 can be disposed within the inner volume 22 of the housing 12 and a proximal end portion of the actuator mechanism 14 can be disposed substantially outside the housing 12. In such embodiments, a user can engage the proximal end portion of the actuator mechanism 14 to move the portion of the actuator mechanism 14 disposed within the inner volume 22 distally to expel fluid from the first reservoir 16.

In some embodiments, the actuator mechanism 14 can include a first member and a second member. The first member and the second member can be collectively moved within the inner volume 22 of the housing 12. In addition, the first member and the second member can be configured to move independently within the housing 12. Similarly stated, the first member can be moved relative to the second member and/or the second member can be moved relative the first member, as further described herein with respect to specific embodiments. In some embodiments, the first member and/or the second member can form a piston or plunger configured to move within the inner volume 22. In one embodiment the first member is a fluid flush syringe and the second member cooperates with the housing 12 to function as a second syringe. Such a system can be described as a "dual syringe" system.

The second reservoir 18 can be any suitable reservoir for containing, for example, a fluid flush. For example, in some embodiments, the second reservoir 18 can be defined by an internal syringe comprising the first member of the actuator mechanism 14. In some embodiments, the second reservoir 18 can be a saline flush reservoir, but any suitable fluid, such as a second medication or biologic, is contemplated. The second reservoir 18 can be selectively placed in fluid communication with the housing 12 or the actuator mechanism 14. The second reservoir 18 and/or the first member (e.g., a fluid flush syringe) can be selectively attachable from the actuator mechanism 14.

The first reservoir 16 can be any suitable reservoir and can be configured to receive and contain a first type and amount of fluid. In some embodiments, the first reservoir 16 can be defined by a portion of the walls of the housing 12 defining the inner volume 22 and a portion of the actuator mechanism 14. In this manner, when the actuator mechanism 14 is in the first configuration, a portion of the actuator mechanism 14 and a portion of the housing 12 can define a first fluid flow path 24 to fluidically couple the port 20 to the first reservoir 16. It will be appreciated the first and second fluid flow paths 24, 26, as described herein, can pass initially through the same lumen of the port 20. In an alternate embodiment, the first fluid flow path 24 can pass through a first port, and the second fluid path can pass through a second port, where the first port and the second port can be fluidically isolated. In some embodiments, the movement of the actuator mechanism 14 distally can be such that the distally applied force facilitates the flow of the fluid through the first fluid flow path 24 and out of the first reservoir 16. In certain embodiments, the first type and amount of fluid can be an amount given to the patient subsequent to delivery of the second type and amount of fluid. In some embodiments, the first reservoir 16 can contain the first type of fluid such that the first amount and type is fluidically isolated from the second amount and type of fluid.

The second reservoir 18 can be sized to receive and contain, for example, a predetermined amount of a flush fluid. During use, the first member (e.g., a syringe) of the actuator mechanism 14 can define a second fluid flow path 26 to fluidically couple the port 20 of the housing 12 to the second reservoir 18. In some embodiments, a portion of the actuator mechanism 14, such as the plunger of the syringe, can be urged distally and can facilitate the distal flow of the flush fluid through the second fluid flow path 26 and out of the second reservoir 18. The second reservoir 18 can be designed and sized to retain the first type of fluid such that the first type is fluidically isolated from a second type of fluid (different from the first type of fluid) that is subsequently given to the patient.

In certain embodiments, the actuator mechanism 14 and the second reservoir 18 can be sized and configured with a pre-set amount of fluid that can be administered during a procedure. Such a pre-set embodiment may be desirable when a consistent amount of fluid flush is given during most or all medicament or biologic delivery procedures. For example, the actuator mechanism 14 and second reservoir 18 can be size to retain about 10 ml of fluid, about 20 ml of fluid, or any other suitable amount of fluid. In alternate embodiments, it may be desirable to provide a user-selectable volume of fluid to be provided in the second reservoir 18. For example, in neonatal applications it may be desirable to provide 5 ml or less of fluid, whereas for a larger adult it may be desirable to deliver from about 10 ml to about 20 ml of flush fluid. User selectable, variable volume embodiments are contemplated.

As described above, the transfer device 10 can be used to transfer a fluid to a patient from the second reservoir 18 and/or first reservoir 16 included in the transfer device 10. More specifically, the flow of the first amount of fluid transferred from the first reservoir 16 can be any suitable medicament, biologic, or the like such as, for example, adenosine, epinephrine, atropine, etomidate, rocuronium, succinylcholine, NARCAN, amiodarone, or the like. The first reservoir 16 can fluidically isolate the first type of fluid such that when second type of fluid retained within the second fluid reservoir 18 does not mix with the first type of fluid.

In some embodiments, the transfer device 10 can be configured such that the first type of fluid must be conveyed from the first reservoir 16 through the first fluid flow path 24 before the transfer device 10 will permit the flow of the second type of fluid through the second fluid flow path 26 from the second reservoir 18. In such embodiments, the transfer device 10 can be characterized as requiring compliance by a health care practitioner regarding the delivery of the first, predetermined amount (e.g., 1 mg of epinephrine) prior to delivery of the second amount (e.g., a 20 ml saline flush) of fluid. Similarly stated, the transfer device 10 can be configured to prevent a health care practitioner from delivering the second fluid type, such as a fluid flush, fluid from the second reservoir 18 without first diverting the first type of fluid out of the first reservoir 16. In this manner, the health care practitioner can be prevented from delivering (whether intentionally or unintentionally) the second type of fluid from the second reservoir 18 before delivering the first type of fluid from the first reservoir 16. For example, a clinician can be prevented from administering a saline flush before delivering a medicament or biologic to a patient.

FIGS. 2-6 illustrate a syringe-based transfer device 110 according to an embodiment. The syringe-based transfer device 110 (also referred to herein as "fluid transfer device," "integrated flush device," or "drug delivery device") includes a housing 112 and an actuator mechanism 114. The transfer device 110 can be configured to include or define a first fluid reservoir 116 (also referred to herein as "first reservoir" or "medicament reservoir") and a second fluid reservoir 118 (also referred to herein as "second reservoir" or "fluid flush reservoir"). The transfer device 110 can be any suitable shape, size, or configuration. For example, while shown in FIGS. 2 and 3 as being substantially cylindrical, the transfer device 110 can be square, rectangular, polygonal, and/or any other non-cylindrical shape.

Figure 2:
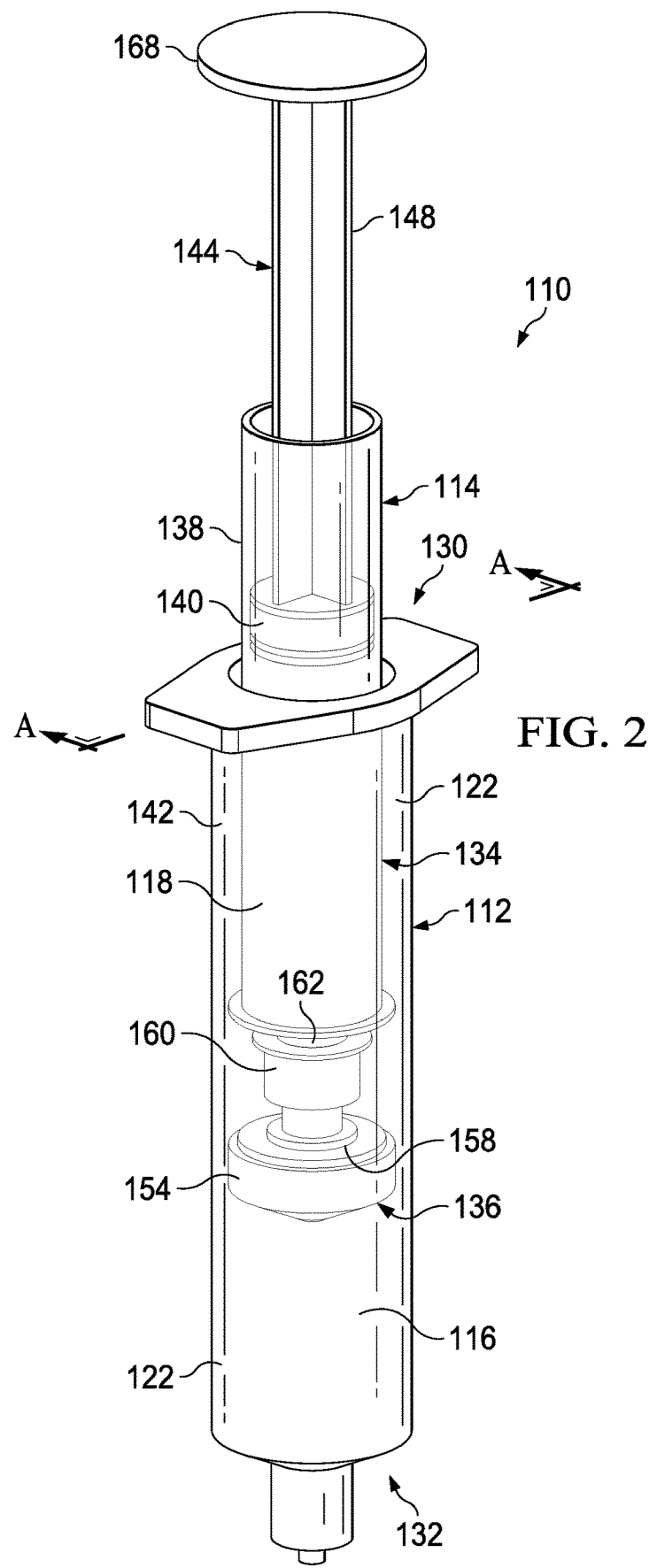
FIG. 2 depicts a perspective view of a partially transparent syringe-based delivery device having a distal reservoir for a medicament and a proximal reservoir for a flush fluid according to one embodiment.
Figure 3:
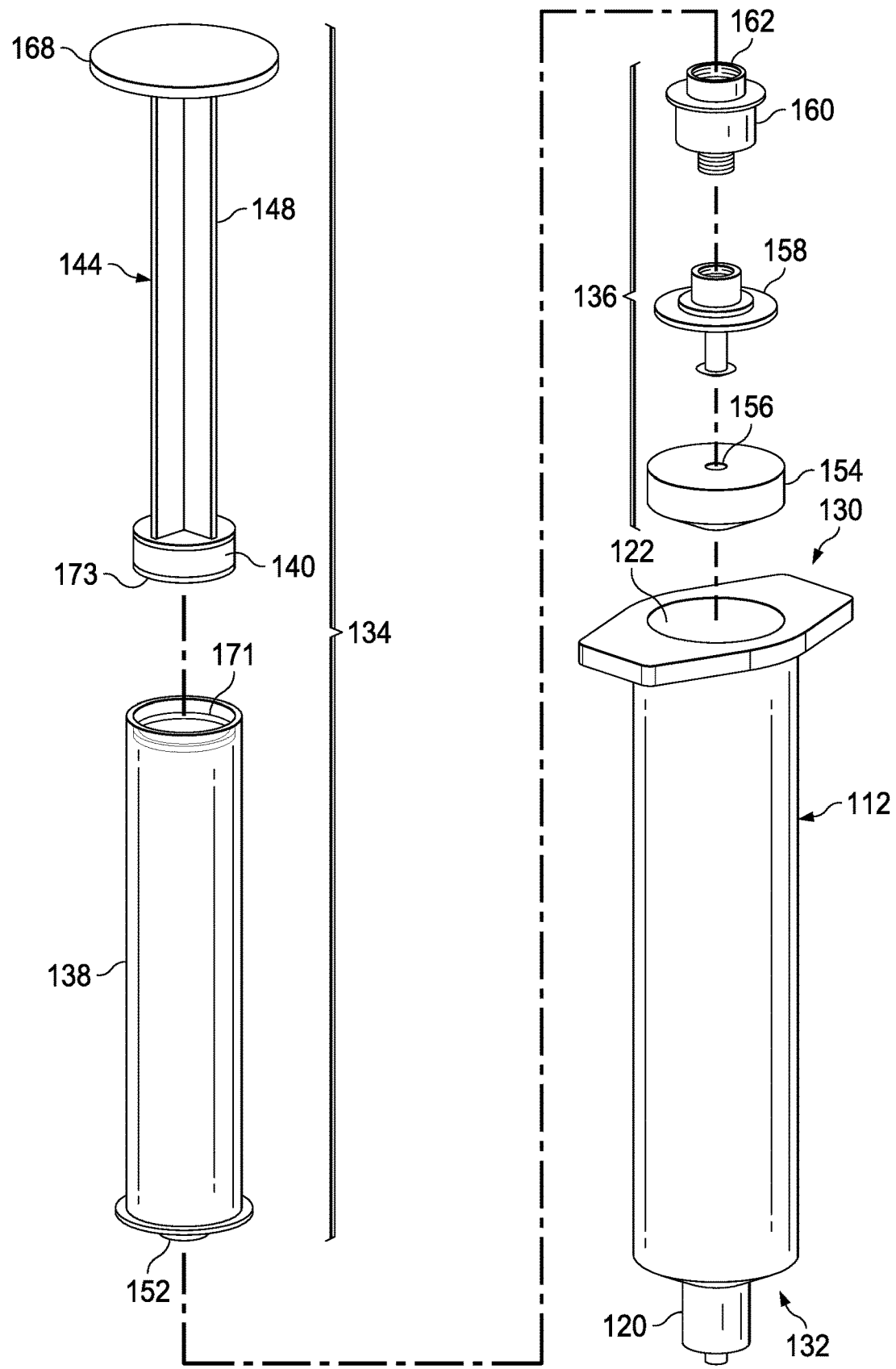
FIG. 3 depicts an exploded view of the syringe-based delivery device shown in FIG. 2.

As shown in FIGS. 2 and 3, the housing 112 can include a proximal end portion 130 and a distal end portion 132 and can define an inner volume 122 therebetween. In some embodiments, the housing 112 can be substantially similar to a syringe body. The proximal end portion 130 of the housing 112 can be substantially open and can be configured to receive at least a portion of the actuator mechanism 114 such that at least the portion of the actuator mechanism 114 can be movably disposed within the inner volume 122. Furthermore, the inner volume 122 can be configured to define the first fluid reservoir 116, as further described herein. The distal end portion 132 of the housing 112 can include a port 120. In some embodiments, the port 120 can be monolithically formed with the housing 112 (e.g., as shown in FIGS. 2 and 3). In other embodiments, the port 120 can be coupled to the distal end portion 132 in any suitable manner such as, for example, via a friction fit, a threaded coupling, a mechanical fastener, an adhesive, any number of mating recesses, and/or any combination thereof.

The port 120 can be any suitable shape, size, or configuration. For example, in some embodiments, at least a portion of the port 120 can form a lock mechanism configured to be physically and fluidically coupled to a peripheral IV line, a Central Venous Catheter (CVC) line, a needle, a cannula, or other lumen-containing device. For example, in some embodiments, the port 120 can be a LUER-LOK or similar locking mechanism that can be configured to physically and fluidically couple to a CVC line (not shown). In other embodiments, the port 120 can be monolithically formed in a unitary, one piece construction with at least a portion of the lumen-containing device. In this manner, the port 120 can be placed in fluid communication with a lumen defined by the lumen-defining device and to receive the bodily-fluid from a patient when the lumen-defining device is disposed within the patient.

The actuator mechanism 114 can be disposed within the inner volume 122 and can be movable between a first position (e.g., a proximal position relative to the housing 112) and a second position (e.g., a distal position relative to the housing 112). The movement of the actuator mechanism 114 relative to the housing 112 can move the transfer device 110 between a number of different configurations and positions, as further described herein. The actuator mechanism 114 can include a first member 134 and a second member 136. The first member 134 of the actuator mechanism 114 can include a plunger 144 and a syringe body 138 that can define an inner volume 142 therebetween. At least a portion of the inner volume 142 can be configured to define the second fluid reservoir 118, as further described herein. The plunger 144 can include a plunger seal 140 that can fluidically seal the second fluid reservoir 118. The syringe body 138 can include an open proximal end such that the plunger 144 can be movably disposed within the inner volume 142.

The distal end portion of the first member 134 can include an attachment element 152, such as a LUER-LOK or similar locking or coupling mechanism, that can be configured to selectively physically and fluidically couple the first member 134 with the second member 136. The attachment element 152 can be threadedly engaged with the second member 136 such that rotation of the first member 134 (e.g., 90 degrees in a clockwise direction) will disengage the first member 134 from the 136. The attachment element 152 can include a port which can, for example, be similar in construction and operation to port 120 described herein. It will be appreciated that the attachment element 152 can be selectively attached and decoupled from the second member 136 in any suitable manner such as, for example, with a threaded engagement, a snap fit, and friction fit, a user-accessible locking mechanism, or the like.

The second member 136 can include a plunger seal 154 that can form a friction fit with the inner surface of the walls defining the inner volume 122 when the actuator mechanism 114 is disposed within the housing 112. Similarly stated, the plunger seal 154 can define a fluidic seal with the inner surface of the walls defining the inner volume 122 such that a portion of the inner volume 122 distal of the plunger seal 154 is fluidically isolated from a portion of the inner volume 122 proximal of the plunger seal 154. The plunger seal 154 can define a channel 156 that that can extend through a distal end and a proximal end of the plunger seal 154. A portion of an inner set of walls defining the channel 156 can accept a valve seat 158. In this manner, a portion of the channel 156 can receive a valve 160 that can be in contact with the valve seat 158. The valve 160 can include a threaded proximal end 162 or threaded proximal portion that can selectively engage the attachment element 152 of the first member 134 as described herein.

The valve 160 can be any suitable valve. For example, in some embodiments, the valve 160 can be a one-way check valve to allow a flow of a fluid from a proximal end of the valve 160 to a distal end of the valve 160, but substantially not allow a flow of the fluid from the distal end to the proximal end. The valve 160 can be disposed within the channel 156 and can be in contact with the valve seat 158 such that the valve 160 forms a substantially fluid tight seal with the walls defining the channel 156. In some embodiments, the valve 160 can form a friction fit with walls defining the channel 156. In other embodiments, the valve 160 can form a threaded coupling or the like with at least a portion of the walls. The valve 160 can also include a seal member configured to engage the valve seat 158 to form at least a portion of the fluid tight seal.

As described above, the second member 136 can be movably disposed within the housing 112. More specifically, the second member 136 can be movable between a first configuration (e.g., a proximal position) and a second configuration (e.g., a distal position) to create positive pressure to urge for example, a medicament, out of the first fluid reservoir 116. A first coefficient of friction between the plunger seal 140 and the syringe body 128 can be greater than a second coefficient of friction between the plunger seal 154 and the housing 112. In this manner, the distal translation of the plunger 144 can first cause the plunger seal 154 to move distally to expel the fluid from the first fluid reservoir 116. Once the first fluid reservoir 116 has been emptied through the port 120, where the plunger seal 154 may now be seated at the about distal end portion 132 of the housing, continued distal movement of the plunger 133 can result in distal movement of the plunger seal 140 such that the fluid retained within the second fluid reservoir 118 is expelled out of the syringe body 128 and through the port 120. In embodiments where relying upon the difference in the coefficients of friction between the plunger seal 140 and the plunger seal 154 alone is insufficient, an annular catch 171 can be provided on the syringe body 138 that can engage a portion 173 of the plunger seal 140 that can extend radially outward. The annular catch 171 and the portion 173 can cooperate in an interference fit, where the annular catch 171 and the portion 173 can be sized and otherwise configured to require a threshold of force to overcome the interference fit that is greater than the force required to advance the plunger seal 154 distally. It will be appreciated that the syringe body 138, the plunger seal 140, and/or any other components can be modified to prevent the second fluid reservoir 118 from being expelled before the first fluid reservoir 116 is expelled.

In use, a user can engage the transfer device 110 to couple the port 120 to a proximal end portion of a lumen-defining device (not shown) such as, for example, a CVC line, a PICC line, a butterfly needle, a cannula assembly, a trocar, or the like. With the port 120 physically coupled to the lumen-defining device, the port 120 can be placed in fluid communication with the lumen defined by the lumen-defining device. The distal end portion of the lumen-defining device can be disposed within a portion of the body of a patient (e.g., a vein). In this manner, the port 120 can be placed in fluid communication with the portion of the body.

With the port 120 coupled to the lumen-defining device, a user (e.g., a phlebotomist, a nurse, a technician, a physician, or the like) can move the transfer device 110 from a first configuration (FIG. 4) to a second configuration (FIG. 5). More specifically, the user can depress an engagement portion 168 of the plunger 144 to move the plunger seal 154 distally to create positive pressure within the first fluid reservoir 116. As shown in FIG. 5, the positive pressure in the first fluid reservoir 116 can urge the fluid, such as a medicament or biologic, through the port 20 and into the patient. The plunger seal 154 can be urged in a distal direction relative to the housing 112 until the plunger seal is seated against the distal end portion 132 of the housing.

In certain embodiments, the arrangement of the plunger 144 within the syringe body 138 is such that the distal motion of the plunger 144 does not decrease or substantially decrease the inner volume 142 that is distal of the plunger seal 140, which can contain the second fluid reservoir 118. With the plunger seal 140 forming a fluid tight seal with the inner surface of the walls defining the inner volume 142, the increase of pressure can first fully distally advance the plunger seal 154 before the plunger seal 140 can move relative to the syringe body 138.

As shown in FIG. 6, the transfer device can be transitioned from a second configuration to a third configuration. The port 120, the valve 160, the attachment element 152, and the channel 156 can define a fluid flow path that places the second fluid reservoir 118 in fluid communication with the lumen-defining device (not shown) connected to the patient. Therefore, the second fluid reservoir 118 can correspondingly be placed in fluid communication with the portion of the patient (e.g., the vein). The positive pressure within the second fluid reservoir 118 can be operative in moving the valve 160 from a closed configuration to an open configuration. In this manner, the positive pressure within the within the second fluid reservoir 118 that can be produced by the movement of the plunger 144 can urge the fluid within the second fluid reservoir 118 out of the transfer device 10. Fluid can be urged out of the second fluid reservoir 118, through the syringe body 138, through the attachment element 152, through the valve 160, and through the port 20 into the patient. In some embodiments, the fluid expelled from the second fluid reservoir 118 can be a fluid flush, such as a 20 ml saline flush.

In some embodiments, the magnitude of the positive pressure can be modulated by increasing or decreasing the amount of a force applied to the plunger 144. For example, in some embodiments, it can be desirable to limit the amount of positive pressure introduced to a vein or through a line. In such embodiments, the user can reduce the amount of force applied to the engagement portion 168. In this manner, the rate of change (e.g., the decrease) in the volume of the first fluid reservoir 116 can be sufficiently slow to allow time for the positive pressure differential between the vein and the fluid reservoir to come to equilibrium before further decreasing the volume of the first fluid reservoir 116. Thus, the magnitude of the positive pressure can be modulated.

While in the third configuration, the transfer device 110 can be configured to transfer a desired amount (e.g., a predetermined amount or a user-selected amount) of fluid out of the second fluid reservoir 118. In some embodiments, the volume can substantially correspond to the size of the second fluid reservoir 118. In other embodiments, the volume can be monitored and determined by the clinician as they depress the plunger 144 distally. When distal pressure on the plunger 144 is alleviated the valve 160 may be allowed to close.

The arrangement of the first member 134 and the second member 136 within the inner volume 122 of the housing 112 can be such that the proximal motion of the first member 134 and second member 136 decreases the volume of the portion of the inner volume 122 that is distal of the plunger seal 154, such that the first fluid reservoir 116 is emptied before the second fluid reservoir 118 is emptied. With the plunger seal 154 seated against the distal end portion 132 of the housing, the continued positive pressure in a distal direction applied to the plunger 144 can then empty the second fluid reservoir 118.

In some embodiments, the volume of the first fluid reservoir 116 is sufficient to contain a desirable amount of a medicament or biologic. In other embodiments, the first fluid reservoir 116 can contain from about 0.1 ml to about 3.0 ml. In still other embodiments, the first fluid reservoir 116 can contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. In one embodiment, the pressure within the first fluid reservoir 116 can be such that the force applied to the plunger 144 does not substantially move the first member 134 relative to the second member 136. In such examples, the force applied to the engagement portion 168 can collectively move the second member 136 and the first member 134 in the distal direction relative to the housing 112 to expel the fluid from the first fluid reservoir 116 into the lumen-defining device of the patient.

In alternate embodiment, as shown in FIG. 7, the syringe body 138 can include a pair of radial flanges 170 at about the distal end of the syringe body, where the radial flanges 170 can be urged distally to move the syringe body 138 relative to the housing 112, where such motion can expel the fluid from the first fluid reservoir 116. Once the fluid has been expelled from the first fluid reservoir 116, the plunger 144 can subsequently be depressed to expel the fluid from the second fluid reservoir 118. The variance in the coefficient of friction between the plunger seal 140 and the plunger seal 154 may be sufficient to permit distal actuation of the plunger 144 to expel the first fluid reservoir 116 before expelling the second fluid reservoir 118. However, other mechanical features are contemplated, such as thumb pads to depress the syringe body 138, where the plunger 144 may only need to be depressed to expel fluid from the second fluid reservoir 118. It is further contemplated that the syringe body 138 and the plunger 144 can be mechanically coupled to prevent relative movement between the syringe body 138 and the plunger 144 until such a coupling is decoupled. The coupling can include a latch, pin, lock, clasp, or any other suitable coupling that can temporarily limit relative movement between the plunger and the syringe body until it is desirably to expel from fluid from the second fluid reservoir 118.

Figure 8C:
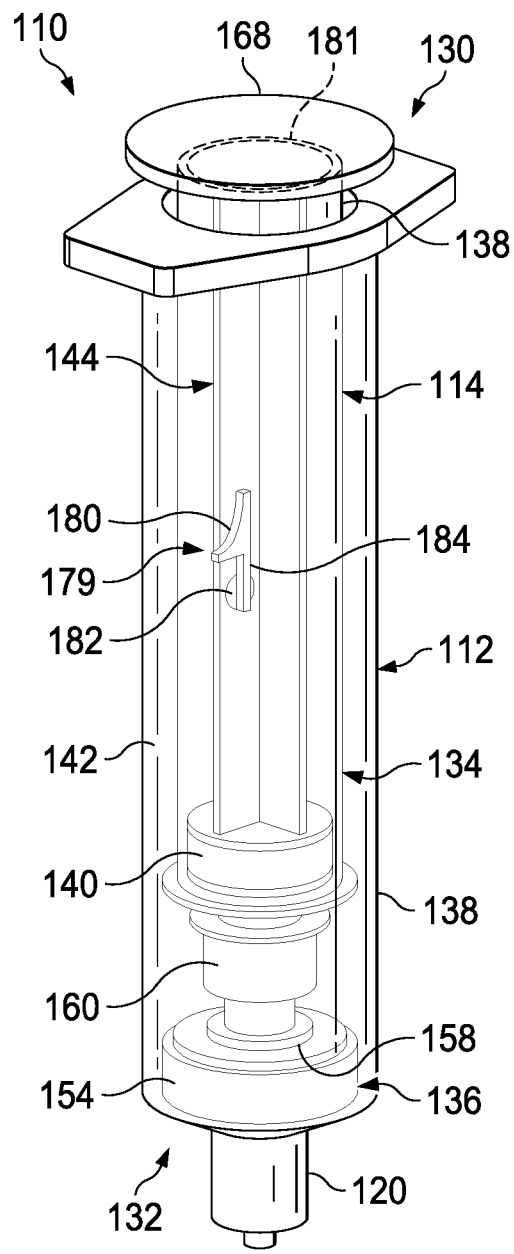
FIG. 8C depicts a perspective view of the syringe-based delivery device of FIG. 8, shown in a third position

FIGS. 8A-8C illustrate a perspective view of a transfer device 110 having a locking mechanism 179 according to one embodiment. As described above, it may be desirable to prevent relative movement between the plunger 144 and the syringe body 138 until the fluid in the first fluid reservoir 116 has been fully dispensed. In addition to, or in place of, an interference fit between the annular catch 171 and the portion 173 of the plunger seal 140, the transfer device can include the locking mechanism 179. The locking mechanism 179 can include a radial projection 180 that can be pivotable radially outward about a pin 182. In a first locked position (FIGS. 8A and 8B), the radial projection can be pivoted outward such that it is substantially perpendicular to the axis of motion of the plunger 144. The radial projection 180 can define a cutout or stop 184 that can engage the proximal surface 181 of the syringe body 138. As shown in FIG. 8B, in the closed position, the locking mechanism 179 will result in distal movement of the plunger 144 correspondingly moving the syringe body 138 in the distal direction. In this manner the locking mechanism 179 can help insure that the fluid in the first fluid reservoir 116 is expelled before the fluid in the second fluid reservoir 118 is expelled.

As shown in FIG. 8C, after the plunger 144 has been depressed to expel the fluid from the first fluid reservoir 116, the radial projection 180 can be pivoted, for example, about 90 degrees, such that the radial projection 180 is substantially parallel to the axis of motion of the plunger 144. In this "open" position, as illustrated, the radial projection 180 does not interfere with the proximal surface 181 of the syringe body 138, where the radial projection 180 can now pass within the syringe body 138. In use, after the fluid has been dispensed from the first fluid reservoir 116, the locking mechanism 179 can be "opened" or transitioned to the second position such that the plunger 144 can be depressed to expel fluid from the second fluid reservoir 118.

Figure 9:
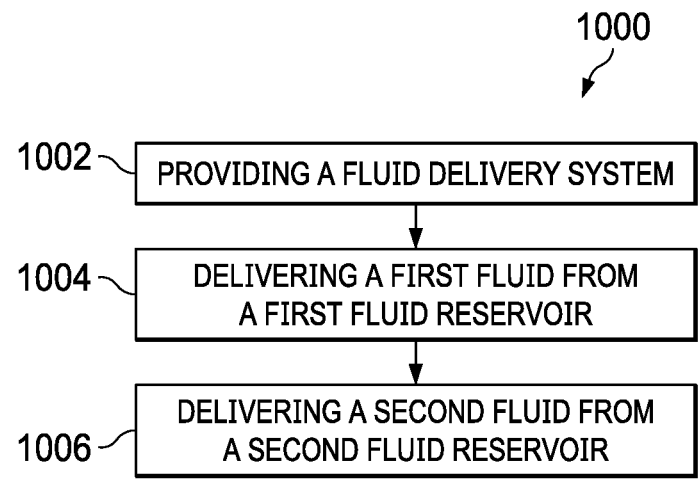
FIG. 9 depicts a flow chart showing a method of operating a syringe-based delivery device according to one embodiment.

FIG. 9 illustrates a flow chart depicting a Method 1000 for using a fluid transfer device, such as fluid transfer device 110. Method 1000 can include Providing a Fluid Delivery Device 1002, which can include providing any suitable fluid transfer device. Method 1000 can include Delivering a First Fluid from a First Fluid Reservoir 1004, which can include dispensing a medicament or a biologic from the first fluid reservoir 116. Method 1000 can include Delivering a Second Fluid from a Second Fluid Reservoir 1006, which can include dispensing a flush fluid from the second fluid reservoir 118.

Figure 10:
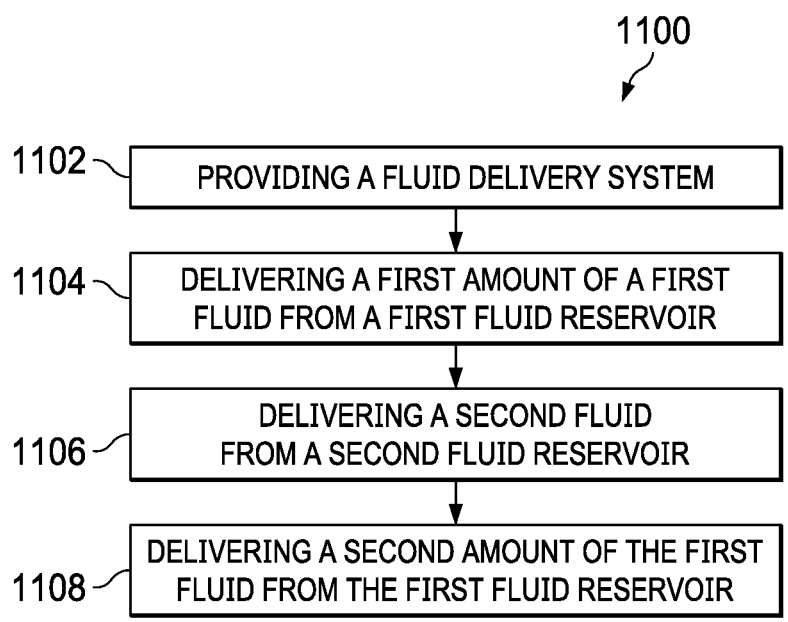
FIG. 10 depicts a flow chart showing a method of operating a syringe-based delivery device according to one embodiment.

FIG. 10 illustrates a flow chart depicting a Method 1100 for using a fluid transfer device, such as fluid transfer device 310, 410, and 510, as described herein. Method 1100 can include Providing a Fluid Delivery System 1102. Method 1100 can include Delivering a First Amount of a First Fluid from a First Fluid Reservoir 1104, which can include delivering a first amount of a saline flush. Method 1100 can include Delivering a Second Fluid from a Second Fluid Reservoir 1106, which can include delivering a medicine with a syringe. Method 1100 can include Delivering a Second Amount of the First Fluid from the First Fluid Reservoir 1108, which can include delivering a second amount of the saline flush.

FIGS. 11-16 illustrate a syringe-based transfer device 210 according to an embodiment. The syringe-based transfer device 210 (also referred to herein as "fluid transfer device," "integrated flush device," or "drug delivery device") includes a housing 212 and an actuator mechanism 214. The transfer device 210 can be configured to define a first fluid reservoir 216 (also referred to herein as "first reservoir" or "medicament reservoir") and a second fluid reservoir 218

(also referred to herein as "second reservoir" or "fluid flush reservoir"). The transfer device 210 can be any suitable shape, size, or configuration. For example, while shown in FIGS. 11 and 12 as being substantially cylindrical, the transfer device 210 can be square, rectangular, polygonal, and/or any other non-cylindrical shape.

Figure 11:
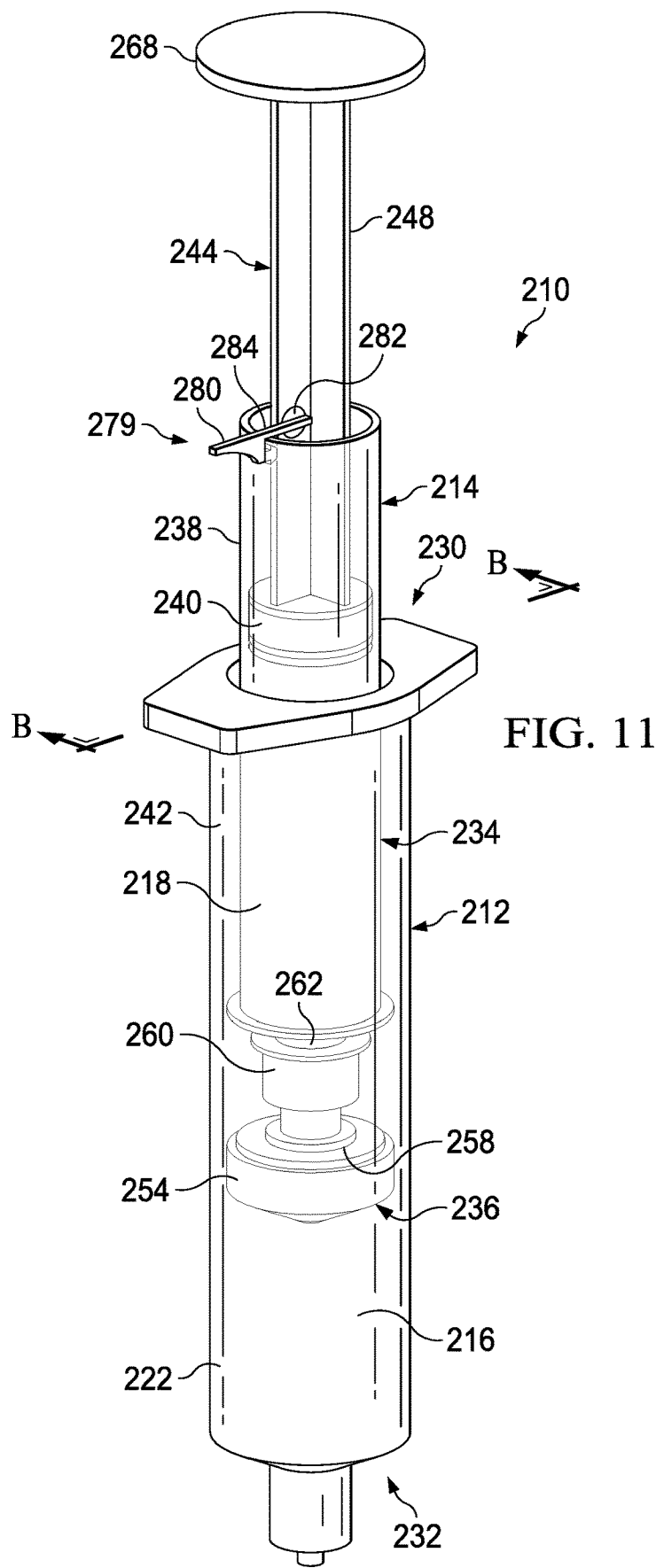
FIG. 11 depicts a perspective view of a syringe-based delivery device according to an alternate embodiment.
Figure 12:
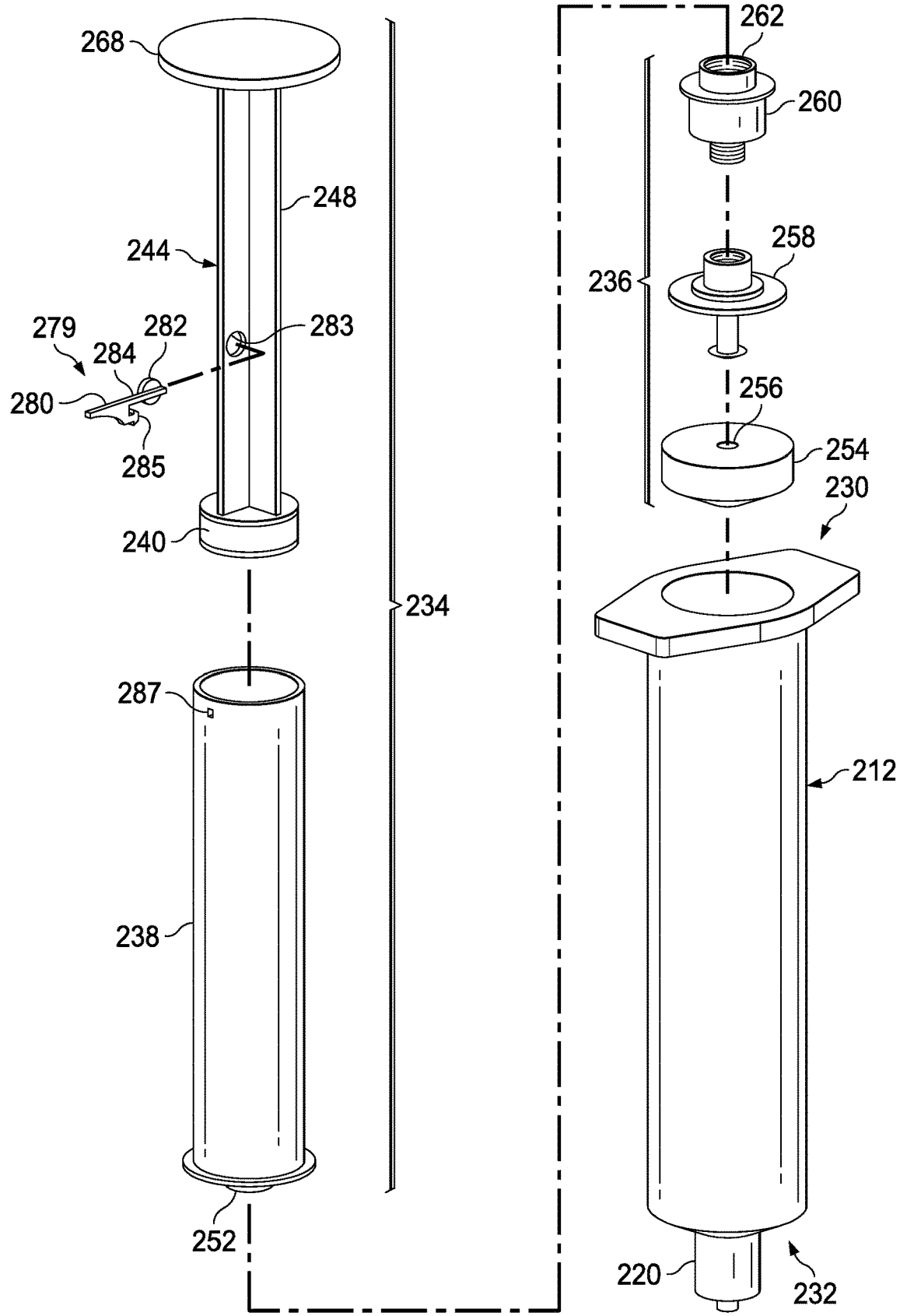
FIG. 12 depicts an exploded view of the syringe-based delivery device of FIG. 11.

As shown in FIGS. 11 and 12, the housing 212 can include a proximal end portion 230 and a distal end portion 232 and can define an inner volume 222 therebetween. In some embodiments, the housing 212 can be substantially similar to a syringe body. The proximal end portion 230 of the housing 212 can be substantially open and can be configured to receive at least a portion of the actuator mechanism 214 such that at least the portion of the actuator mechanism 214 can be movably disposed within the inner volume 222. Furthermore, the inner volume 222 can be configured to define the first fluid reservoir 216, as further described herein. The distal end portion 232 of the housing 212 can include a port 220. In some embodiments, the port 220 can be monolithically formed with the housing 212 (e.g., as shown in FIGS. 11 and 12). In other embodiments, the port 220 can be coupled to the distal end portion 232 in any suitable manner such as, for example, via a friction fit, a threaded coupling, a mechanical fastener, an adhesive, any number of mating recesses, and/or any combination thereof.

The port 220 can be any suitable shape, size, or configuration. For example, in some embodiments, at least a portion of the port 220 can form a lock mechanism configured to be physically and fluidically coupled to a peripheral IV line, a Central Venous Catheter (CVC) line, a needle, a cannula, or other lumen-containing device. For example, in some embodiments, the port 220 can be a LUER-LOK or similar locking mechanism that can be configured to physically and fluidically couple to a CVC line (not shown). In other embodiments, the port 220 can be monolithically formed in a unitary, one piece construction with at least a portion of the lumen-containing device. In this manner, the port 220 can be placed in fluid communication with a lumen defined by the lumen-defining device and to receive the bodily-fluid from a patient when the lumen-defining device is disposed within the patient.

Figure 13:
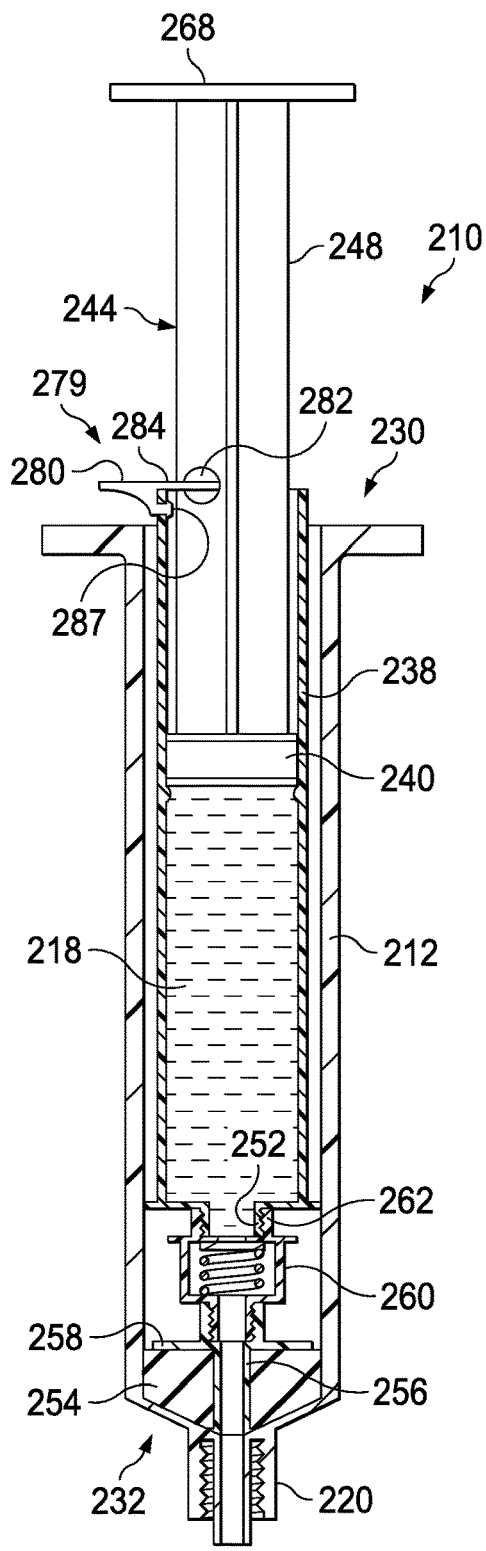
FIG. 13 depicts a cross-sectional view of the syringe-based delivery device of FIG. 11 taken along reference line B-B and shown in a pre-use configuration.
Figure 14:
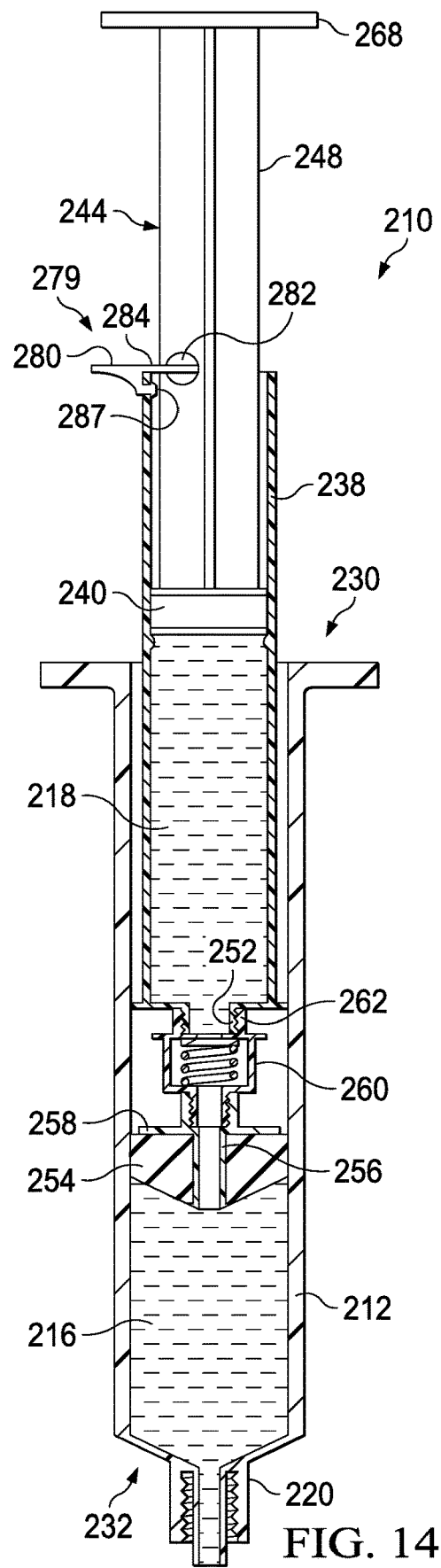
FIG. 14 depicts a cross-sectional view of the syringe-based delivery device of FIG. 2, shown with a plunger urged proximally to draw a medicament into a distal reservoir.

The actuator mechanism 214 can be disposed within the inner volume 222 and can be movable between a first configuration (e.g., a distal position relative to the housing 212, as shown in FIG. 13) and a second configuration (e.g., a proximal position relative to the housing 212, as shown in FIG. 14). The movement of the actuator mechanism 214 relative to the housing 212 can move the transfer device 210 between a number of different configurations and positions, as further described herein. The actuator mechanism 214 can include a first member 234 and a second member 236. The first member 234 of the actuator mechanism 214 can include a plunger 244, a locking mechanism 279, and a syringe body 238, where the syringe body 238 and plunger 244 can define an inner volume 242. At least a portion of the inner volume 242 can define the second fluid reservoir 218, as further described herein. The plunger 244 can include a plunger seal 240 that can fluidically seal the second fluid reservoir 218. The syringe body 238 can include an open proximal end such that the plunger 244 can be movably disposed within the inner volume 242.

The distal end portion of the first member 234 can include an attachment element 252, such as a LUER-LOK or similar locking or coupling mechanism, that can be configured to selectively physically and fluidically couple the first member 234 with the second member 236. The attachment element 252 can be threadedly engaged with the second member 236 such that rotation of the first member 234 (e.g., 90 degrees in a clockwise direction) can disengage the first member 234 from the 236. The attachment element 252 can include or can be a port which can, for example, be similar in construction and operation to port 220 described herein. It will be appreciated that the attachment element 252 can be selectively attached and decoupled from the second member 236 in any suitable manner such as, for example, with a threaded engagement, a snap fit, and friction fit, a user-accessible locking mechanism, or the like.

The second member 236 can include a plunger seal 254 that can form a friction fit with the inner surface of the walls defining the inner volume 222 when the actuator mechanism 214 is disposed within the housing 212. Similarly stated, the plunger seal 254 can define a fluidic seal with the inner surface of the walls defining the inner volume 222 such that a portion of the inner volume 222 distal of the plunger seal 254 is fluidically isolated from a portion of the inner volume 222 proximal of the plunger seal 254. The plunger seal 254 can define a channel 256 that that can extend through a distal end and a proximal end of the plunger seal 254. A portion of an inner set of walls defining the channel 256 can accept a valve seat 258. In this manner, a portion of the channel 256 can receive a valve 260 that can be in contact with the valve seat 258. The valve 260 can include a threaded proximal end 262 that can selectively engage the attachment element 252 of the first member 234 as described herein.

The valve 260 can be any suitable valve. For example, in some embodiments, the valve 260 can be a one-way check valve to allow a flow of a fluid from a proximal end of the valve 260 to a distal end of the valve 260, but substantially not allow a flow of the fluid from the distal end to the proximal end. The valve 260 can be disposed within the channel 256 and can be in contact with the valve seat 258 such that the valve 260 forms a substantially fluid tight seal with the walls defining the channel 256. In some embodiments, the valve 260 can form a friction fit with walls defining the channel 256. In other embodiments, the valve 260 can form a threaded coupling or the like with at least a portion of the walls. The valve 260 can also include a seal member configured to engage the valve seat 258 to form at least a portion of the fluid tight seal.

As described above, the second member 236 can be movably disposed within the housing 212. More specifically, the second member 236 can be movable between the first configuration (e.g., a distal position) and the second configuration (e.g., a proximal position) to urge the plunger seal 254 proximally to create a negative pressure to draw, for example, a medicament, out of a medication vial (not shown) and into the first fluid reservoir 216. As shown in FIG. 14, to urge the plunger seal 254 proximally, a locking mechanism 279 can be engaged with the syringe body 238 to at least temporarily couple the plunger 244 and the syringe body 238, such that urging the plunger proximally correspondingly moves the syringe body 238 and the plunger seal 254 proximally. The locking mechanism 279 can prevent the plunger 244 from moving proximally and laterally relative to the syringe body 238 such that the second fluid reservoir 218 remains substantially unaffected and static. The plunger 244 can be urged proximally to a pre-set, predetermined, or user determined volume, where the second position can include retaining a desirable amount of a fluid (e.g., a medicament or biologic) in the first fluid reservoir 216. In the second position, as shown in FIG. 14, the transfer device 210 can be in a configuration ready to deliver the contents of the first fluid reservoir 216 and subsequently the contents of the second fluid reservoir 218 to the patient.

It will be appreciated that the any suitable locking mechanism 279 is contemplated. As illustrated, it may be desirable to prevent relative movement between the plunger 244 and the syringe body 238 in both the proximal and distal direction until the fluid in the first fluid reservoir 216 has drawn (e.g., from a medicament vial) and then fully dispensed (e.g., into a patient's line). The locking mechanism 279 can include a radial projection 280 that can be pivotable radially outward about a pin 285, where the pin 285 can be at least partially retained by an aperture 283 defined by the plunger shaft 248. In a first locked position, the radial projection can be pivoted outward such that it is substantially perpendicular to the axis of motion of the plunger 244. The radial projection 280 can include a pin 285 that can engage a catch 287 or aperture defined by the syringe body 238 when the locking mechanism 279 is in the locked position. As shown in FIG. 14, in the closed position, the pin 285 engaged with the catch 287 can result in proximal movement of the syringe body 238 when the plunger 244 is correspondingly moved in the proximal direction. Temporarily coupling the plunger 244 and the syringe body in the proximal direction can allow for translation of the plunger 244 to draw the plunger seal 254 proximally to draw medicament, or the like, into the first fluid reservoir 216. It will be appreciated that the features of the locking mechanism 279, including the pin 285 and catch 287, are described by way of example only, where any suitable stop, clasp, engagement, coupling, or the like is contemplated.

The transfer device 210 can be transitioned between the second configuration (e.g., the proximal position) and a third configuration (e.g., the distal position) to urge the plunger seal 254 distally to create a create positive pressure to urge, for example, a medicament out of the first fluid reservoir 216. As shown in FIG. 15, the radial projection 280 of the locking mechanism 279 can define a cutout or stop 284 that can engage the proximal surface 281 of the syringe body 238. As shown in FIG. 15, in the closed position, the locking mechanism 279 will result in distal movement of the plunger 244 correspondingly moving the syringe body 238 in the distal direction. In this manner the locking mechanism 279 can help insure that the fluid in the first fluid reservoir 216 is expelled before the fluid in the second fluid reservoir 218 is expelled.

The transfer device 210 can be transitioned between the third configuration and a fourth configuration to urge the plunger seal 240 distally to create a create positive pressure to urge, for example, a saline flush out of the second fluid reservoir 218. As shown in FIG. 16, after the plunger 244 has been depressed to expel the fluid from the first fluid reservoir 216, the radial projection 280 can be pivoted, for example, about 90 degrees, such that the radial projection 280 is substantially parallel to the axis of motion of the plunger 244. In this "open" position, as illustrated in FIG. 16, the radial projection 280 does not interfere with the proximal surface 281 of the syringe body 238, where the radial projection 280 can now can now pass within the syringe body 238. In use, after the fluid has been dispensed from the first fluid reservoir 216, the locking mechanism 279 can be "opened" or transitioned to the second position such that the plunger 244 can be depressed to expel fluid from the second fluid reservoir 218.

FIGS. 17-23 illustrate a syringe-based transfer device 310, where the transfer device 310 can include a pre-filled saline or flush fluid, according to an embodiment. It may be beneficial to provide a syringe having a pre-filled or predetermined amount of a fluid, such as a 10 ml or 20 ml saline flush, to which a standard syringe can be attached for the delivery of a medicine. It may also be beneficial to provide a system, such as with transfer device 310, where a first flush can be provided, followed by delivery of a medicine, which can then be followed by a second flush, all of which can be performed with a single or integrated unit or system. Providing such a three step delivery system in a single unit can save the clinician from performing multiple additional steps (e.g., screwing and unscrewing various components) to accomplish the same goal. Minimizing the number of such steps may be beneficial when giving medications through a central venous catheter, where instead of three cap entries, there may only be one. Such systems may save time and increase compliance of flushing a line before and after medications. In regards to neonates and pediatrics, such systems can increase the efficacy of life saving medications by advancing the medication to the central compartment where the medication is most effective. Having a flush/push/flush process can help assure that the line is patent before administering medications without having to first attach a separate flush device. Such systems may be useful with a wide range of medications, such as valium, where providing an initial flush may prevent the medication from crystalizing within a catheter due to a high tendency for incompatibility with other medications and Intravenous fluids. Many times patients will have to undergo unnecessary surgeries to repair or replace lines that have been crystalized and, because Valium is generally given on every oncology unit for nausea, it may be beneficial to mitigate this risk.

The syringe-based transfer device 310 (also referred to herein as "fluid transfer device," "transfer device", "integrated flush device," or "drug delivery device") includes a housing 312 and an actuator mechanism 314. The transfer device 310 can, in a pre-use configuration, include a first fluid reservoir 316 (also referred to herein as "first reservoir" or "flush reservoir") and a plunger 344. The transfer device 310 can be any suitable shape, size, or configuration. For example, while shown in FIGS. 17 and 18 as being substantially cylindrical, the transfer device 310 can be square, rectangular, polygonal, and/or any other non-cylindrical shape.

Figure 17:
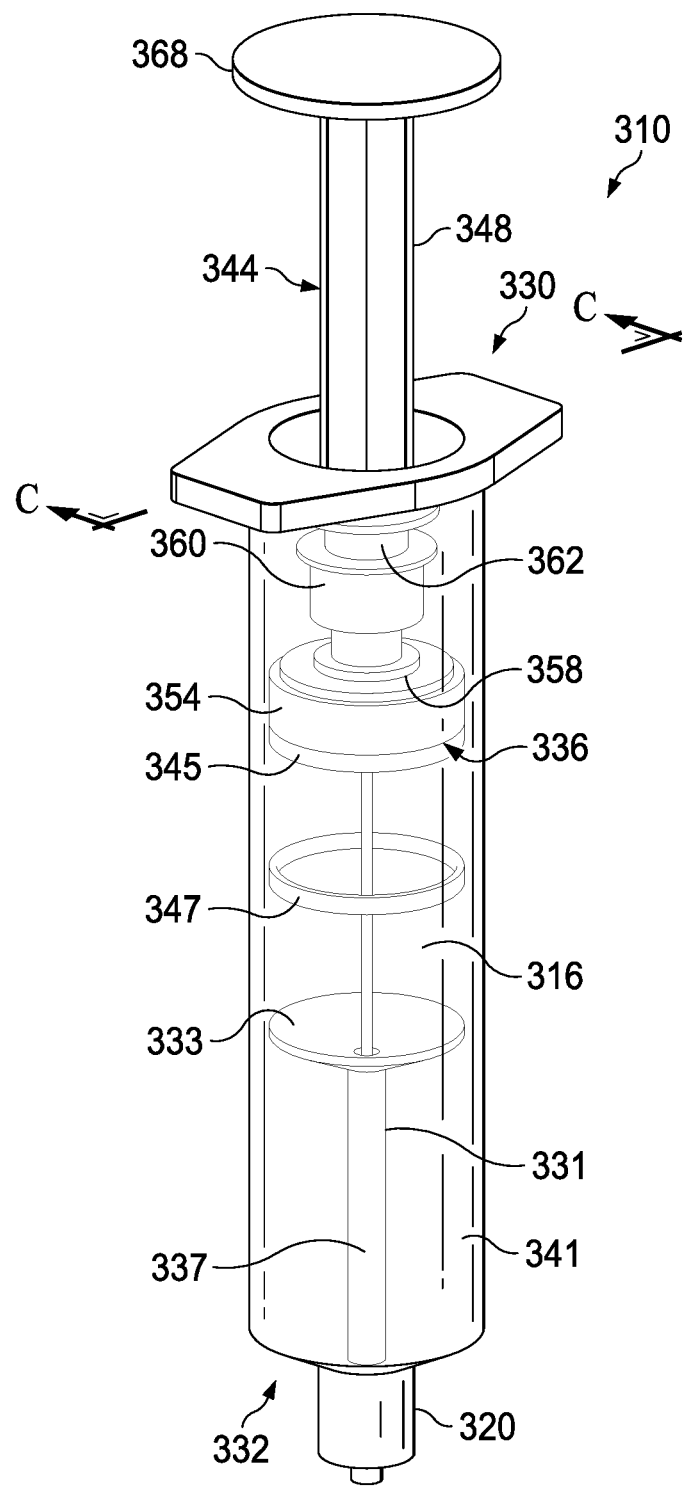
FIG. 17 depicts a perspective view of a syringe-based delivery device according to an alternate embodiment.
Figure 18:
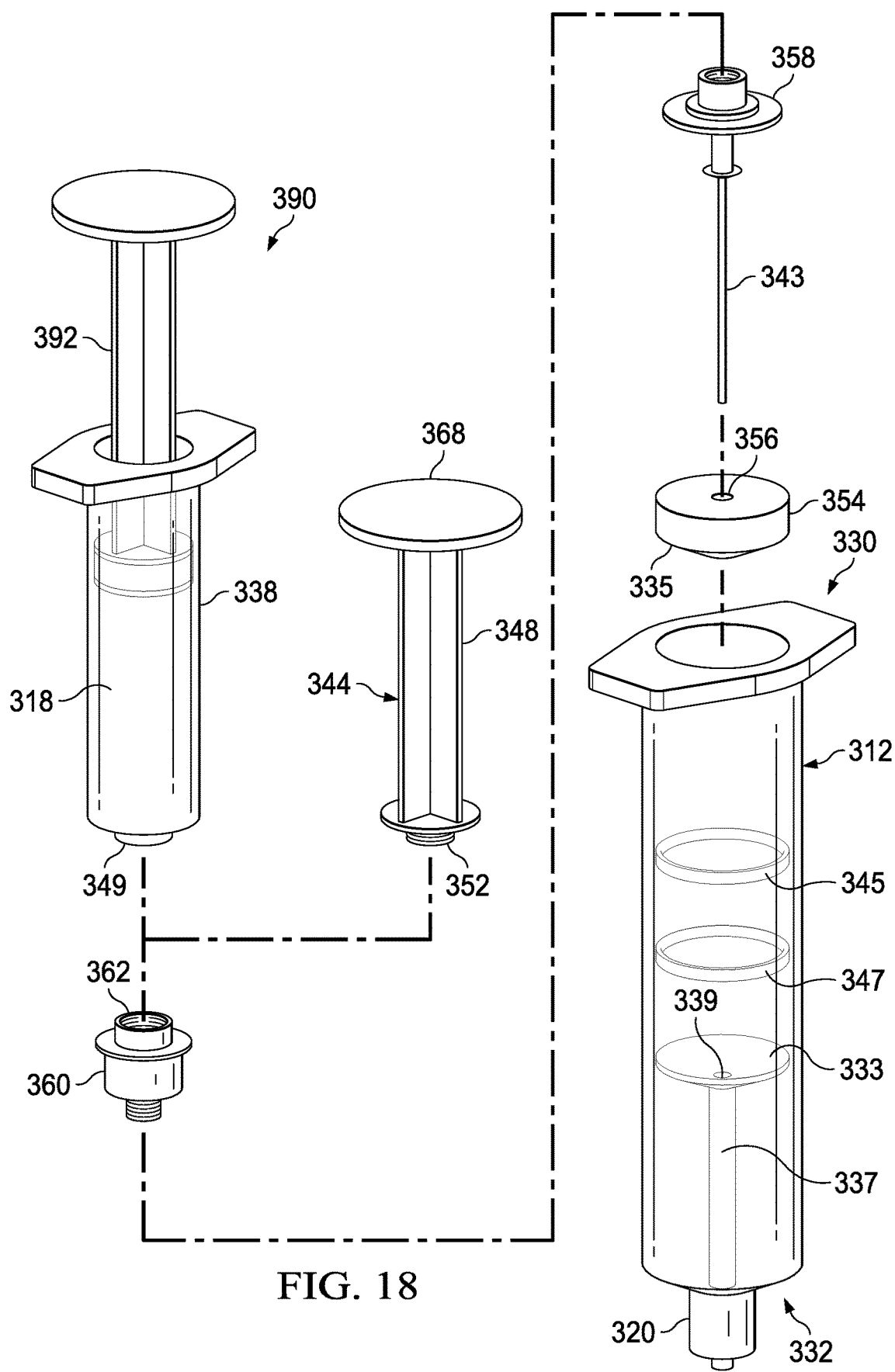
FIG. 18 depicts an exploded view of the syringe-based delivery device shown in FIG. 17.

As shown in FIGS. 17 and 18, the housing 312 can include a proximal end portion 330 and a distal end portion 332 and can define an inner volume 322 therebetween. In some embodiments, the housing 312 can be substantially similar to a syringe body. The proximal end portion 330 of the housing 312 can be substantially open and can be configured to receive at least a portion of the actuator mechanism 314, such as the plunger 344 in the pre-use configuration, such that at least the portion of the actuator mechanism 314 can be movably disposed within the inner volume 322. Furthermore, the inner volume 322 can be configured to define the first fluid reservoir 316, as further described herein.

The housing 312 can include a partitioning assembly 331, abutment assembly, or the like, positioned at about the distal end portion 332 of the housing 312. The partitioning assembly 331 can include a concave disk 333, or a substantially disk-shaped feature or abutment, that can be shaped to correspond substantially to a distal end 335 of a plunger seal 354 of the actuator mechanism 314, as will be described in more detail herein. The concave disk 333 can function as a bulkhead and can be attached to, or can be monolithically formed as a unitary, one piece construction with the housing 312. The concave disk 333 can be monolithically formed, such as in a unitary, one piece construction, with a cylinder 337 defining a lumen 339. In one embodiment, the lumen 339 can be 14 gauge and can be fluidically coupled with the first fluid reservoir 316. The concave disk 333, the cylinder 337, and the housing 312 can cooperate to define a cavity 341 that can be sealed and can be dead space. It will be appreciated that the concave disk 333 or abutment can have any suitable shape, position, or configuration.

The distal end portion 332 of the housing 312 can include a port 320. In some embodiments, the port 320 can be monolithically formed with the housing 312 (e.g., as shown in FIGS. 17 and 18) and/or the cylinder 337. The port 320 can be fluidically coupled with the lumen 339 defined by the cylinder 337. In other embodiments, the port 320 can be coupled to the distal end portion 332 in any suitable manner such as, for example, via a friction fit, a threaded coupling, a mechanical fastener, an adhesive, any number of mating recesses, and/or any combination thereof. The port 320 can be any suitable shape, size, or configuration. For example, in some embodiments, at least a portion of the port 320 can form a lock mechanism configured to be physically and fluidically coupled to a peripheral IV line, a Central Venous Catheter (CVC) line, a needle, a cannula, or other lumen-containing device. For example, in some embodiments, the port 320 can be a LUER-LOK, SLIP-TIP, or similar locking mechanism, attachment mechanism, or the like, that can be configured to physically and fluidically couple to a CVC line (not shown). In other embodiments, the port 320 can be monolithically formed in a unitary, one piece construction with at least a portion of the lumen-containing device. In this manner, the port 320 can be placed in fluid communication with a lumen defined by the lumen-defining device and to receive the bodily-fluid from a patient when the lumen-defining device is disposed within the patient.

The actuator mechanism 314 can be disposed within the inner volume 322 and can be movable between a first configuration (e.g., a proximal position relative to the housing 312, shown in FIG. 19) and a second configuration (e.g., a more distal position relative to the housing 312, shown in FIG. 20). The movement of the actuator mechanism 314 relative to the housing 312 can move the transfer device 310 between a number of different configurations and positions, as further described herein. The actuator mechanism 314, in the first and second configuration, can include the plunger 344, which can be detachable. The distal end portion 332 of the plunger 344 can include an attachment element 352, such as a LUER-LOK or similar locking or coupling mechanism, that can be configured to selectively couple with a plunger assembly 336. The attachment element 352 can be threadedly engaged with the plunger assembly 336 such that rotation of the plunger 344 (e.g., 90 degrees in a clockwise direction) will disengage the plunger 344 from the plunger assembly 336. It will be appreciated that the plunger 344 can be selectively attached and decoupled from the plunger assembly 336 in any suitable manner such as, for example, with a threaded engagement, a snap fit, and friction fit, a user-accessible locking mechanism, or the like.

The plunger assembly 336 (FIG. 17) can include a plunger seal 354 that can form a friction fit with the inner surface of the walls defining the inner volume 322 when the actuator mechanism 314 is disposed within the housing 312. Similarly stated, the plunger seal 354 can define a fluidic seal with the inner surface of the walls defining the inner volume 322 such that a portion of the inner volume 322 distal of the plunger seal 354 is fluidically isolated from a portion of the inner volume 322 proximal of the plunger seal 354. The plunger seal 354 can define a channel 356 that that can extend through a distal end and a proximal end of the plunger seal 354. A portion of an inner set of walls defining the channel 356 can accept a valve seat 358, where the valve seat can have a cannula 343 extending from the valve seat 358, through the channel 356, and distally from the distal end of the plunger seal 354. The plunger seal 354 can receive a valve 360 that can be in contact with the valve seat 358. The valve 360 can include a proximal threaded end 362 that can selectively engage the attachment element 352 of the plunger 344 during the first and second positions.

The valve 360 can be any suitable valve. For example, in some embodiments, the valve 360 can be a one-way check valve to allow a flow of a fluid from a proximal end of the valve 360 to a distal end of the valve 360, but substantially not allow a flow of the fluid from the distal end to the proximal end. The valve 360 can be disposed within the channel 356 and can be in contact with the valve seat 358 such that the valve 360 forms a substantially fluid tight seal with the walls defining the channel 356. In some embodiments, the valve 360 can form a friction fit with walls defining the channel 356. In other embodiments, the valve 360 can form a threaded coupling or the like with at least a portion of the walls. The valve 360 can also include a seal member configured to engage the valve seat 358 to form at least a portion of the fluid tight seal. The cannula 343 can have any suitable length such as, for example, from about 10 mm to about 20 mm, from about 5 mm to about 25 mm, from about 5 mm to about 10 mm, or any other suitable combination or fraction thereof.

The plunger assembly 336 can be movably disposed within the housing 312. More specifically, the plunger assembly 336 can be movable between a first position (e.g., a proximal position) and a second position (e.g., a more distal position) to urge the plunger seal 354 distally to create a positive pressure to urge, for example, a first amount of flush fluid out of the first fluid reservoir 316. Displacing the plunger 344 distally can urge the plunger seal 354 distally such that a first amount of fluid is pushed out of the first fluid reservoir 316, through the lumen defined by the cylinder 337, and out the port 320. The plunger 344 can be urged proximally to a pre-set, predetermined, or user determined volume, where the second position can include delivering a first amount of fluid (e.g., 5 ml of saline) the first fluid reservoir 316. In the second position, the transfer device 310 can have dispelled a portion of the contents of the first fluid reservoir 316 such as, for example, about 50 percent, from about 25 percent to about 75 percent, from about 10 percent to about 50 percent, or any fraction thereof. Transitioning the transfer device from the first position to the second position can deliver a first flush amount of a first type of fluid, such as a 5 ml flush of saline, which may be desirable to administer to a patient before delivering a bolus amount of a second type of fluid, such as a medication, for example.

In certain embodiments, it may be beneficial to prime or dispense a small amount of flush fluid from the first fluid reservoir 316 before delivering the first amount of flush fluid to the patient. In such embodiments the first fluid reservoir 316 can be pre-filled with an amount of fluid, such as 10.5 ml of saline, where 0.5 ml of the fluid is intended to be used to prime the transfer device 310. To accurately deliver only the appropriate amount of priming fluid, where delivering too much fluid may accidentally expel fluid associated with the flush, as will be described in more detail herein, the housing can include a first annular band 345 that can create an interference fit with the plunger seal 354. The first annular band 345 can project inwardly into the inner volume 322 defined by the housing, where the first annular band 345 can be sized to temporarily restrict distal movement of the plunger seal 354, but where the interference fit between the plunger seal 354 and the first annular band 345 can easily be defeated. In a pre-used configuration, where priming is desirable, the plunger seal 354 can be positioned just proximal to the first annular band 345 such that the first fluid reservoir 316 contains a desirable flush amount of fluid and a desirable priming amount of fluid. The plunger seal 354 can be advanced by depressing the plunger 344 until the plunger seal engages the first annular band 345 in an interference fit. This can be sized such that when the user encounters the interference fit they can easily recognize that the proper amount of priming fluid has been dispensed.

In accordance with transitioning the transfer device 310 from the first position to the second position, to deliver the first amount of flush fluid the plunger 344 can be advanced farther distally such that the interference fit is overcome. The plunger 344 can be depressed until a second interference between the plunger seal 354 and a second annular band 347 indicates that the appropriate volume of a first fluid (e.g., 5 ml) has been delivered. Transitioning the transfer device 310 from the first position to the second position can also distally translate the cannula 343 such that the cannula 343 advances within the lumen 339 defined by the cylinder 337. In the second configuration, the cannula 343 can be positioned sufficiently proximate the port 320 that fluid delivered through the cannula 343 will pass out of the port 320 and into a patient and/or lumen-defining device. The cannula 343 can advance, for example, from about 5 mm to about 10 mm, from about 3 mm to about 12 mm, from about 1 mm to about 15 mm, or any fractional distance thereof during the transition from the first configuration to the second configuration. Providing a first fluid flush in accordance with the transition from the first configuration to the second configuration can deliver a sufficient amount of flush fluid (e.g., 5 ml of saline) to clear a lumen-defining device of a patient (e.g., a CVC line).

With reference to FIG. 21, the transfer device 310 can be transitioned from the second configuration to a third configuration by selectively removing the plunger 344. In one embodiment, the plunger 344 can be removed by unthreading the attachment element 352 from the proximal threaded end 362 of the valve 360. The plunger 344 can be discarded after being removed from the transfer device 310. In one embodiment, providing the transfer device 310 with the plunger 344 during shipment and prior to use can also function to keep the valve 360 substantially sterile and/or free of contaminants. The transfer device 310 can further be transitioned from the second configuration to the third configuration by selectively attaching a syringe 390. The syringe 390 can have a syringe body 338 that can define a second fluid reservoir 318. Syringe body 338 can include a plunger 392 that can translate distally within the syringe body 338 to expel the fluid from the second fluid reservoir 318. Any suitable fluid, such as a pre-filled amount of a medicament or biologic, can be used to fill the second fluid reservoir 318. The syringe body 338 can include a port 349, which can be similar in construction and operation to port 320, at a distal end thereof. The port 349 can include a LUER-LOK, or any other suitable attachment mechanism. The syringe body 338 can be fluidly coupled to the plunger assembly 336 by threadedly engaging the port 349 with the proximal threaded end 362 of the valve 360.

As shown in FIG. 22, the transfer device 310 can be transitioned from the third configuration to a fourth configuration by depressing the plunger 392 such that the fluid retained within the second fluid reservoir 318 is expelled through the port 349. The port 349 and the plunger assembly 336 can be fluidically coupled such that fluid passes out of the second fluid reservoir 318, through the valve 360, through the cannula 343, and out through the port 320 into the patient. The syringe 390 can be any suitable syringe, such as a pre-filled syringe or a syringe drawn by a clinician to contain a desirable amount of a fluid. The second fluid reservoir 318 can contain any suitable medication or biologic such as, for example, atropine, etomidate, rocuronium, succinylcholine, epinephrine, NARCAN, amiodarone, or the like. The second fluid reservoir 318 can contain any suitable volume of fluid such as, for example, from about 0.1 ml to about 3.0 ml. In still other embodiments, the second fluid reservoir 318 can contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. Providing the delivery of a medication or biologic after a first fluid flush may effectively clear the patient's line and/or minimize the chance that the medication will interact with undesirable fluids or materials present in the patient's line.

Figure 23:
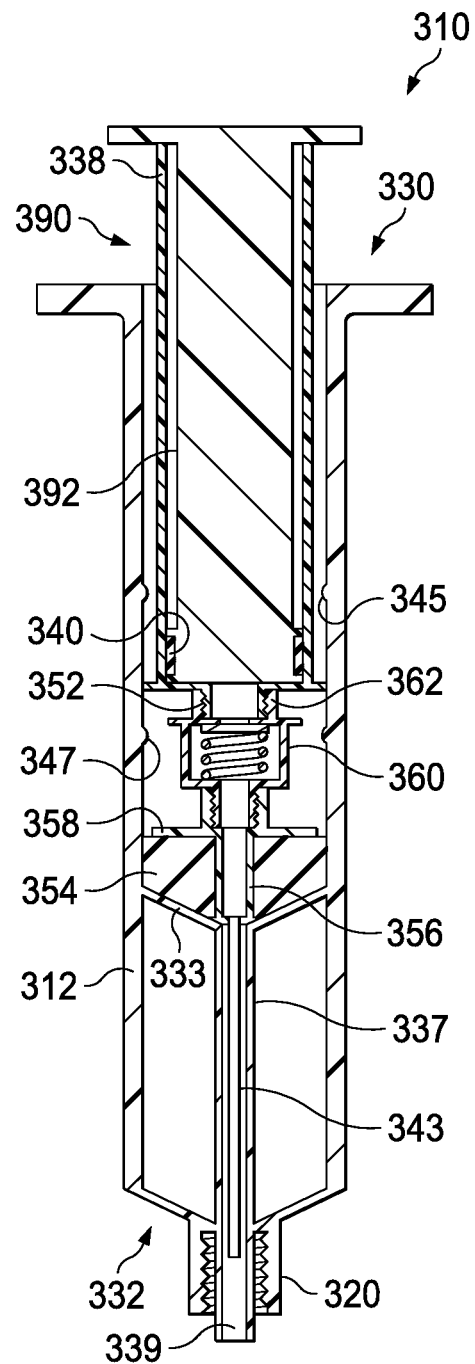
FIG. 23 depicts a cross-sectional view of the syringe-based delivery device of FIG. 17, shown with the syringe urged distally to urge a second amount of fluid from the first fluid reservoir.

The transfer device 310 can be transitioned between the fourth position to a fifth position to urge the plunger seal 354 distally to create a create positive pressure to urge, for example, a second amount of fluid out of the first fluid reservoir 316. In certain embodiments, the syringe 390 can function as the plunger in place of the removed plunger 344, where distally advancing the syringe 390 can concurrently translate the plunger assembly 336 distally. As shown in FIG. 23, after the plunger 392 has been depressed to expel the fluid from the second fluid reservoir 318, continually depressing the plunger 392 and/or syringe 390 can actuate the plunger seal 354 distally until it is seated against a proximal surface of the concave disk 333. The distal end 335 of the plunger seal 354 can substantially match the shape of the concave disk 333 such that substantially all of the fluid is expelled from the first fluid reservoir 316. Delivering a second amount of fluid in a second flush can urge the medication or other fluid administered from the first fluid reservoir 316 farther along the attached lumen-defining device (e.g., a CVC line).

In one example, the first fluid reservoir 316 of the transfer device 310 can be filled with 10.5 ml of saline. The plunger 344 can be distally actuated to prime the transfer device by expelling 0.5 ml of saline from the first fluid reservoir. The port 320 of the transfer device 310 can then be engaged with a CVC line of a patient. The plunger 344 can then be depressed to deliver a first 5 ml amount of saline to flush the CVC line. The plunger 344 can be threadedly disengaged from the plunger assembly 336 and discarded. A syringe 390 containing 1 ml of epinephrine can be threadedly engaged with the plunger assembly 336 and dispensed into the CVC line of the patient. The syringe 390 can then be advanced to deliver the second 5 ml amount of saline to flush the CVC line and to facilitate the epinephrine traveling to the heart or other desired target. It will be appreciated that any suitable volume of first flush, medicament, and second flush is contemplated. The first flush and the second flush amounts can be of the same amount, can be different amounts, can be of the same type, or can be of different types. For example, the second flush amount may include heparin in some applications. It will be appreciated that different medications may have different associated volumes and associated flush volumes. It will be appreciated that different combinations of medication and/or flush stages are contemplated including, for example, a medication followed by a first flush and then a second flush, a first flush and a second flush followed by a medication, a first flush followed by a first medication, a second flush, a second medication, and then a third flush, or the like. It will be appreciated that multiple stages including two stages, three stages, four stages, five stages, and six stages can be combined into a single syringe-based device. It will be appreciated that multiple multi-stage syringe systems can be used in combination for various procedures.

FIGS. 24-31 illustrate a syringe-based transfer device 410, where the transfer device 410 can include a pre-filled saline or flush fluid, according to an embodiment. It may be beneficial to provide a syringe having a pre-filled or predetermined amount of a fluid, such as a 10 ml or 20 ml saline flush, to which a standard syringe can be attached for the delivery of a medicine. It may also be beneficial to provide a system, such as with transfer device 410, where a first flush can be provided, followed by delivery of a medicine, which can then be followed by a second flush. The syringe-based transfer device 410 (also referred to herein as "fluid transfer device," "transfer device", "integrated flush device", or "drug delivery device") includes a housing 412 and an actuator mechanism 414. The transfer device 410 can, in a pre-use configuration, include a first fluid reservoir 416 (also referred to herein as "first reservoir" or "flush reservoir"), a plunger assembly 436, and a seal 451 or cap. The transfer device 410 can be any suitable shape, size, or configuration. For example, while shown in FIGS. 24 and 25 as being substantially cylindrical, the transfer device 410 can be square, rectangular, polygonal, and/or any other non-cylindrical shape.

Figure 25:
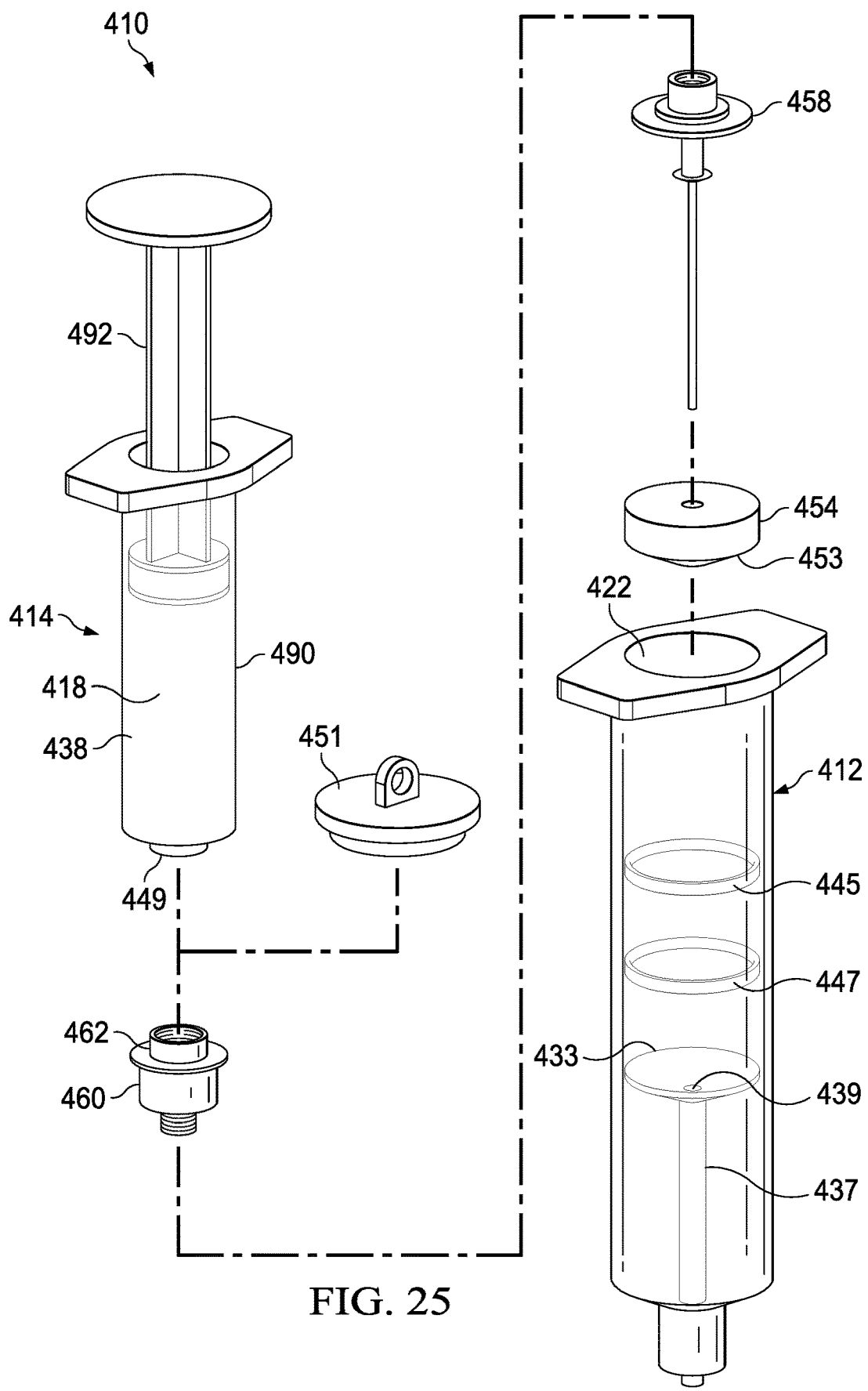
FIG. 25 depicts an exploded view of the syringe-based delivery device shown in FIG. 24.

As shown in FIGS. 25 and 26, the housing 412 can include a proximal end portion 430 and a distal end portion 432 and can define an inner volume 422 therebetween. In some embodiments, the housing 412 can be substantially similar to a syringe body. The proximal end portion 430 of the housing 412 can be open and can receive the seal 451. The seal 451 can be any suitable cap, plug, tear away foil, or the like that can maintain the inner volume 422 of the housing 412 in a sterile and/or uncontaminated state prior to use. The seal 451 can include identifying information, tamper resistant features, features to prevent the reattachment of the seal 451, or the like. As shown in FIG. 27, the seal 451 can be removed in any suitable manner such as by tearing the seal, unscrewing a cap, overcoming an interference fit, or the like.

The housing 412 can include a partitioning assembly 431 positioned at about the distal end portion 432 of the housing 412. The partitioning assembly 431 can include a concave disk 433 that can be shaped to correspond substantially to a distal end 435 of a plunger seal 454 of the actuator mechanism 414, as will be described in more detail herein. The concave disk 433 can function as a bulkhead or abutment and can be attached to, or can be monolithically formed as a unitary, one piece construction with the housing 412. The concave disk 433 can be monolithically formed, such as in a unitary, one piece construction, with a cylinder 437 defining a lumen 439. In one embodiment, the lumen 439 can be 14 gauge and can be fluidically coupled with the first fluid reservoir 416. The concave disk 433, the cylinder 437, and the housing 412 can cooperate to define a cavity 441 that can be sealed and can be dead space.

Figure 24:
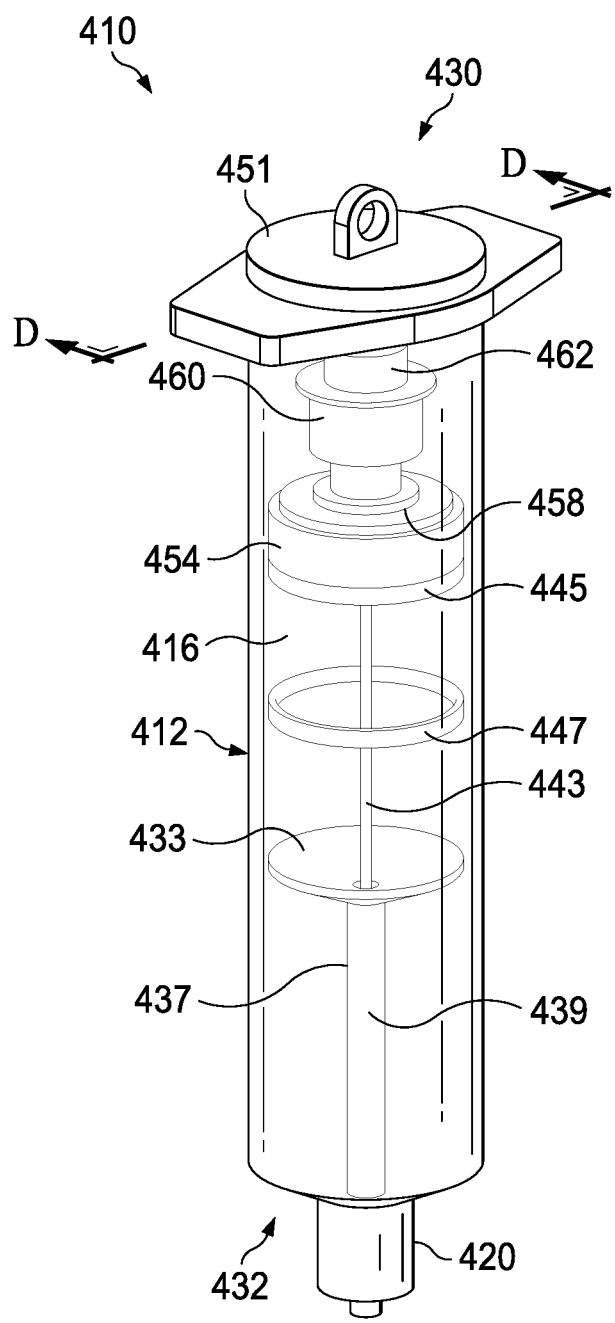
FIG. 24 depicts a perspective view of a syringe-based delivery device according to an alternate embodiment.

The distal end portion 432 of the housing 412 can include a port 420. In some embodiments, the port 420 can be monolithically formed with the housing 412 (e.g., as shown in FIGS. 24 and 25) and/or the cylinder 437. The port 420 can be fluidically coupled with the lumen 439 defined by the cylinder 437. In other embodiments, the port 420 can be coupled to the distal end portion 432 in any suitable manner such as, for example, via a friction fit, a threaded coupling, a mechanical fastener, an adhesive, any number of mating recesses, and/or any combination thereof. The port 420 can be any suitable shape, size, or configuration. For example, in some embodiments, at least a portion of the port 420 can form a lock mechanism configured to be physically and fluidically coupled to a peripheral IV line, a Central Venous Catheter (CVC) line, a needle, a cannula, or other lumen-containing device. For example, in some embodiments, the port 420 can be a LUER-LOK, SLIP-TIP, or similar locking mechanism, attachment mechanism, or the like, that can be configured to physically and fluidically couple to a CVC line (not shown). In other embodiments, the port 420 can be monolithically formed in a unitary, one piece construction with at least a portion of the lumen-containing device. In this manner, the port 420 can be placed in fluid communication with a lumen defined by the lumen-defining device and to receive the bodily-fluid from a patient when the lumen-defining device is disposed within the patient.

Figure 28:
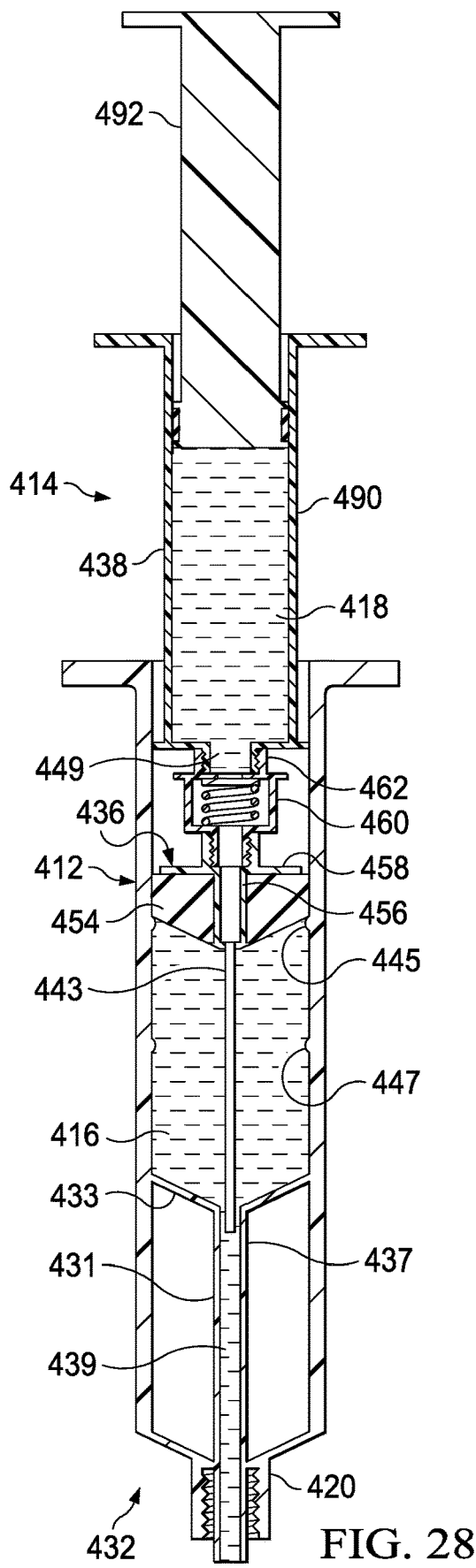
FIG. 28 depicts a cross-sectional view of the syringe-based delivery device of FIG. 24, shown with an actuator mechanism coupled with the housing of the delivery device.

The transfer device 410 can be transitioned from a first configuration (e.g., FIG. 26) to a second configuration (e.g., FIG. 27) by removing the seal 451. As shown in FIG. 28, the transfer device 410 can be transitioned from the second configuration to a third configuration by inserting at least a portion of the actuator mechanism 414 into the inner volume 422 of the housing 412. A port 449 at a distal end of the actuator mechanism 414 can be selectively engaged with the plunger assembly 436. The actuator mechanism 414 can be coupled with the plunger assembly 436 such that the actuator mechanism 414 is moveable relative to the housing 412. The movement of the actuator mechanism 414 relative to the housing 412 can move the transfer device 410 between a number of different configurations and positions, as further described herein. The distal end of the actuator mechanism 414 can include an attachment element 452, such as a LUER-LOK or similar locking or coupling mechanism, that can be configured to selectively physically and/or fluidically couple with the plunger assembly 436. The actuator mechanism 414 can be threadedly engaged with the plunger assembly 436 such that rotation of the actuator mechanism 414 (e.g., 90 degrees in a counterclockwise direction) can engage the actuator mechanism 414 with the plunger assembly 436. It will be appreciated that the actuator mechanism 414 can be selectively attached and decoupled from the plunger assembly 436 in any suitable manner such as, for example, with a threaded engagement, a snap fit, and friction fit, a user-accessible locking mechanism, or the like.

The actuator mechanism 414, in one embodiment, can include a syringe 490 that can be pre-filled with any suitable medicament, biologic, or the like. The syringe 490 can have a syringe body 438 that can define a second fluid reservoir 418. The syringe 490 can include a plunger 492 that can translate distally within the syringe body 438 to expel the fluid from the second fluid reservoir 418. Any suitable fluid, such as a pre-filled amount of a medicament or biologic, can be used to fill the second fluid reservoir 418.

The plunger assembly 436 can include a plunger seal 454 that can form a friction fit with the inner surface of the walls defining the inner volume 422. Similarly stated, the plunger seal 454 can define a fluidic seal with the inner surface of the walls defining the inner volume 422 such that a portion of the inner volume 422 distal of the plunger seal 454 is fluidically isolated from a portion of the inner volume 422 proximal of the plunger seal 454. The plunger seal 454 can define a channel 456 that that can extend through a distal end and a proximal end of the plunger seal 454. A portion of an inner set of walls defining the channel 456 can accept a valve seat 458, where the valve seat 458 can have a cannula 443 extending from the valve seat 458, through the channel 456, and distally from the distal end of the plunger seal 454. The plunger seal 454 can receive a valve 460 that can be in contact with the valve seat 458. The valve 460 can include a threaded proximal end 462 that can selectively engage the attachment element 452 of the actuator mechanism 414. In certain embodiments, as illustrated in FIG. 25, the plunger assembly 436 can be an integral component where one or a plurality of the plunger seal 454, the cannula 443, the valve seat 458, and the valve 460 can be monolithically formed such that they are of a unitary, one piece construction.

The valve 460 can be any suitable valve. For example, in some embodiments, the valve 460 can be a one-way check valve to allow a flow of a fluid from a proximal end of the valve 460 to a distal end of the valve 460, but substantially not allow a flow of the fluid from the distal end to the proximal end. The valve 460 can be disposed within the channel 456 and can be in contact with the valve seat 458 such that the valve 460 forms a substantially fluid tight seal with the walls defining the channel 456. In some embodiments, the valve 460 can form a friction fit with walls defining the channel 456. In other embodiments, the valve 460 can form a threaded coupling or the like with at least a portion of the walls. The valve 460 can also include a seal member configured to engage the valve seat 458 to form at least a portion of the fluid tight seal. The cannula 443 can have any suitable length such as, for example, from about 10 mm to about 20 mm, from about 5 mm to about 25 mm, from about 5 mm to about 10 mm, or any other suitable combination or fraction thereof.

Figure 29:
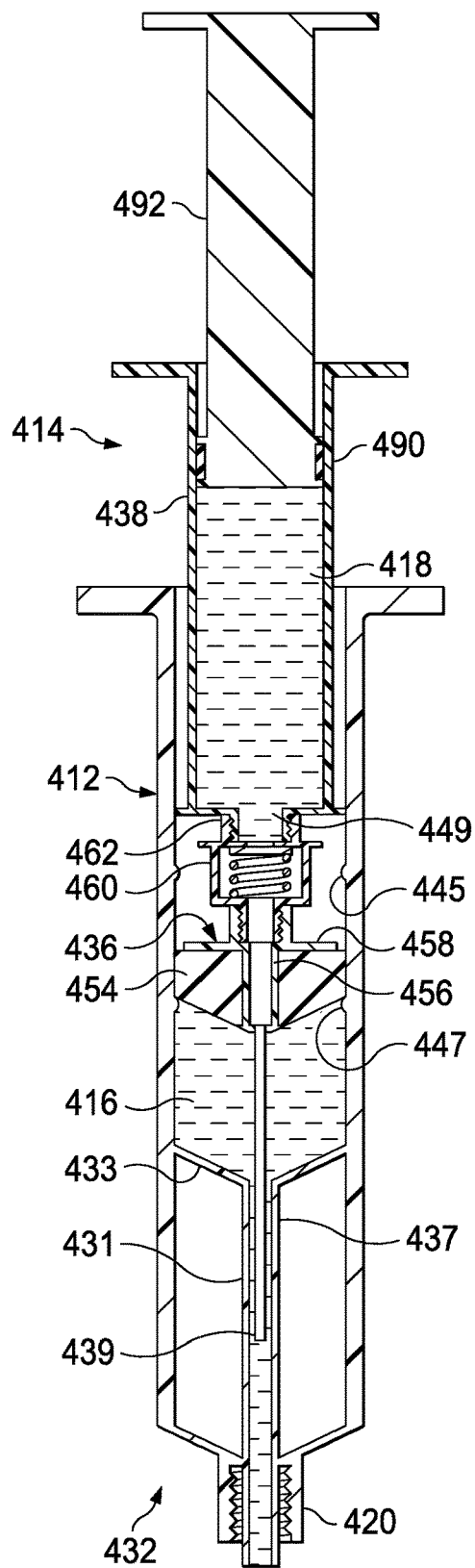
FIG. 29 depicts a cross-sectional view of the syringe-based delivery device of FIG. 24, shown with actuator mechanism moved distally to urge a first amount of fluid from a first fluid reservoir.

The plunger assembly 436 can be movably disposed within the housing 412 to transition the fluid transfer device 410 from the second configuration to the third configuration. As shown in FIG. 29, the plunger assembly 436 can be movable to urge the plunger seal 454 distally to create a positive pressure to urge, for example, a first amount of flush fluid out of the first fluid reservoir 416. Displacing the actuator mechanism 414 distally can urge the plunger seal 454 distally such that a first amount of fluid is pushed out of the first fluid reservoir 416, through the lumen 439 defined by the cylinder 437, and out the port 420. The actuator mechanism 414 can be urged distally to a pre-set, predetermined, or user determined volume, where the distal actuation can include delivering a first amount of fluid (e.g., 5 ml of saline) from the first fluid reservoir 416. In the third configuration, the transfer device 410 can have expelled a portion of the contents of the first fluid reservoir 416 such as, for example, about 50 percent, from about 25 percent to about 75 percent, from about 10 percent to about 50 percent, or any fraction thereof. Transitioning the transfer device 410 from the second configuration to the third configuration can deliver a first flush amount of a first type of fluid, such as a 5 ml flush of saline, which may be desirable to administer to a patient before delivering a bolus amount of a second type of fluid, such as a medication, for example.

In certain embodiments, it may be beneficial to prime or dispense a small amount of flush fluid from the first fluid reservoir 416 before delivering the first amount of flush fluid to the patient. In such embodiments the first fluid reservoir 416 can be pre-filled with an amount of fluid, such as 10.5 ml of saline, where 0.5 ml of the fluid is intended to be used to prime the transfer device 410. To accurately deliver only the appropriate amount of priming fluid, where delivering too much fluid may accidentally expel fluid associated with the flush, as will be described in more detail herein, the housing 412 can include a first annular band 445 that can form an interference fit with the plunger seal 454. The first annular band 445 can project inwardly into the inner volume 422 defined by the housing 412, where the first annular band 445 can be sized to temporarily restrict distal movement of the plunger seal 454, but where the interference fit between the plunger seal 454 and the first annular band 445 can easily be defeated, but still provide tactile feedback to the user. In a pre-use configuration, where priming is desirable, the plunger seal 454 can be positioned just proximal to the first annular band 445 such that the first fluid reservoir 416 contains a desirable flush amount of fluid and a desirable priming amount of fluid. The plunger seal 454 can be advanced by depressing the actuator mechanism 414 until the plunger seal 454 engages the first annular band 445 in an interference fit. This can be sized such that when the user encounters the interference fit they can easily recognize that the proper amount of priming fluid has been dispensed.

In accordance with transitioning the transfer device 410 from the second configuration to the third configuration, the actuator mechanism 414 can be advanced distally to overcome the interference fit between the first annular band 445 and the plunger seal 454. The actuator mechanism 414 can be depressed until a second interference between the plunger seal 454 and a second annular band 447 indicates that the appropriate volume of a first fluid (e.g., 5 ml of saline) has been delivered. Transitioning the transfer device 410 from the second configuration to the third configuration can also distally translate the cannula 443 such that the cannula 443 advances within the lumen 439 defined by the cylinder 437. In the third configuration, as shown in FIG. 29, the cannula 443 can be positioned sufficiently proximate the port 420 that fluid delivered through the cannula 443 will pass out of the port 420 and into a patient and/or lumen-defining device. The cannula 443 can advance, for example, from about 5 mm to about 10 mm, from about 3 mm to about 12 mm, from about 1 mm to about 15 mm, or any fractional distance thereof during the transition from the second configuration to the third configuration. Providing a first fluid flush in accordance with the transition from the second configuration to the third configuration can deliver a sufficient amount of flush fluid (e.g., 5 ml of saline) to clear a lumen-defining device of a patient (e.g., a CVC line).

As shown in FIG. 30, the transfer device 410 can be transitioned from the third configuration to a fourth configuration by depressing the plunger 492 such that the fluid retained within the second fluid reservoir 418 is expelled through the port 449. The port 449 and the plunger assembly 436 can be fluidically coupled such that fluid passes out of the second fluid reservoir 418, through the valve 460, through the cannula 443, through the port 420, and into the patient and/or lumen-defining device. The syringe 490 can be any suitable syringe, such as a pre-filled syringe or a syringe drawn by a clinician to contain a desirable amount of a fluid. The second fluid reservoir 418 can contain any suitable medication or biologic such as, for example, atropine, etomidate, rocuronium, succinylcholine, epinephrine, NARCAN, amiodarone, or the like. The second fluid reservoir 418 can contain any suitable volume of fluid such as, for example, from about 0.1 ml to about 3.0 ml. In still other embodiments, the second fluid reservoir 418 can contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. Providing the delivery of a medication or biologic after a first fluid flush may effectively clear the patient's line and/or minimize the chance that the medication will interact with undesirable fluids or materials present in the patient's line.

As shown in FIG. 31, the transfer device 410 can be transitioned from the fourth configuration to a fifth configuration to urge the plunger seal 454 distally to create positive pressure to urge, for example, a second amount of fluid out of the first fluid reservoir 416. Distally advancing the syringe 490 can concurrently translate the plunger assembly 436 distally. As shown in FIG. 31, after the plunger 492 has been depressed to expel the fluid from the second fluid reservoir 418, continually depressing the plunger 492 and/or syringe 490 can actuate the plunger seal 454 distally until it is seated against a proximal surface of the concave disk 433. The distal end 435 of the plunger seal 454 can substantially match the shape of the concave disk 433 such that substantially all of the fluid is expelled from the first fluid reservoir 416. Delivering a second amount of fluid in a second flush can urge the medication or other fluid administered from the first fluid reservoir 416 farther along the attached lumen-defining device (e.g., a CVC line).

Figure 32:
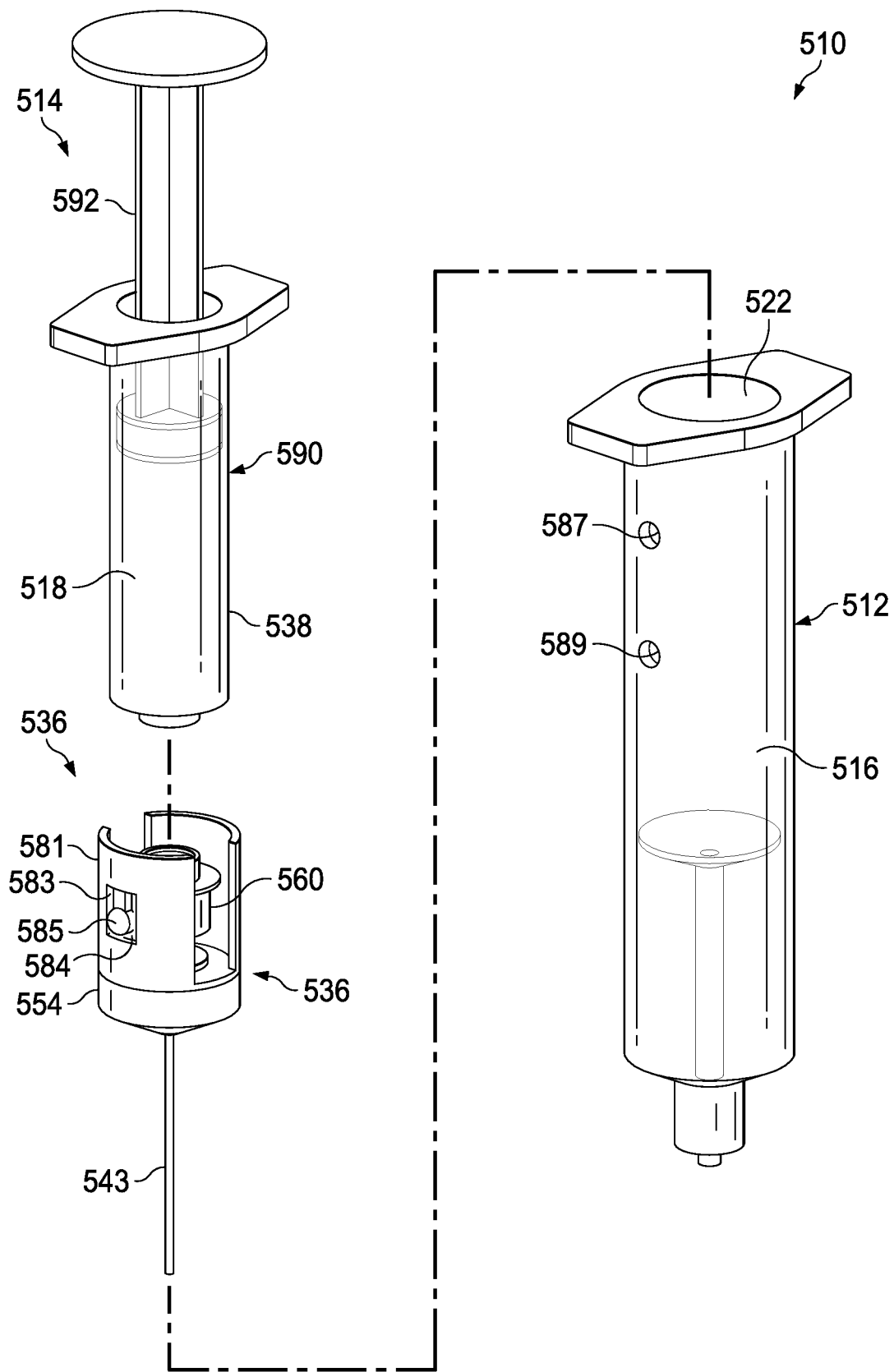
FIG. 32 depicts an exploded view of a syringe-based delivery device according to an alternate embodiment.

FIG. 32 illustrates a syringe-based transfer device 510, where the transfer device 510 can include an alternate locking mechanism 579 according to an embodiment. The operation of the transfer device 510 can be the same or substantially similar to the operation of transfer device 410, as described herein. It may be determined that a robust locking mechanism 579 may be beneficial to provide a clinician with clear guidance on when the transfer device 510 is primed, when the first portion of flush fluid has been delivered, and an additional assurance that the second amount of fluid flush will not be delivered until after the medication has been delivered. As described herein, it may be beneficial to provide a system, such transfer device 510, where a first flush can be provided, followed by delivery of a medicine, which can then be followed by a second flush. The syringe-based transfer device 510 (also referred to herein as "fluid transfer device," "transfer device", "integrated flush device", or "drug delivery device") includes a housing 512 and an actuator mechanism 514.

The actuator mechanism 514, in one embodiment, can include a syringe 590 that can be pre-filled with any suitable medicament, biologic, or the like. The syringe 590 can have a syringe body 538 that can define a second fluid reservoir 518. The syringe 590 can include a plunger 592 that can translate distally within the syringe body 538 to expel the fluid from the second fluid reservoir 518. Any suitable fluid, such as a pre-filled amount of a medicament or biologic, can be used to fill the second fluid reservoir 518.

A plunger assembly 536 can include a plunger seal 554 that can form a friction fit with the inner surface of the walls defining an inner volume 522 of a housing 512. Similarly stated, the plunger seal 554 can define a fluidic seal with the inner surface of the walls defining the inner volume 522 such that a portion of the inner volume 522 distal of the plunger seal 554 is fluidically isolated from a portion of the inner volume 522 proximal of the plunger seal 554. The plunger seal 554 can define a channel (not shown) that that can extend through a distal end and a proximal end of the plunger seal 554. A portion of an inner set of walls defining the channel can accept a valve 560, where the valve 560 can have a cannula 543 extending from the valve 560, through the channel, and distally from the distal end of the plunger seal 554. The valve 560 can be any suitable valve. For example, in some embodiments, the valve 560 can be a one-way check valve to allow a flow of a fluid from a proximal end of the valve 560 to a distal end of the valve 560, but substantially not allow a flow of the fluid from the distal end to the proximal end. The plunger assembly 536 can include at least one semi-circular projection 581 that is coupled with or monolithically formed with the plunger seal 554 such that the at least one semi-circular projection 581 extends in a generally proximal direction relative to the plunger seal 554. The at least one semi-circular projection 581 can be shaped to correspond to the walls of the housing 512. The at least one semi-circular projection 581 can define an aperture 584, where a flexible tab or living hinge 585 can be at least partially positioned within the aperture 584. The living hinge 585 can be biased radially outward and can be sufficiently flexible that a user can depress the living hinge 585 such that it will move relative to the at least one semi-circular projection 581.

The plunger assembly 536 can be movably disposed within the housing 512. More specifically, the plunger assembly 536 can be movable to urge the plunger seal 554 distally to create a positive pressure to urge, for example, a first amount of flush fluid out of the first fluid reservoir 516. The housing 512 can define a first aperture 587 and a second aperture 589, where the first aperture 587 and the second aperture 589 can be spaced apart on the same linear axis. The first aperture 587 and the second aperture 589 can be through holes that pass through housing 512. Displacing the actuator mechanism 514 distally can urge the plunger seal 554 distally such that a first amount of fluid is pushed out of the first fluid reservoir 516. When the transfer device 510 is properly primed the living hinge 585 can engage the first aperture 587 to prevent relative movement between the actuator mechanism 514 and the housing 512. Next, the actuator mechanism 514 can be freed to move distally by depressing the living hinge 585 such that the living hinge 585 disengages the first aperture 587. Simultaneous application of pressure in a distal direction to the actuator mechanism 514 can urge the plunger seal 554 distally to a pre-set, predetermined, or user determined volume, where the distal actuation can include delivering a first amount of fluid (e.g., 5 ml of saline) from the first fluid reservoir 516. When the pre-determined volume has been delivered the living hinge 585 can engage the second aperture 589 such that relative movement between the actuator mechanism 514 and the housing 512 is again prevented. In such a configuration the transfer device 510 can have expelled a portion of the contents of the first fluid reservoir 516 such as, for example, about 50 percent, from about 25 percent to about 75 percent, from about 10 percent to about 50 percent, or any fraction thereof. Providing a first fluid flush can deliver a sufficient amount of flush fluid (e.g., 5 ml of saline) to clear a lumen-defining device of a patient (e.g., a CVC line).

The transfer device 510 can be used to administer a medication or biologic, for example, by depressing the plunger 592 of the syringe 590 such that the fluid retained within the second fluid reservoir 518 is expelled. The syringe 590 can be any suitable syringe, such as a pre-filled syringe or a syringe drawn by a clinician to contain a desirable amount of a fluid. The second fluid reservoir 518 can contain any suitable medication or biologic such as, for example, atropine, etomidate, rocuronium, succinylcholine, epinephrine, NARCAN, amiodarone, or the like. Providing the delivery of a medication or biologic after a first fluid flush may effectively clear the patient's line and/or minimize the chance that the medication will interact with undesirable fluids or materials present in the patient's line. During delivery of the medication, for example, the living hinge 585 can engage the second aperture 589 to resist distal movement of the plunger seal 554 while the syringe 590 is being operated. Such a locking mechanism 579 can help insure that the medication is delivered without accidentally mixing the medication with a portion of the remaining flush in the first fluid reservoir 516.

After delivering the medication, the transfer device 510 can be transitioned to urge the plunger seal 554 distally to create a create positive pressure to urge, for example, a second amount of fluid out of the first fluid reservoir 516. To move the plunger seal 554 distally, the living hinge 585 can be depressed to decouple the actuator mechanism 514 from the housing 512 and second aperture 589. Once the living hinge 585 has been disengaged, the plunger seal 554 can be urged distally to empty the remaining fluid from within the first fluid reservoir 516. Delivering a second amount of fluid in a second flush can urge the medication or other fluid administered from the first fluid reservoir 516 farther along the attached lumen-defining device (e.g., a CVC line).

FIGS. 33-43 illustrate a syringe-based transfer device 610 according to an embodiment. Dual syringe technology can allow for the faster reconstitution of powder medications that are administered, for example, intramuscularly or intravenously. In certain embodiments, an outer glass syringe can contain a powder form of a medication with a reconstitution solution located in a separate location in the syringe-based-transfer device. One use case for the syringe-based transfer device 610 can be for the reconstitution of ziprasidone HCl (sold under the trade name GEODON®), which is an antipsychotic used to treat schizophrenia and the manic symptoms of bipolar disorder. The syringe-based transfer device 610 can be used with glucagon to treat severe hypoglycemia in diabetic patients. The syringe-based transfer device 610 can be used with ceftriaxone (sold under the trade name ROCHEPIN®), a broad spectrum antibiotic used for a variety of medical conditions such as pneumonia, unitary track infections, sexually transmitted diseases, and in veterinary applications. Reconstitution of any suitable medicament is contemplated. It will be appreciated that embodiments described herein can be used in medical and non-medical applications where, for example, such systems can be used to reconstitute any material where it is preferable to maintain the constituent parts of the material separate until shortly before use.

The syringe-based transfer device 610 (also referred to herein as "fluid transfer device," "ziprasidone HCl delivery device," or "drug delivery device") includes a housing 612 and an actuator mechanism 614. The transfer device 610 can be configured to include or define a medicament reservoir 616 and a saline reservoir 618. The transfer device 610 can be any suitable shape, size, or configuration. For example, while shown in FIG. 33 as being substantially cylindrical, the transfer device 610 can be square, rectangular, polygonal, and/or any other non-cylindrical shape.

Figure 33:
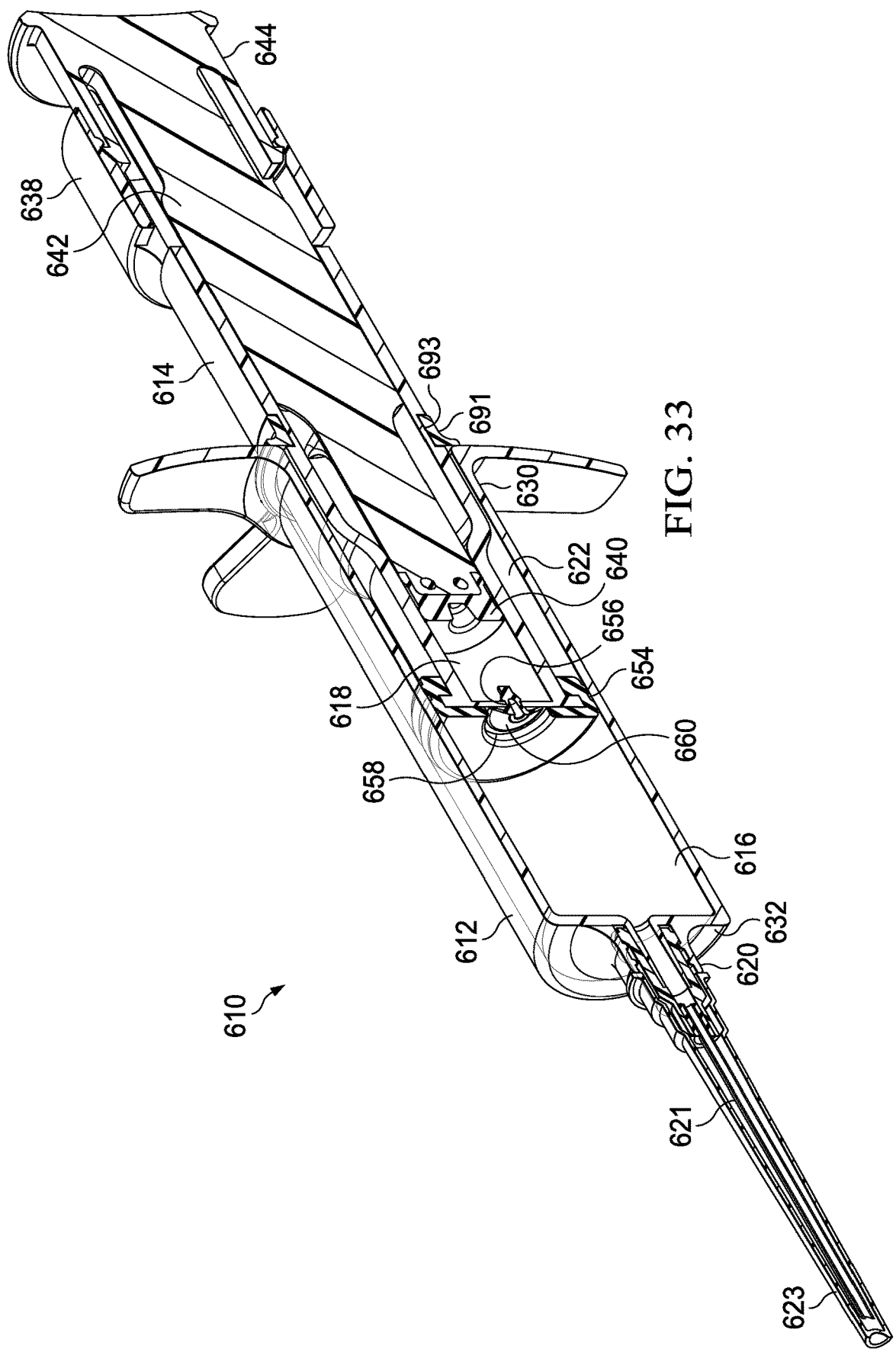
FIG. 33 depicts a longitudinal cross-sectional view of a syringe-based delivery device for reconstituted medications according to one embodiment.

As shown in FIG. 33, the housing 612 can include a proximal end portion 630 and a distal end portion 632 and can define an inner volume 622 therebetween. In some embodiments, the housing 612 can be substantially similar to a syringe body. The proximal end portion 630 of the housing 612 can be substantially open and can be configured to receive at least a portion of the actuator mechanism 614 such that at least a portion of the actuator mechanism 614 can be movably disposed within the inner volume 622. Furthermore, the inner volume 622 can be configured to define the medicament reservoir 616, as further described herein. The distal end portion 632 of the housing 612 can include a port 620. In some embodiments, the port 620 can be monolithically formed with the housing 612. In other embodiments, the port 620 can be coupled to the distal end portion 632 in any suitable manner such as, for example, via a friction fit, a threaded coupling, a mechanical fastener, an adhesive, any number of mating recesses, and/or any combination thereof. The port 620 can be any suitable shape, size, or configuration. For example, in some embodiments, the port 620 is coupled with a needle 621 having a cover 623, a cannula, or other lumen-containing device.

The actuator mechanism 614 can be disposed within the inner volume 622 and can be movable between a first position (e.g., a proximal position relative to the housing 612) and a second position (e.g., a distal position relative to the housing 612). The movement of the actuator mechanism 614 relative to the housing 612 can move the transfer device 610 between a number of different configurations and positions, as further described herein. The actuator mechanism 614 can include a plunger 644 and a syringe body 638 that can define an inner volume 642 therebetween. At least a portion of the inner volume 642 can be configured to define the saline reservoir 618, as further described herein. The plunger 644 can include a plunger seal 640 that can fluidically seal the saline reservoir 618. The syringe body 638 can include an open proximal end such that the plunger 644 can be movably disposed within the inner volume 642.

The actuator mechanism 614 can include a plunger seal 654 that can form a friction fit with the inner surface of the walls defining the inner volume 622 when the actuator mechanism 614 is disposed within the housing 612. Similarly stated, the plunger seal 654 can define a fluidic seal with the inner surface of the walls defining the inner volume 622 such that a portion of the inner volume 622 distal of the plunger seal 654 is fluidically isolated from a portion of the inner volume 622 proximal of the plunger seal 654. The plunger seal 654 can define a channel 656 that that can extend through a distal end and a proximal end of the plunger seal 654. A portion of an inner set of walls defining the channel 656 can accept a valve seat 658. In this manner, a portion of the channel 656 can receive a valve 660 that can be in contact with the valve seat 658.

The valve 660 can be any suitable valve. For example, in some embodiments, the valve 660 can be a one-way check valve to allow a flow of a fluid, such as 1.2 ml of saline, from a proximal end of the valve 660 to a distal end of the valve 660, but substantially not allow a flow of the fluid from the distal end to the proximal end. It will be appreciated that the fluid can be any volume of a reconstitution fluid such as lidocaine or the like. The valve 660 can be disposed within the channel 656 and can be in contact with the valve seat 658 such that the valve 660 forms a substantially fluid tight seal with the walls defining the channel 656. In some embodiments, the valve 660 can form a friction fit with walls defining the channel 656. In other embodiments, the valve 660 can form a threaded coupling or the like with at least a portion of the walls. The valve 660 can also include a seal member configured to engage the valve seat 658 to form at least a portion of the fluid tight seal.

As described above, the plunger 644 can be movably disposed within the syringe body 638. More specifically, the plunger 644 can be movable between a first configuration (e.g., a proximal position) and a second configuration (e.g., a distal position) to create positive pressure to urge for example, from about 1 ml to about 2 ml of saline, out of the saline reservoir 618. In this manner, the distal translation of the plunger 644 can first cause the plunger 644 to move distally to expel the fluid from the saline reservoir 618. Once the saline reservoir 618 has been emptied into the medicament reservoir 616 the fluid can combine with a medicament, such as ziprasidone HCl. Continued distal movement of the plunger 644 can continue until a proximal end of the plunger 644 abuts the proximal end of the syringe body 638. In one embodiment the plunger 644, when fully depressed, can be fixedly coupled with the syringe body 638 using any suitable locking mechanism. The actuator mechanism 614 can be prevented from moving distally relative to the housing 612 by a removable clip 691 retained in a channel 693. The removable clip 691 can be sized such that the removable clip 691 abuts the proximal end portion 630 of the housing 612, where removal of the removable clip 691 can allow the actuator mechanism to translate distally within the housing 612.

Figure 34:
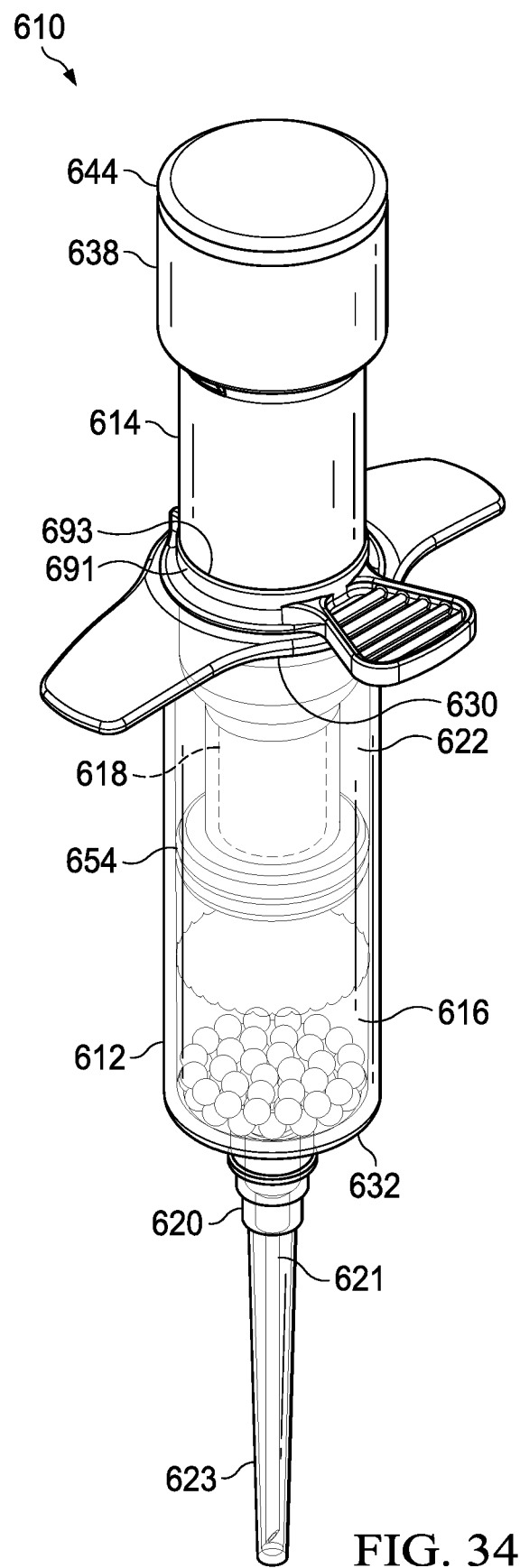
FIG. 34 depicts a side perspective view of the syringe syringe-based delivery device shown with a plunger depressed to expel a reconstitution fluid into a medicament chamber according to one embodiment.
Figure 35:
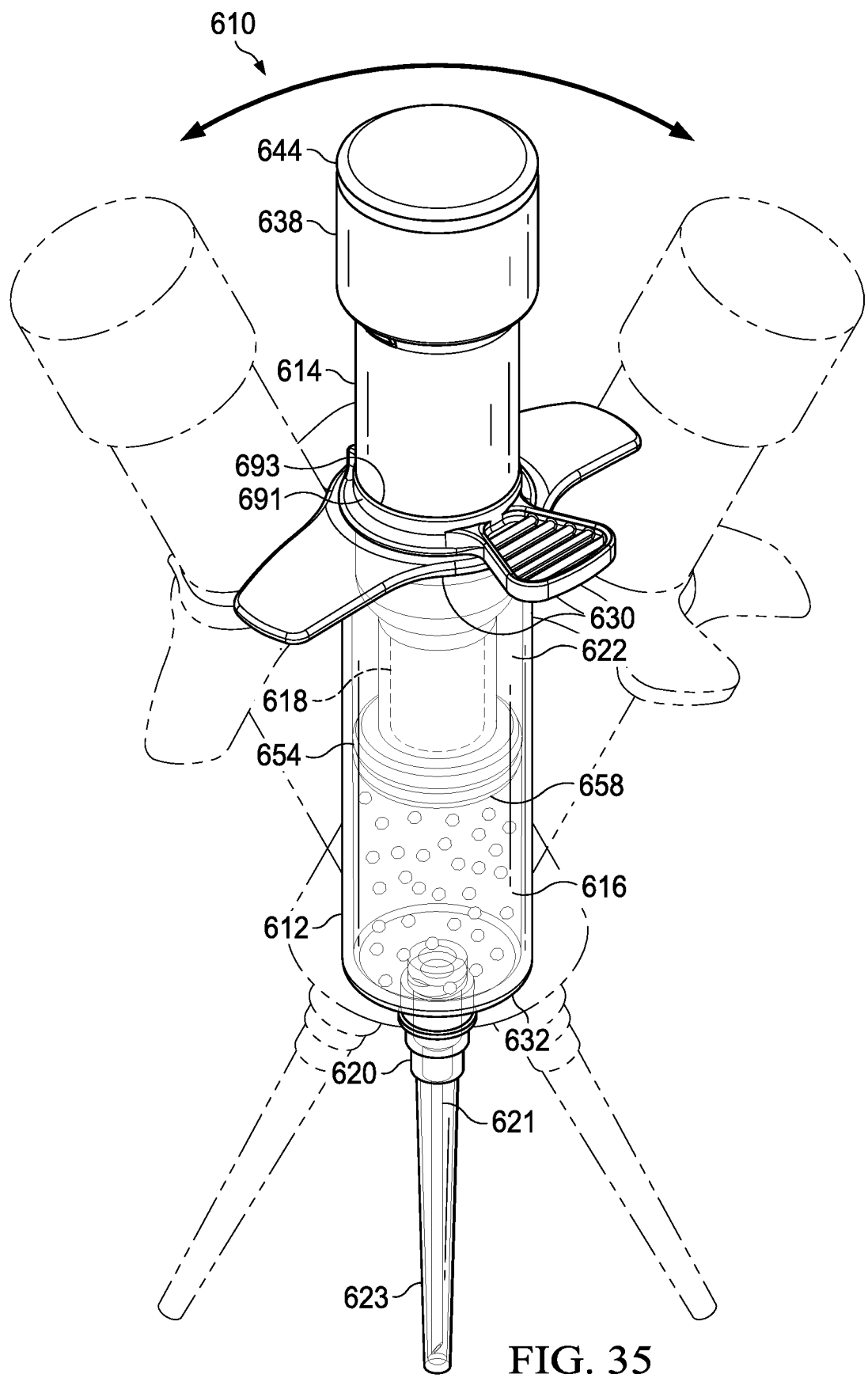
FIG. 35 depicts a side perspective view of the syringe syringe-based delivery device shown being agitated to mix the reconstitution fluid with the medicament.
Figure 36:
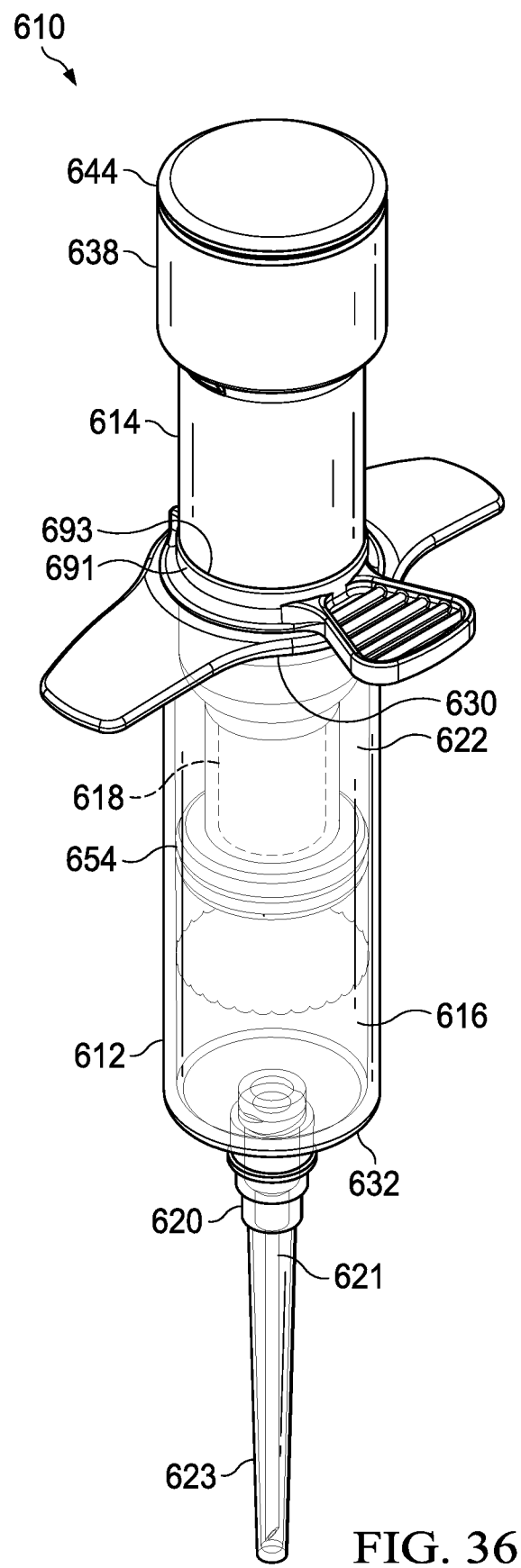
FIG. 36 depicts a side perspective view of the syringe syringe-based delivery device shown with a fully reconstituted medication retained within the medicament chamber.

In use, as shown in FIG. 34, a user can depress the plunger 644 to urge an amount of fluid, such as 1.2 ml of saline, from the saline reservoir 618 into the medicament reservoir 616. Once the fluid or saline has been combined in the medicament reservoir 616 the syringe-based transfer device 610 can be agitated as illustrated in FIG. 35. The syringe-based transfer device 610 can be shaken for a period of time, such as 30 seconds to 120 seconds, until the saline has combined with the medicament to form a substantially homogenous fluid. In one embodiment, saline or lidocaine is combined with ziprasidone HCl and is agitated manually until the medicament is fully dissolved and reconstituted as illustrated in FIG. 36. It will be appreciated that the medicament reservoir can retain any medicament, for example, in solid form such as powdered form, tablet form, pill form, crystal form, dehydrated form, pellet form, or the like.

Figure 37:
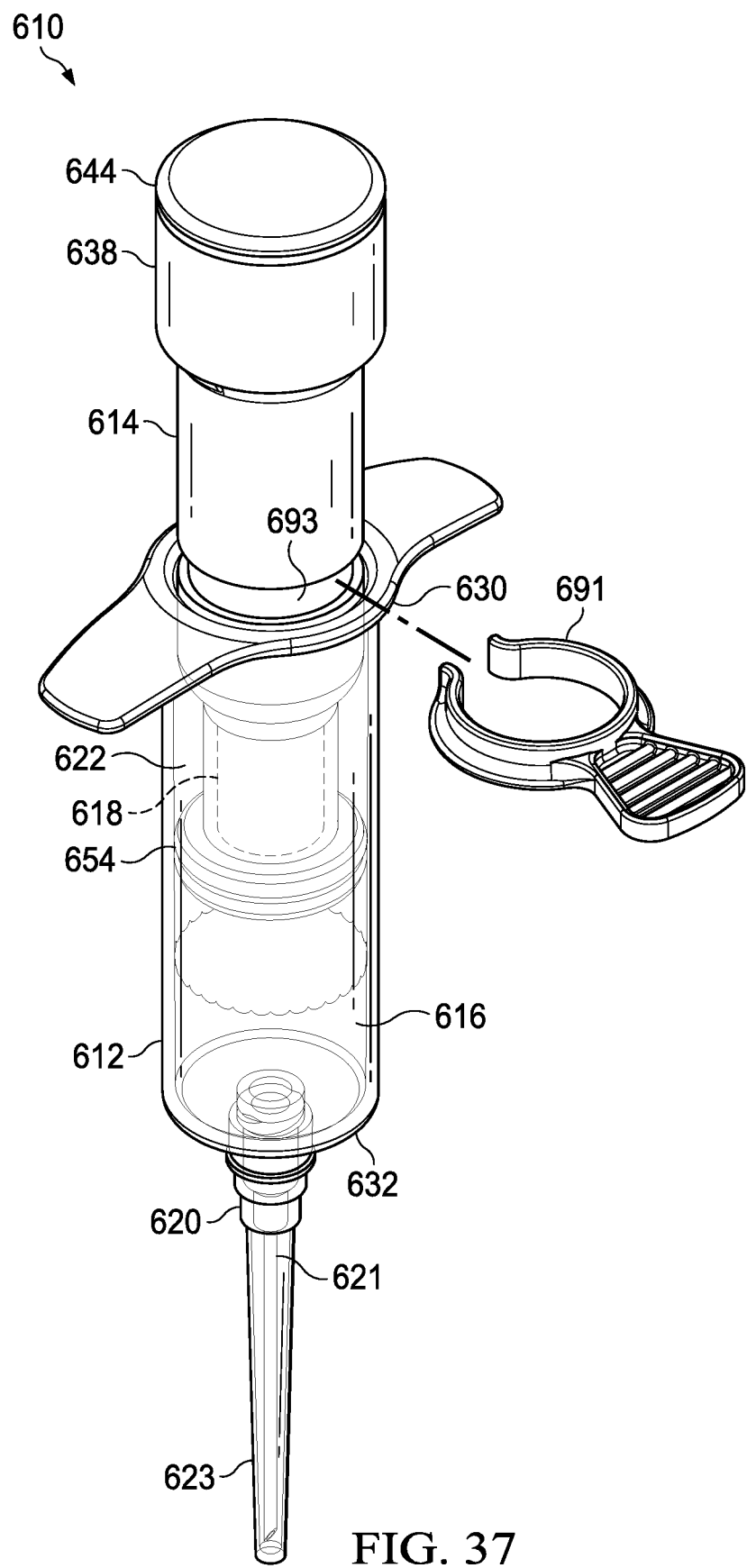
FIG. 37 depicts a side perspective view of the syringe syringe-based delivery device shown with a clip being removed from an actuator mechanism such that the actuator mechanism is distally moveable relative to the housing.
Figure 38:
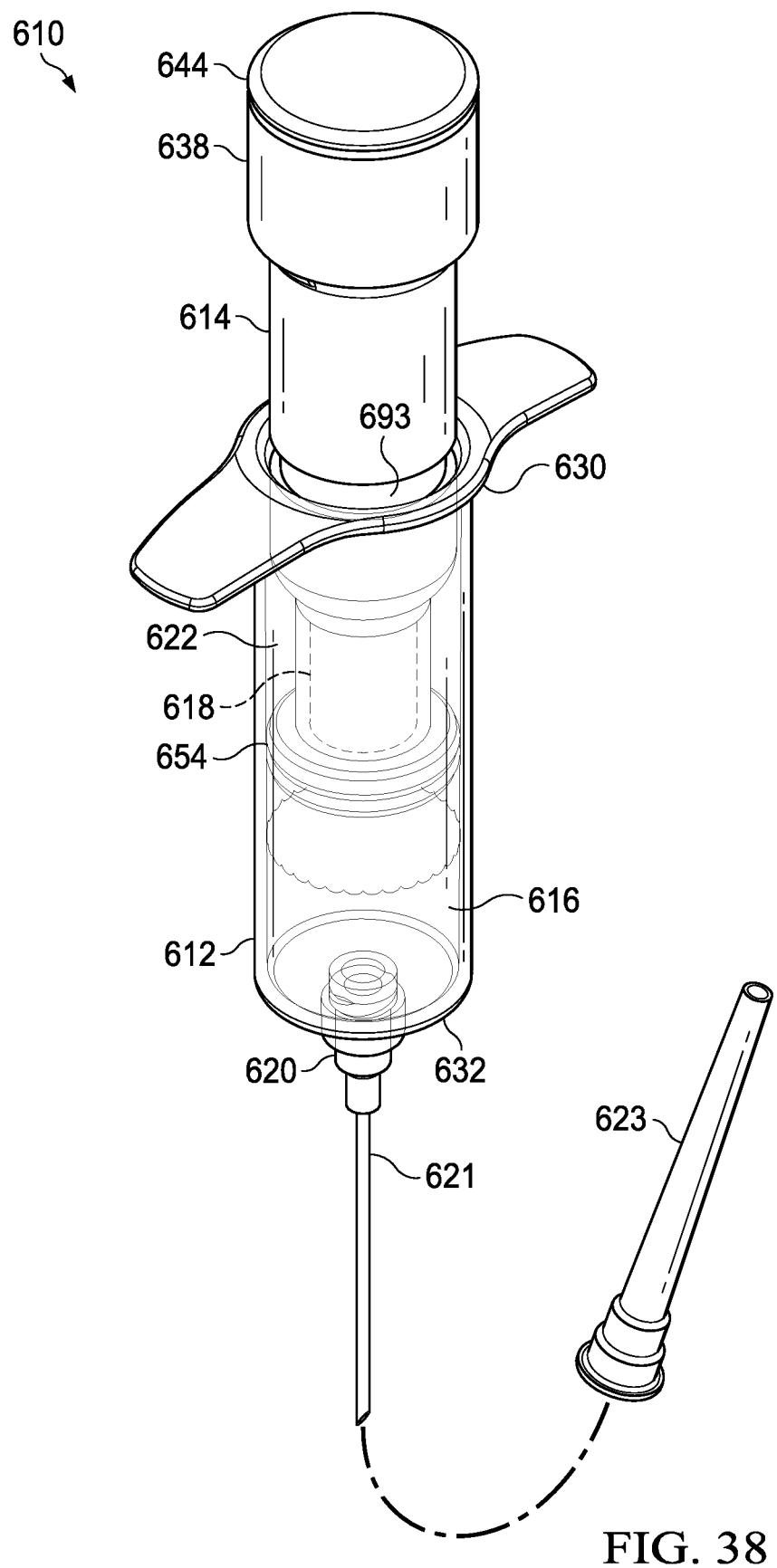
FIG. 38 depicts a side perspective view of the syringe syringe-based delivery device shown with a cap being removed to expose a needle.
Figure 39:
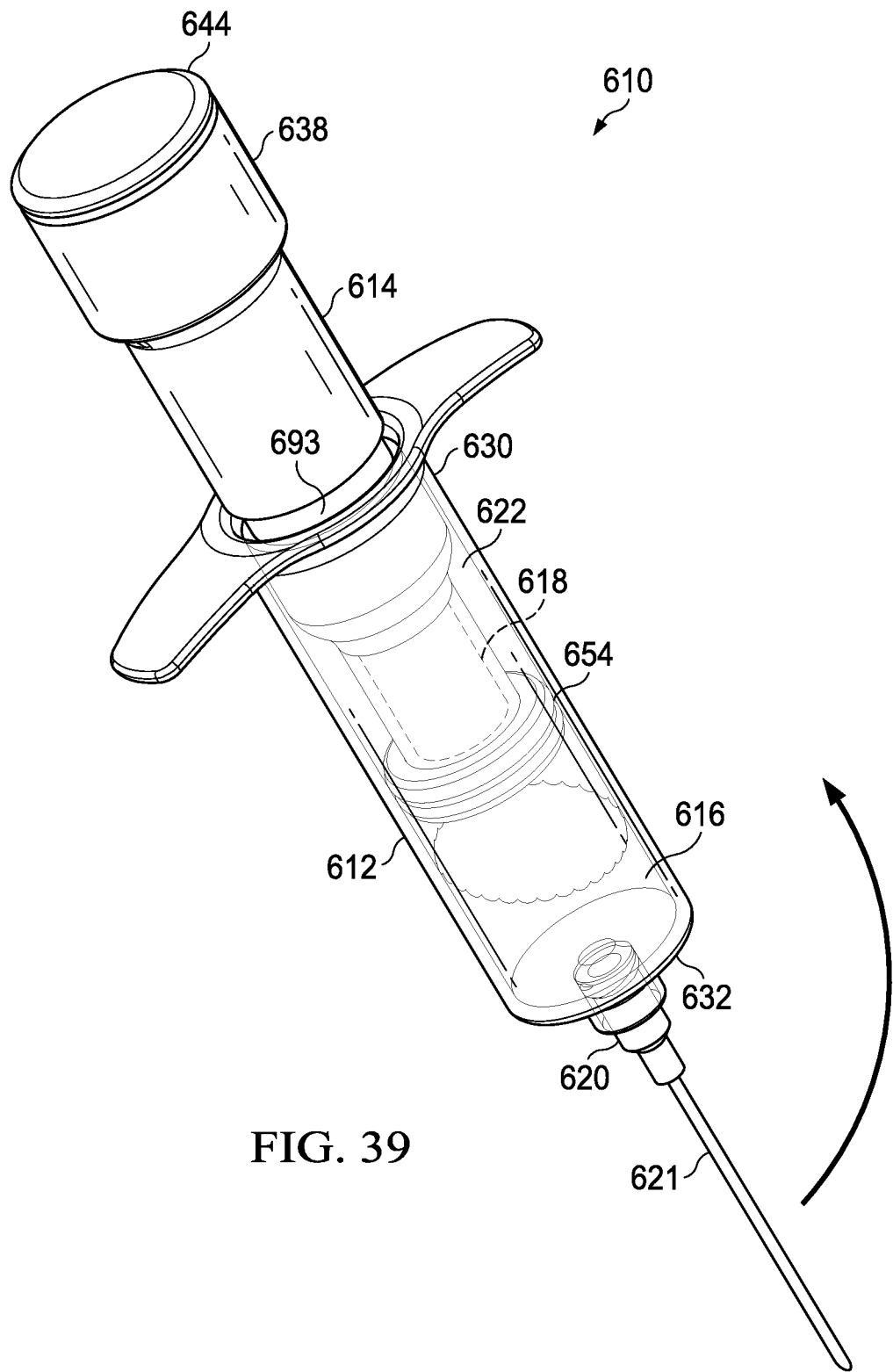
FIG. 39 depicts a side perspective view of the syringe syringe-based delivery device shown being rotated 180 degrees to an upright or vertical position.
Figure 40:
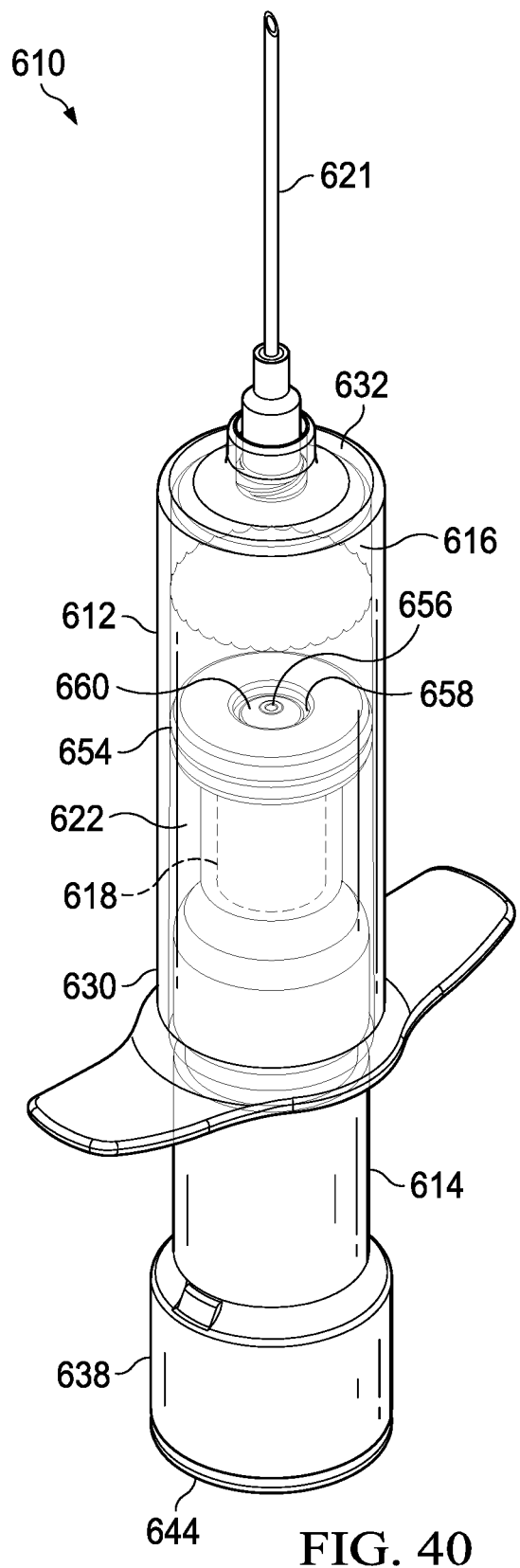
FIG. 40 depicts a side perspective view of the syringe syringe-based delivery device shown in the upright or vertical position.
Figure 41:
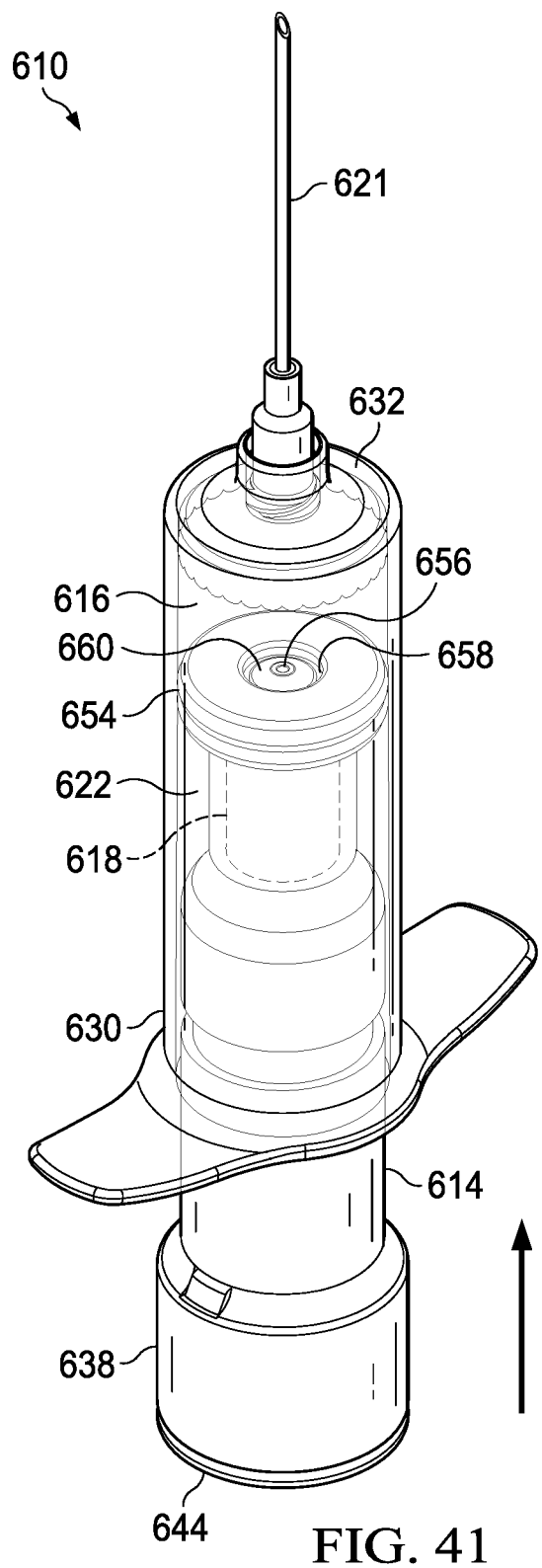
FIG. 41 depicts a side perspective view of the syringe syringe-based delivery device shown with the actuator mechanism advanced to purge air from the medicament chamber.
Figure 42:
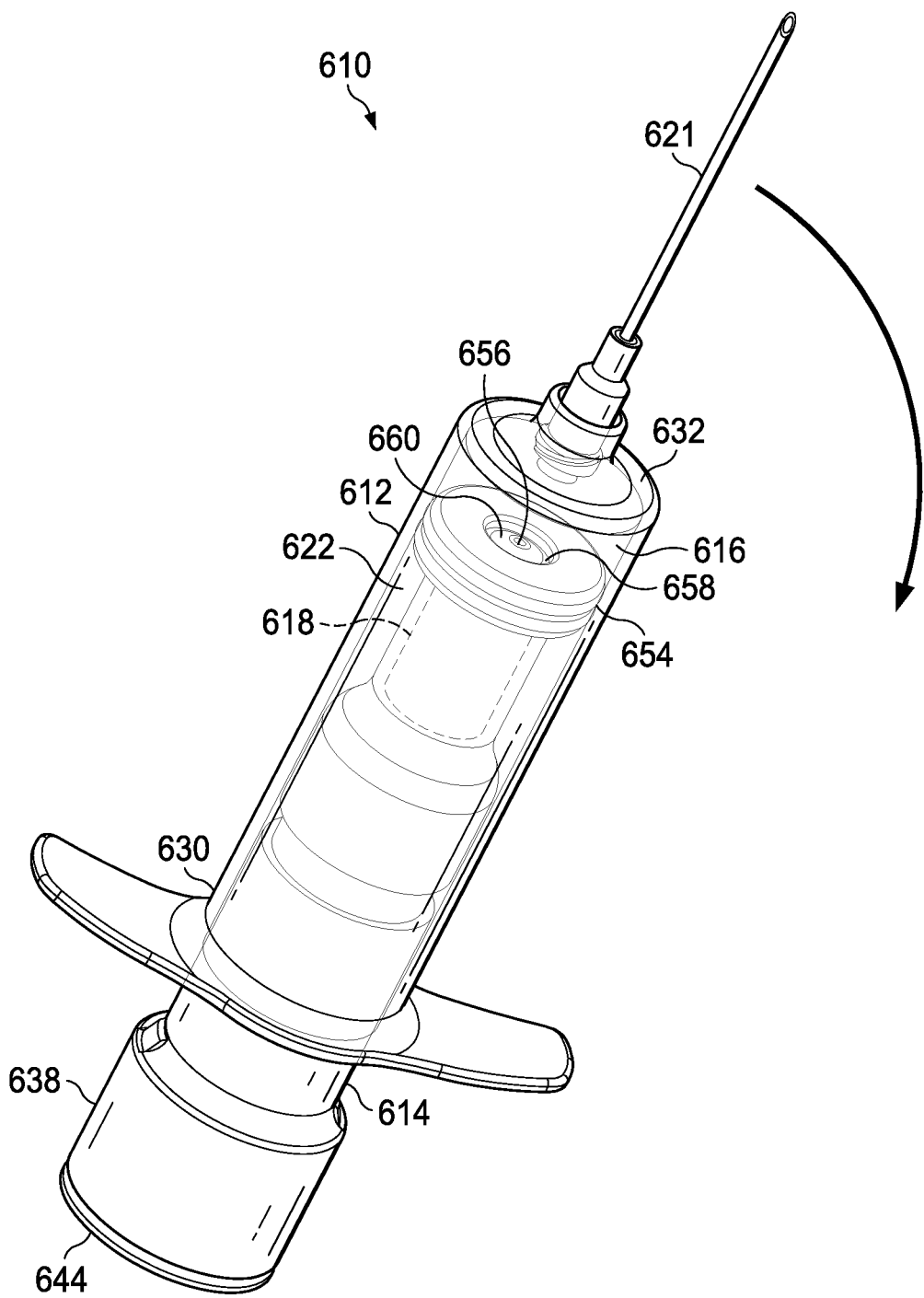
FIG. 42 depicts a side perspective view of the syringe syringe-based delivery device shown being rotated 180 degrees to a downward facing position.
Figure 43:
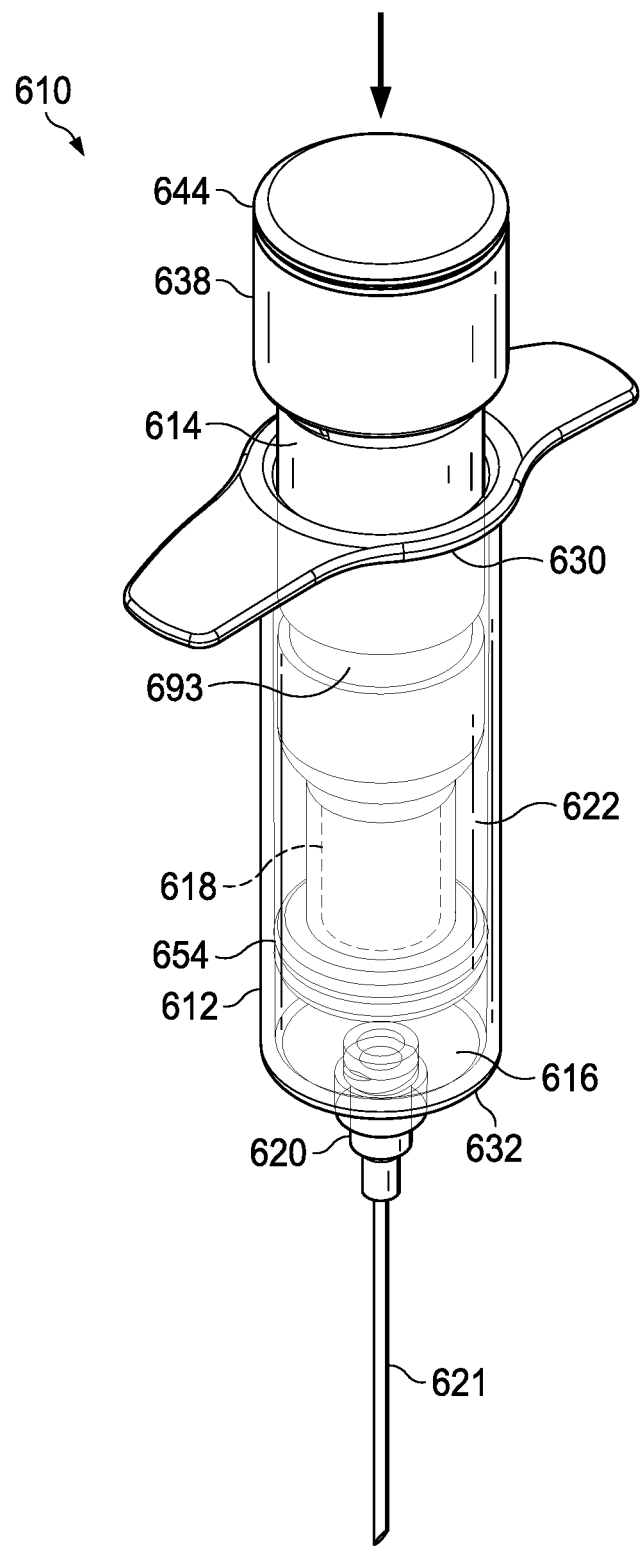
FIG. 43 depicts a side perspective view of the syringe syringe-based delivery device shown with the actuator mechanism advanced relative to the housing to expel the reconstituted fluid through the needle.
Figure 44:
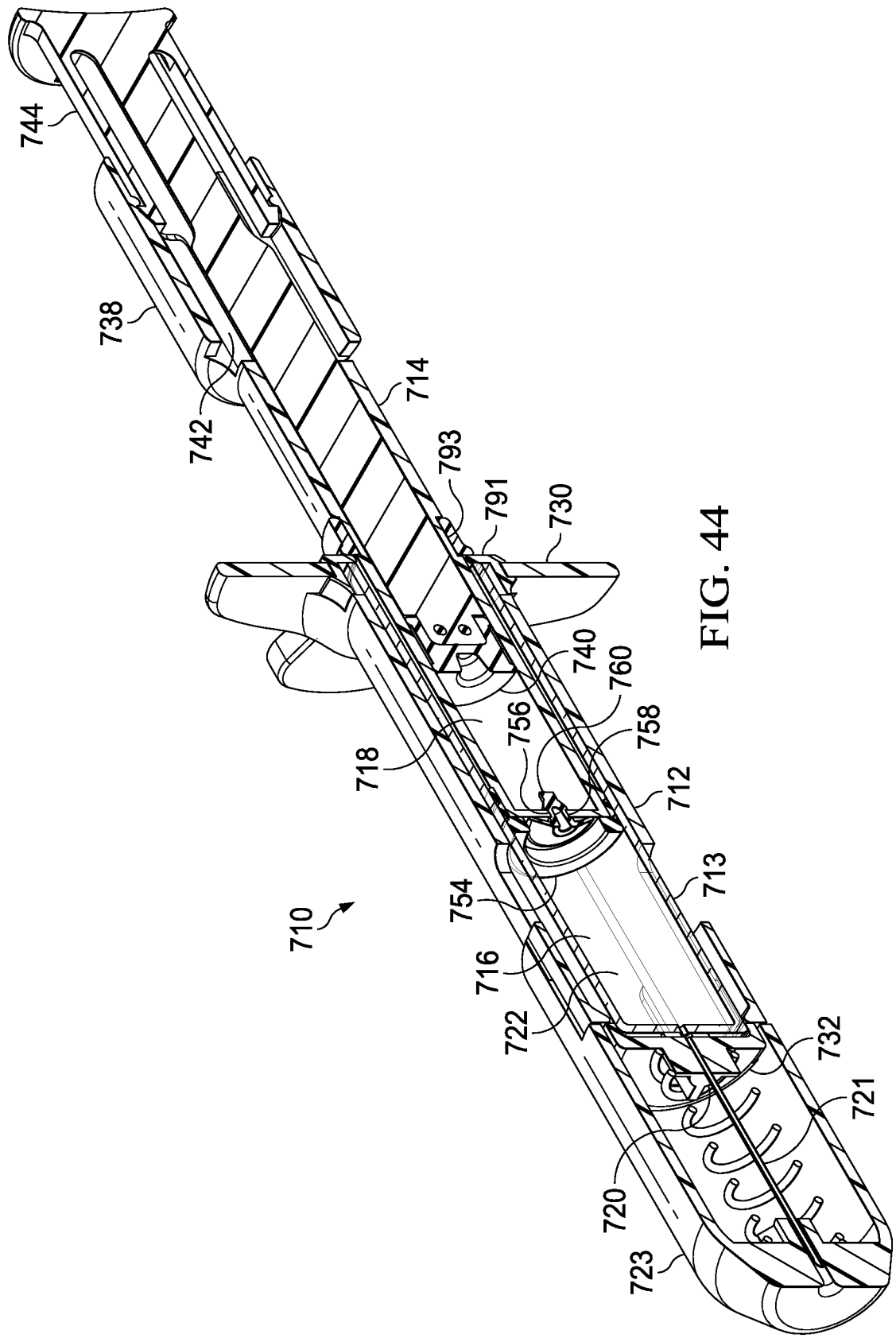
FIG. 44 depicts a side perspective view of a syringe syringe-based delivery device for reconstituted medications according to one embodiment.

As shown in FIG. 37, after the medicament has been reconstituted the removable clip 691 can be removed by the user to allow the actuator mechanism 614 to translate distally relative to the housing 612. Prior to administration, as shown in FIG. 38, the cover 623 can be removed from the needle 621 and, as shown in FIGS. 39 and 40, the syringe-based transfer device 610 can be rotated approximately 180 degrees. Once rotated to an upward facing position, as shown in FIG. 44, the actuator mechanism 614 can be depressed to purge air from within the medicament reservoir 616. As shown in FIG. 42 the syringe-based transfer device 610 can be rotated 180 degrees to a downward facing position. With the medicament reconstituted and the air purged the needle 621 can be inserted into a patient and, as shown in FIG. 43, the actuator mechanism 614 can be distally advanced to inject the reconstituted medicament into the patient. After use the syringe-based transfer device 610 can be disposed of in any suitable fashion.

FIGS. 44-53 illustrate a syringe-based transfer device 710 according to an embodiment. Dual syringe technology can allow for the faster reconstitution of powder medications that are administered, for example, intramuscularly or intravenously. In certain embodiments, an outer glass syringe can contain a powder form of a medication with a reconstitution solution located in a separate location in the syringe-based-transfer device. One use case for the syringe-based transfer device 710 can be for the reconstitution of ziprasidone HCl (sold under the trade name GEODON®), which is an antipsychotic used to treat schizophrenia and the manic symptoms of bipolar disorder. The syringe-based transfer device 610 can be used with glucagon to treat severe hypoglycemia in diabetic patients. The syringe-based transfer device 710 can be used with ceftriaxone (sold under the trade name ROCHEPIN®), a broad spectrum antibiotic used for a variety of medical conditions such as pneumonia, unitary track infections, sexually transmitted diseases, and in veterinary applications.

The syringe-based transfer device 710 (also referred to herein as "fluid transfer device," "glucagon delivery device," or "drug delivery device") includes a housing 712 and an actuator mechanism 714. The transfer device 710 can be configured to include or define a medicament reservoir 716 and a reconstitution fluid reservoir 718. The syringe-based transfer device 710 can be any suitable shape, size, or configuration. For example, while shown in FIG. 44 as being substantially cylindrical, the transfer device 710 can be square, rectangular, polygonal, and/or any other non-cylindrical shape.

As shown in FIG. 44, the housing 712 can include a proximal end portion 730 and a distal end portion 732 and a glass sleeve 713 that can define an inner volume 722 therebetween. In some embodiments, the housing 712 can be substantially similar to a syringe body. The proximal end portion 730 of the housing 712 can be substantially open at about the proximal end portion 732 and can be operably configured to accept the glass sleeve 713 or any other suitable container for compartment compatible with desirable medicaments. The proximal end portion 730 of the housing 712 can include a cap, snap, or other feature to retain the glass sleeve 713 after insertion. It will be appreciated that the sleeve can be glass, plastic, or any other material suitable or required for use with a particular drug or the like. In one embodiment, the sleeves can be interchangeable and can be selectively associated with the housing 713 for use with specific drugs or for specific applications. The sleeves can be secured relative to the housing 712 in any suitable fashion such as with a cap, a friction fit, a snap fit, or the like. In one embodiment, the glass sleeve 713 can be at least partially visible through the housing 712 such that a user can view the progress of reconstitution between the medicament and the reconstitution fluid in the medicament reservoir 716. The viewing window can have any suitable size and/or shape, can include any suitable feature to indicate that a medicament is fully reconstituted, can included graduation markings, coloration markings, or any other suitable feature.

The proximal end portion 730 can be configured to receive at least a portion of the actuator mechanism 714 such that at least a portion of the actuator mechanism 714 can be movably disposed within the inner volume 722 and the glass sleeve 713. Furthermore, the inner volume 722 can be configured to define the medicament reservoir 716, as further described herein. The distal end portion 732 of the housing 712 can include a port 720. In some embodiments, the port 720 can be monolithically formed with the housing 712. In other embodiments, the port 720 can be coupled to the distal end portion 732 in any suitable manner such as, for example, via a friction fit, a threaded coupling, a mechanical fastener, an adhesive, any number of mating recesses, and/or any combination thereof. The port 720 can be any suitable shape, size, or configuration. For example, in some embodiments, the port 720 is coupled with the glass sleeve 713, which can be fluidically coupled with a needle 721. In the illustrated embodiment, the needle 721 can be associated with a spring loaded cover 723 that covers the needle 721 in a pre-use configuration to help prevent accidental needlesticks.

The actuator mechanism 714 can be disposed within the inner volume 722 and the glass sleeve 713 and can be movable between a first position (e.g., a proximal position relative to the housing 612) and a second position (e.g., a distal position relative to the housing 612). The movement of the actuator mechanism 714 relative to the housing 712 can move the transfer device 710 between a number of different configurations and positions, as further described herein. The actuator mechanism 714 can include a plunger 744 and a syringe body 738 that can define an inner volume 742 therebetween. At least a portion of the inner volume 742 can be configured to define the reconstitution fluid reservoir 718, as further described herein. The plunger 744 can include a plunger seal 740 that can fluidically seal the reconstitution fluid reservoir 718. The syringe body 738 can include an open proximal end such that the plunger 744 can be movably disposed within the inner volume 742.

The actuator mechanism 714 can include a plunger seal 754 that can form a friction fit with the inner surface of the walls defining the inner volume 722 when the actuator mechanism 714 is disposed within the housing 712. Similarly stated, the plunger seal 754 can define a fluidic seal with the inner surface of the walls defining the inner volume 722 such that a portion of the inner volume 722 distal of the plunger seal 754 is fluidically isolated from a portion of the inner volume 722 proximal of the plunger seal 754. The plunger seal 754 can define a channel 756 that that can extend through a distal end and a proximal end of the plunger seal 754. A portion of an inner set of walls defining the channel 756 can accept a valve seat 758. In this manner, a portion of the channel 756 can receive a valve 760 that can be in contact with the valve seat 758.

The valve 760 can be any suitable valve. For example, in some embodiments, the valve 760 can be a one-way check valve to allow a flow of a fluid, such as 1.2 ml of sterile water, from a proximal end of the valve 760 to a distal end of the valve 760, but substantially not allow a flow of the fluid from the distal end to the proximal end. The valve 760 can be disposed within the channel 756 and can be in contact with the valve seat 758 such that the valve 760 forms a substantially fluid tight seal with the walls defining the channel 756. In some embodiments, the valve 760 can form a friction fit with walls defining the channel 756. In other embodiments, the valve 760 can form a threaded coupling or the like with at least a portion of the walls. The valve 760 can also include a seal member configured to engage the valve seat 758 to form at least a portion of the fluid tight seal.

As described above, the plunger 744 can be movably disposed within the syringe body 738. More specifically, the plunger 744 can be movable between a first configuration (e.g., a proximal position) and a second configuration (e.g., a distal position) to create positive pressure to urge for example, from about 1 ml to about 2 ml of sterile water, out of the reconstitution fluid reservoir 718. In this manner, the distal translation of the plunger 744 can first cause the plunger 744 to move distally to expel the fluid from the reconstitution fluid reservoir 718. Once the reconstitution reservoir 718 has been emptied into the medicament reservoir 716 the fluid can combine with a medicament, such as glucagon. Continued distal movement of the plunger 744 can continue until a proximal end of the plunger 744 abuts the proximal end portion 730 of the syringe body 738. In one embodiment the plunger 744, when fully depressed, can be fixedly coupled with the syringe body 738 using any suitable locking mechanism such as a snap feature. The actuator mechanism 714 can be prevented from moving distally relative to the housing 712 by a removable clip 791 retained in a channel 793. The removable clip 791 can be sized such that the removable clip 791 abuts the proximal end portion 730 of the housing 712, where removal of the removable clip 791 can allow the actuator mechanism to translate distally within the housing 712.

Figure 45:
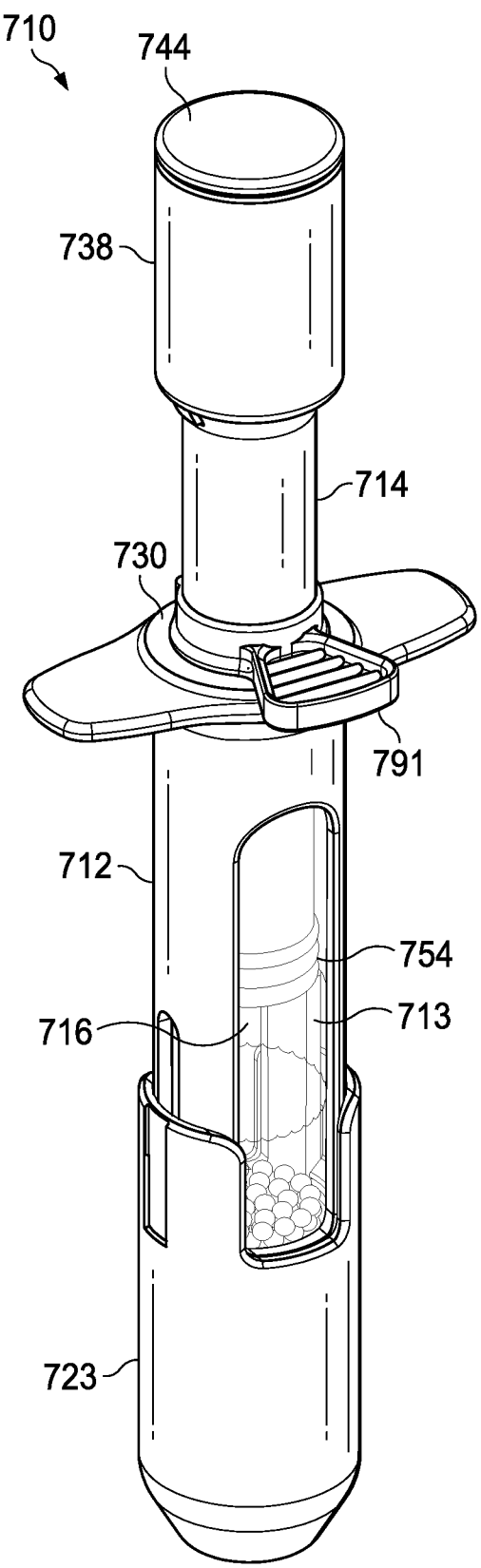
FIG. 45 depicts a side perspective view of the syringe syringe-based delivery device shown with a plunger depressed to expel a reconstitution fluid into a medicament chamber according to one embodiment.
Figure 46:
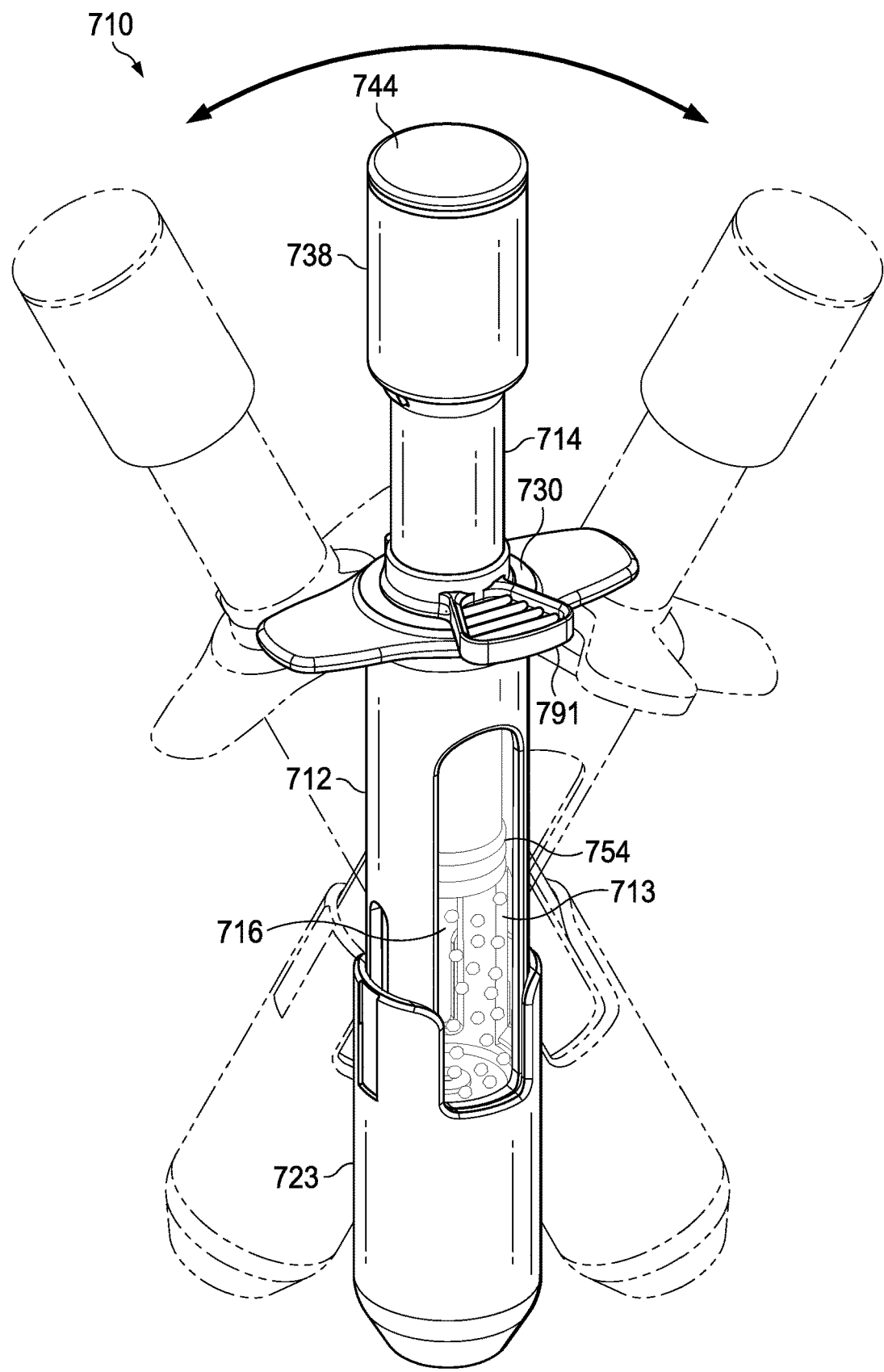
FIG. 46 depicts a side perspective view of the syringe syringe-based delivery device shown being agitated to mix the reconstitution fluid with the medicament.
Figure 47:
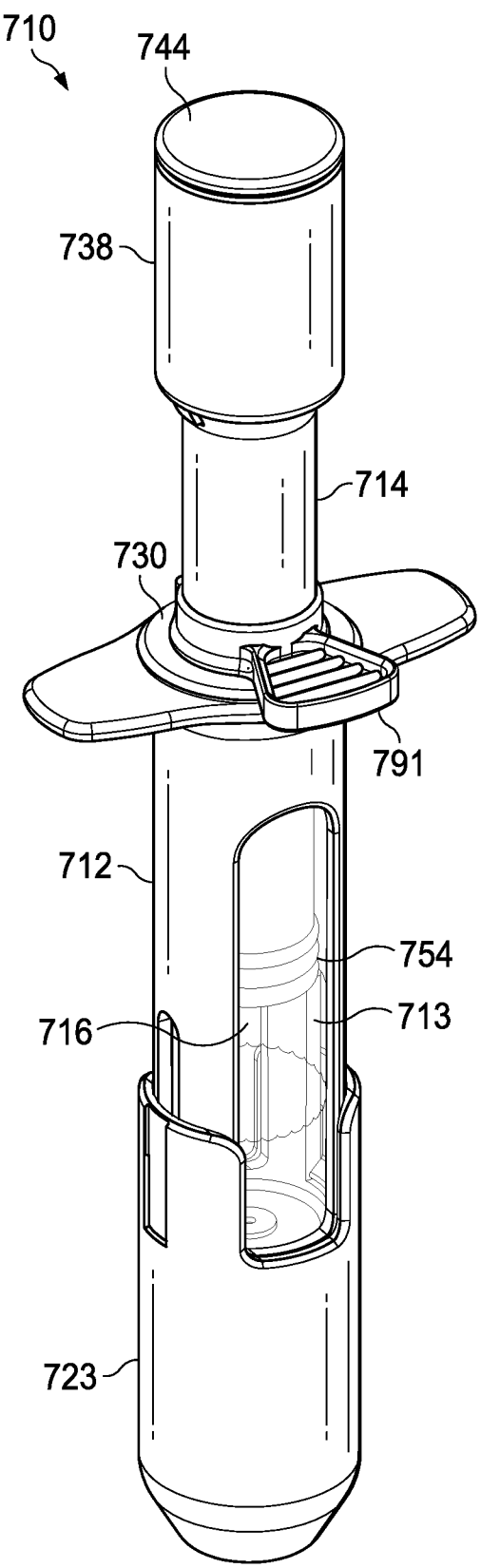
FIG. 47 depicts a side perspective view of the syringe syringe-based delivery device shown with a fully reconstituted medication retained within the medicament chamber.

In use, as shown in FIG. 45, a user can depress the plunger 744 to urge an amount of fluid, such as 1.2 ml of sterile water, from the reconstitution fluid reservoir 718 into the medicament reservoir 716. Once the fluid, water, saline, or any suitable reconstitution fluid has been combined in the medicament reservoir 716 the syringe-based transfer device 710 can be agitated as illustrated in FIG. 46. The syringe-based transfer device 710 can be shaken for a period of time, such as 30 seconds to 120 seconds, until the reconstitution fluid has combined with the medicament to form a substantially homogenous fluid. In one embodiment, the sterile water is combined with glucagon and is agitated manually until the medicament is fully dissolved and reconstituted as illustrated in FIG. 47.

Figure 48:
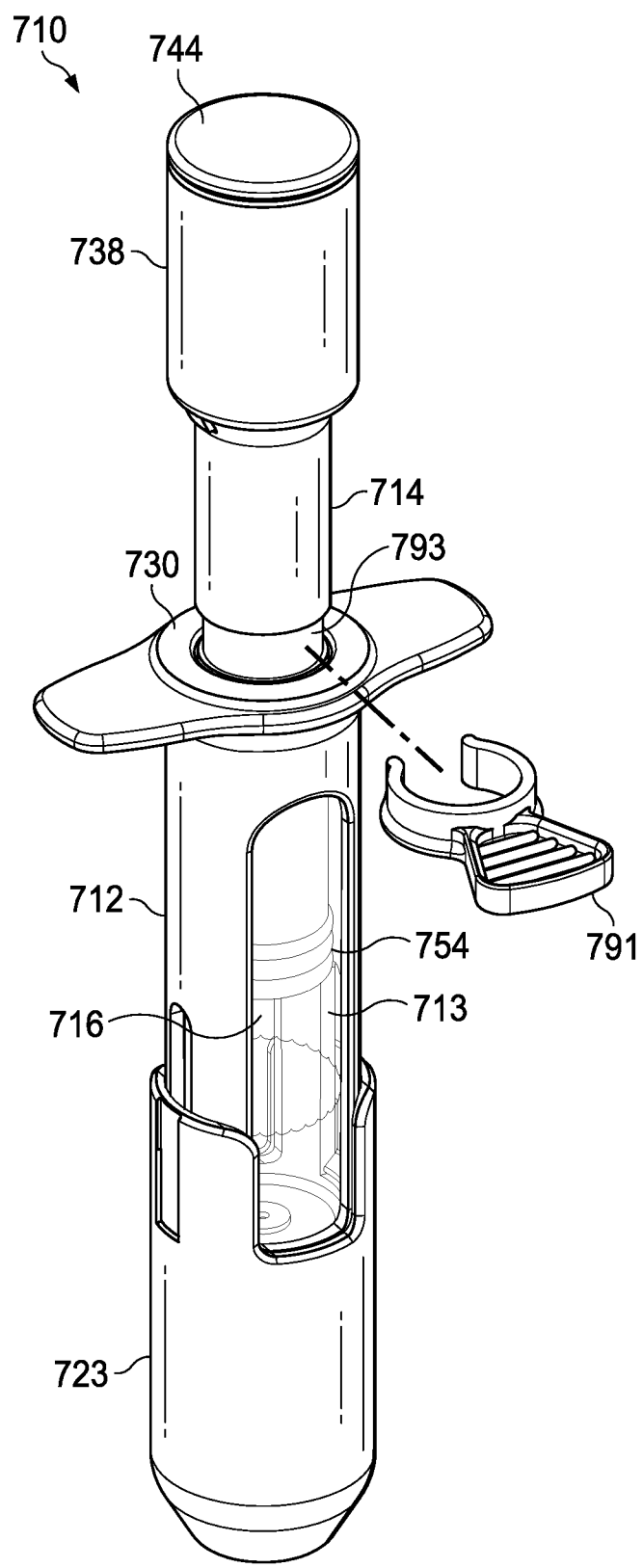
FIG. 48 depicts a side perspective view of the syringe syringe-based delivery device shown with a clip being removed from an actuator mechanism such that the actuator mechanism is distally moveable relative to the housing.
Figure 49:
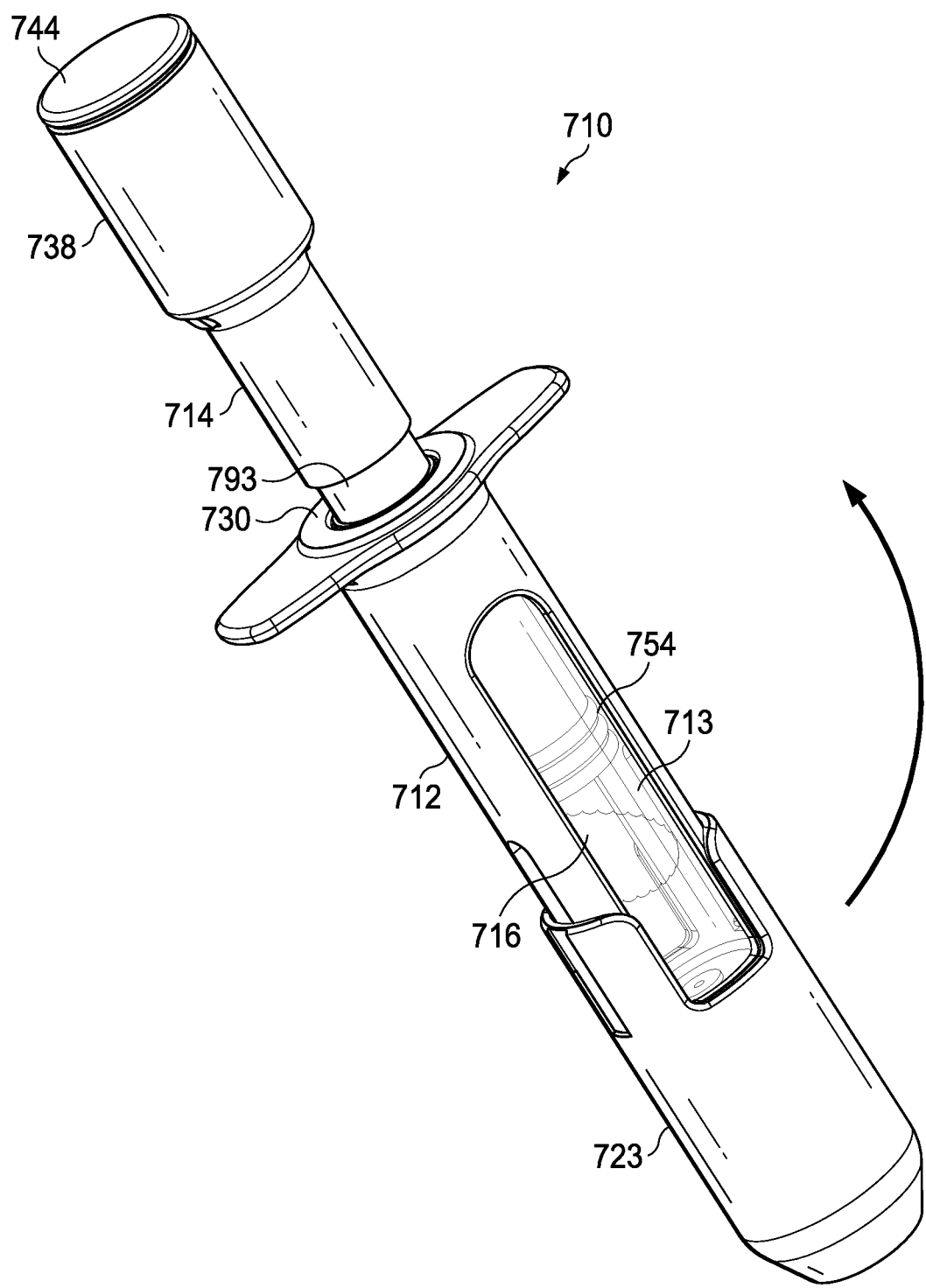
FIG. 49 depicts a side perspective view of the syringe syringe-based delivery device shown being rotated 180 degrees to an upright or vertical position.
Figure 50:
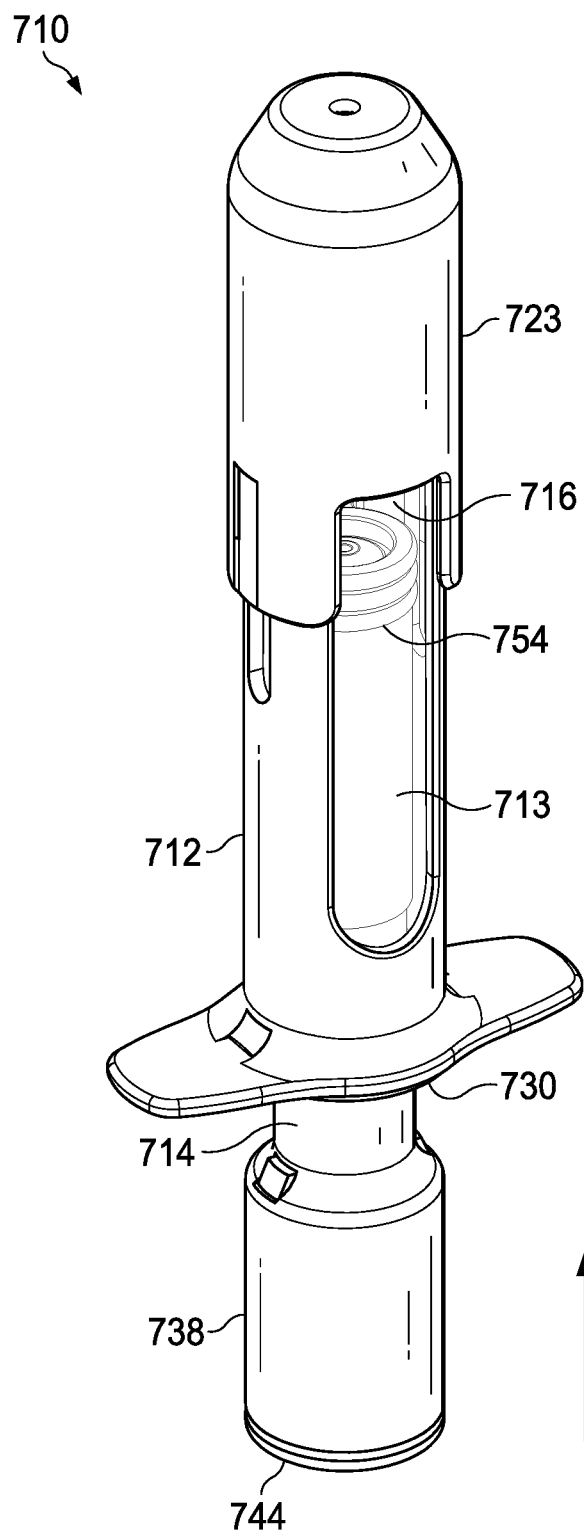
FIG. 50 depicts a side perspective view of the syringe syringe-based delivery device shown in the upright or vertical position with the actuator mechanism advanced to purge air from the medicament chamber.
Figure 51:
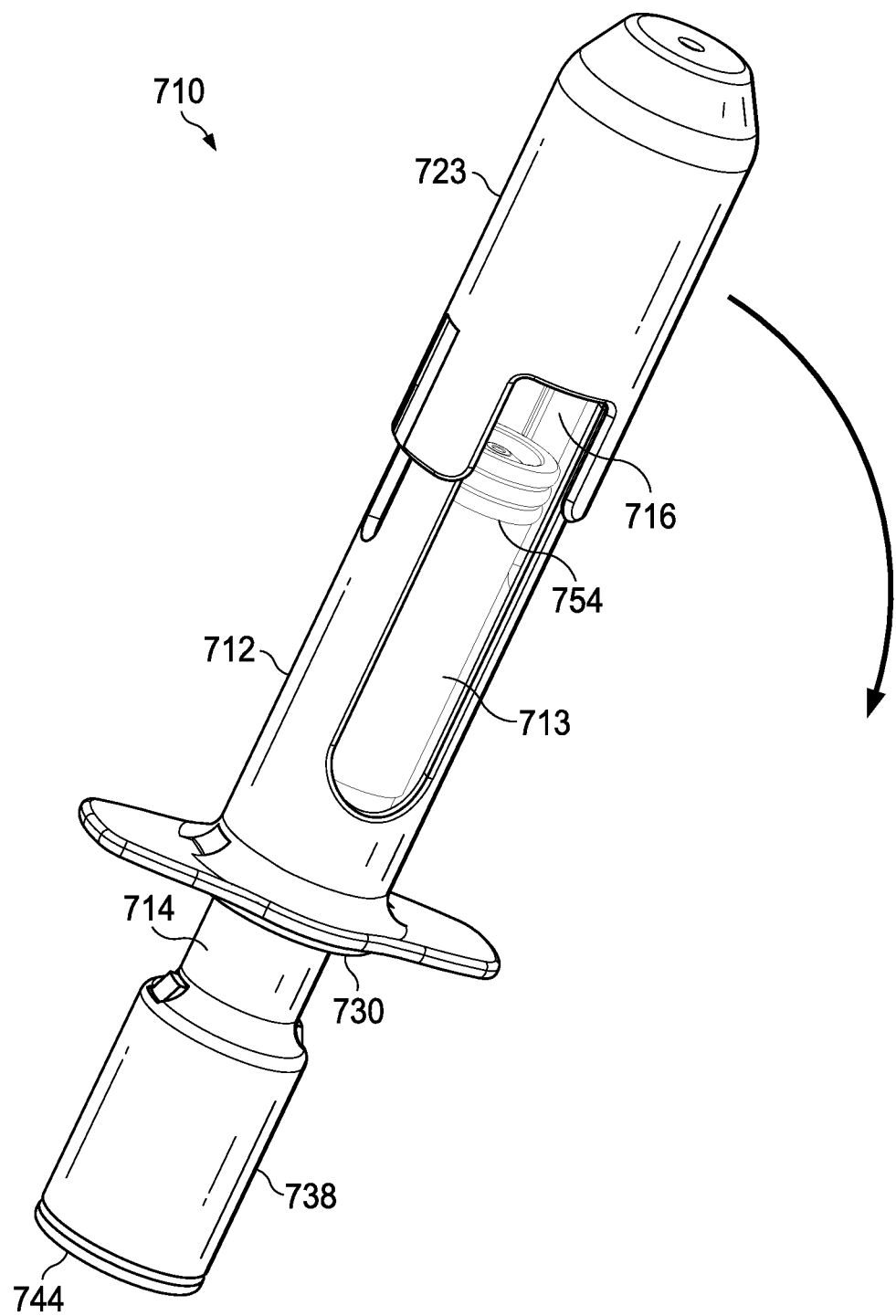
FIG. 51 depicts a side perspective view of the syringe syringe-based delivery device shown being rotated 180 degrees to a downward facing position.
Figure 52:
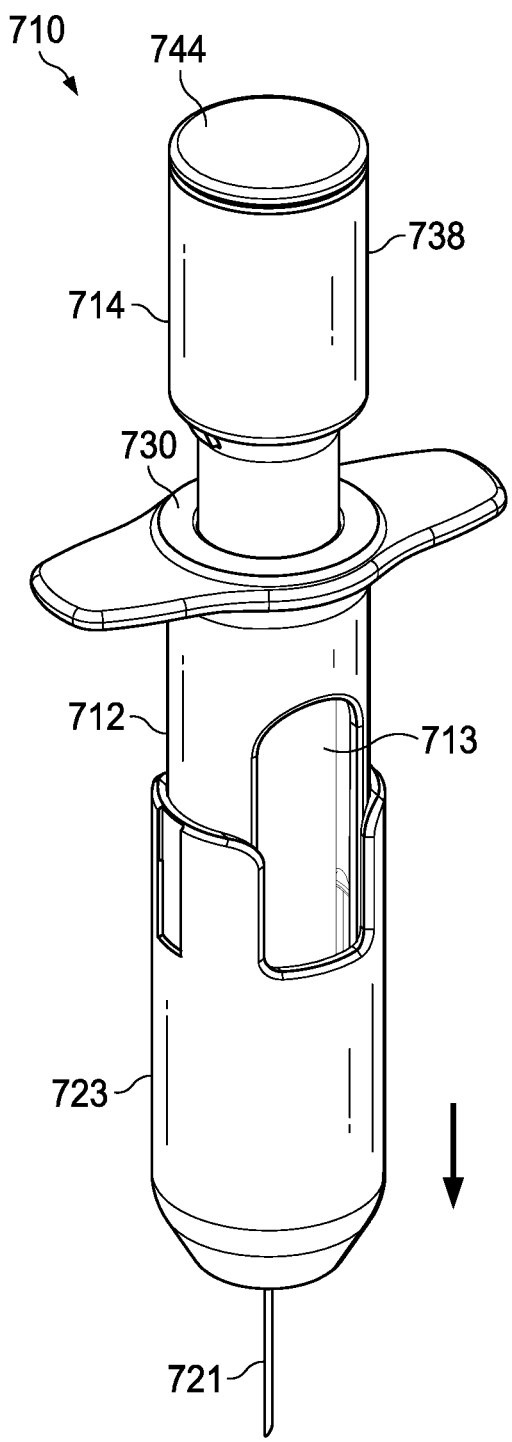
FIG. 52 depicts a side perspective view of the syringe syringe-based delivery device shown advanced into a patient to retract a spring loaded needle guard to expose a needle.
Figure 53:
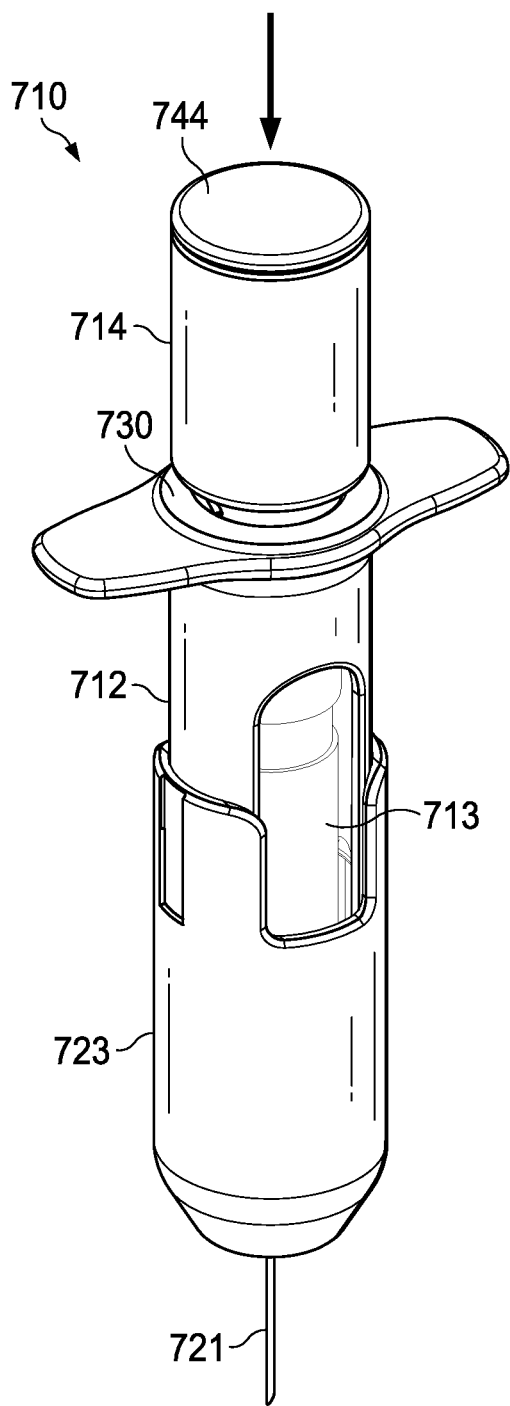
FIG. 53 depicts a side perspective view of the syringe syringe-based delivery device shown with the actuator mechanism advanced relative to the housing to expel the reconstituted fluid through the needle.

As shown in FIG. 48, after the medicament has been reconstituted the removable clip 791 can be removed by the user to allow the actuator mechanism 714 to translate distally relative to the housing 712. Prior to administration, as shown in FIG. 49, the syringe-based transfer device 710 can be rotated approximately 180 degrees. Once rotated to an upward facing position, as shown in FIG. 50, the actuator mechanism 714 can be depressed to purge air from within the medicament reservoir 716. As shown in FIG. 50, the actuator mechanism 714 can be depressed a predetermined distance, such as to a threshold line, to purge all air from the medicament reservoir 716. As illustrated in FIG. 51, the syringe-based transfer device 710 can be rotated 180 degrees to a downward facing position. With the medicament reconstituted and the air purged, as shown in FIG. 52, the spring-loaded cover 723 can retract as the needle 721 is inserted into a patient. Once the needle 721 has been positioned within the patient the actuator mechanism 714 can be distally advanced, as shown in FIG. 53, to inject the reconstituted medicament into the patient. After use the syringe-based transfer device 710 can be disposed of in any suitable fashion.

Figure 54:
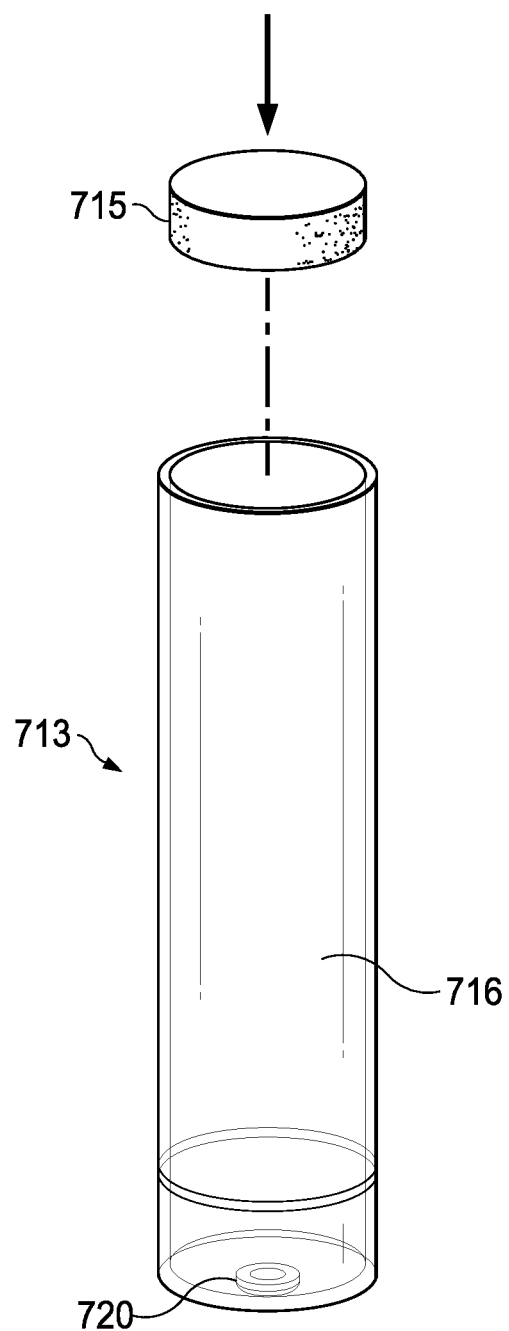
FIG. 54 depicts a side perspective view of a sleeve associated with a medicament in solid form according to one embodiment.
Figure 55:
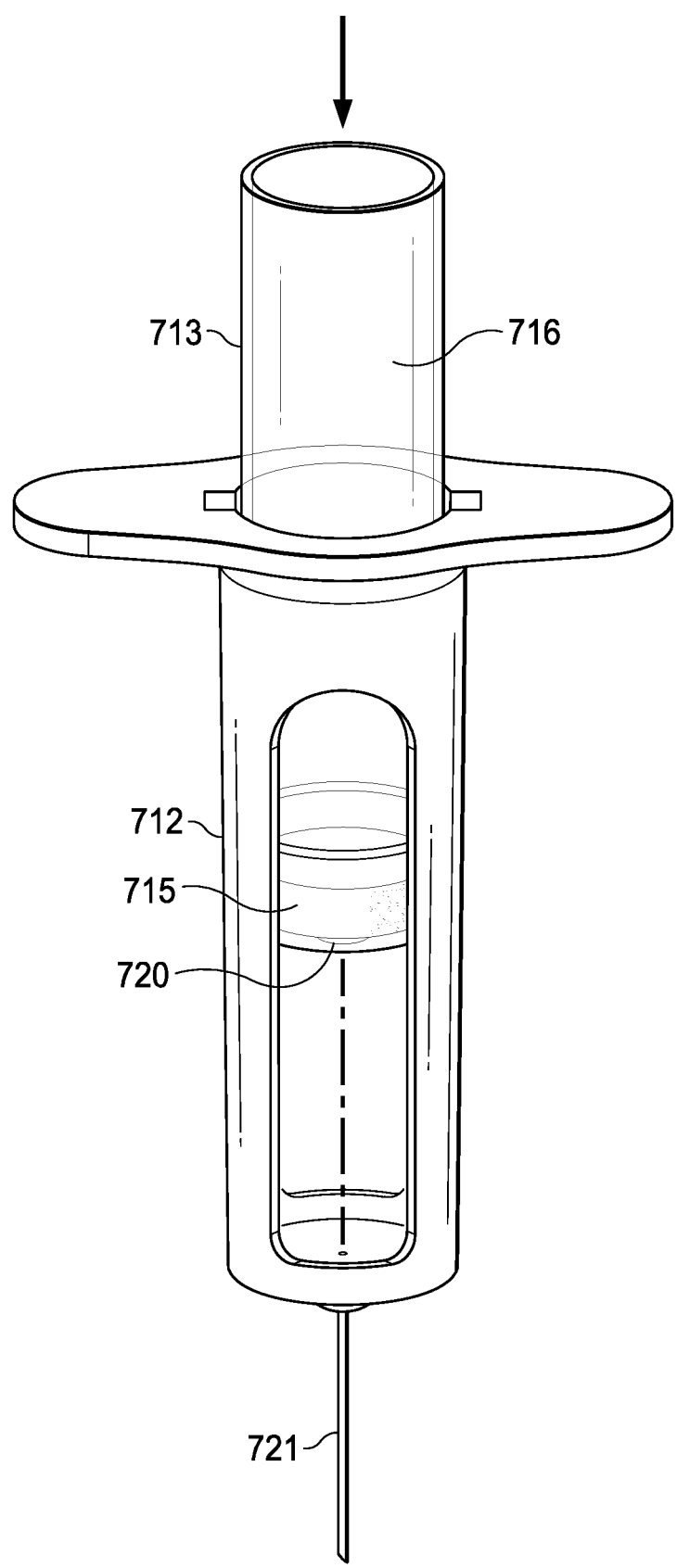
FIG. 55 depicts a side perspective view of the sleeve shown in FIG. 54 being engaged with a housing having a needle.
Figure 56:
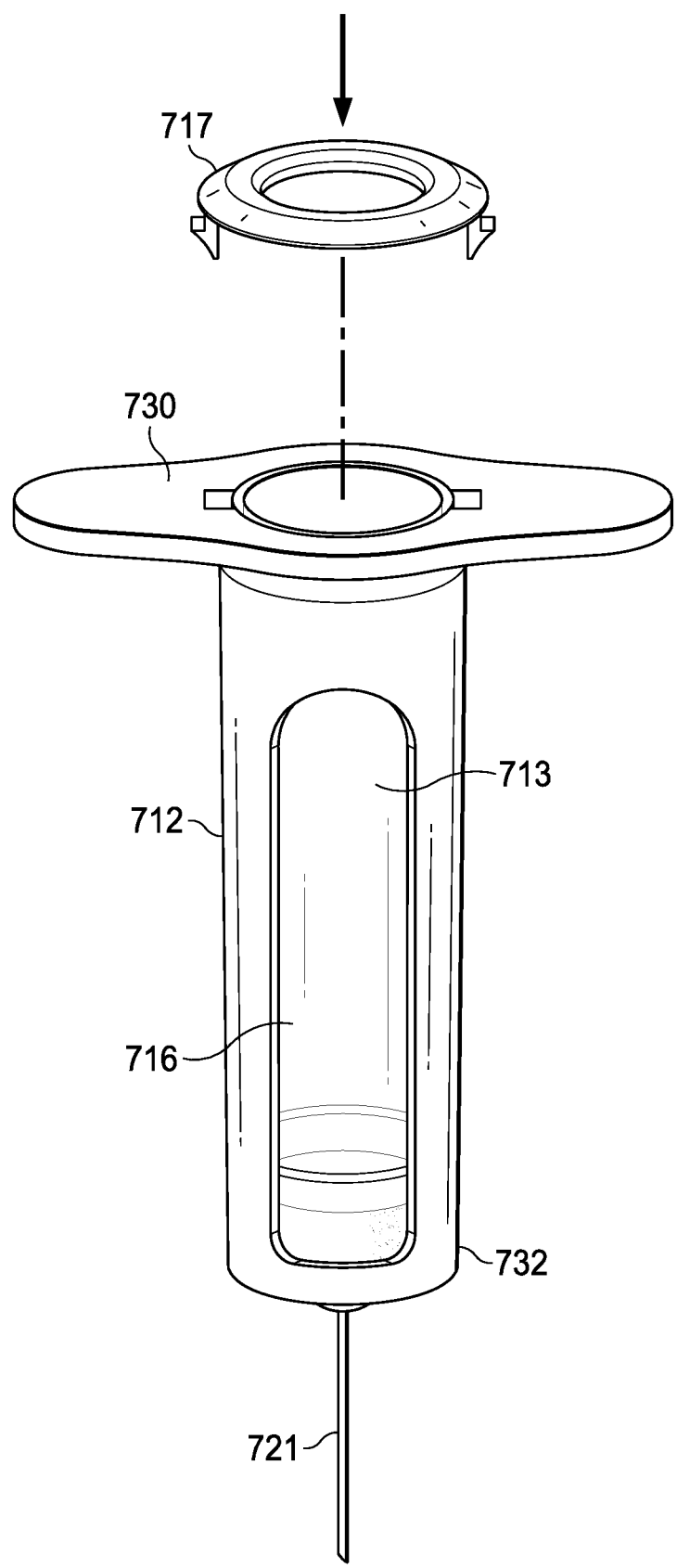
FIG. 56 depicts a side perspective view of the holder and sleeve shown in FIG. 55 secured with a cap.

FIG. 54 illustrates a more detailed side view of the glass sleeve 713. The glass sleeve 713 can be sized to fixedly engage with a housing, such as housing 712, for use with medications or the like that require certain contain types. Any suitable sleeve is contemplated from any suitable material where, for example, the opaqueness or transparency of the sleeve can vary based upon need. For example, some cancer drugs are light sensitive and an opaque sleeve may be used for such applications. The sleeve 713 can include a valve or port 720 and can have an open proximal end. As illustrated in FIG. 54, a medicament 715 in powdered or tablet form, for example, can be inserted into the glass sleeve 713. As illustrated in FIG. 55, the glass sleeve 713 can be coupled with the housing 712 and, as shown in FIG. 56 a cap 717 can be seated in the proximal end portion 730 of the housing 712 to fixedly retain the glass sleeve 713.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. For example, the removable clip 691 illustrated with respect to the syringe-based transfer device 610 can be used in combination with various embodiments described herein. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

I claim:

1. A syringe-based apparatus for delivering fluid comprising:
   (a) a housing, the housing having an open proximal end and a distal end defining an inner volume;
   (b) a needle coupled with the distal end of the housing;
   (c) a sleeve having a proximal end and a distal end, the sleeve being insertable into the open proximal end of the housing into the inner volume of the housing, wherein the sleeve comprises a port at the distal end of the sleeve;
   (d) an actuator mechanism, the actuator mechanism being coupled with the housing, the actuator mechanism comprising a syringe body and a plunger;
   (e) a medicament reservoir, the medicament reservoir being defined at least partially by the sleeve positioned within the housing and the actuator mechanism, wherein the medicament reservoir retains an amount of a medicament in solid form; and
   (f) a reconstitution fluid reservoir operably configured to retain a fluid, the reconstitution fluid reservoir being defined at least partially by the syringe body and the plunger of the actuator mechanism;
   wherein the plunger is moveable relative to the syringe body to expel the fluid from the reconstitution fluid reservoir into the medicament reservoir such that the fluid and the amount of the medicament form a reconstituted medication, and wherein the plunger extends into the sleeve through the proximal end of the sleeve;
   wherein the actuator mechanism is moveable relative to the housing to expel the reconstituted medication from the medicament reservoir through the needle.

2. The apparatus of claim 1, wherein the reconstitution fluid reservoir retains from about 1 ml to about 2 ml of sterile water or saline.

3. The apparatus of claim 1, wherein reconstitution fluid reservoir retains from about 1 ml to about 2 ml of lidocaine.

4. The apparatus of claim 1, wherein the medicament reservoir retains an amount of glucagon.

5. The apparatus of claim 1, wherein the medicament reservoir retains an amount of ziprasidone HCl.

6. The apparatus of claim 1, further comprising a spring-loaded needle guard movably coupled with the housing.

7. The apparatus of claim 1, wherein the housing defines a viewing window such that the medicament is visible within the sleeve.

8. The apparatus of claim 1, wherein the plunger is fixedly engaged with the syringe body by a locking mechanism when actuated distally.

9. The apparatus of claim 1, wherein, when the plunger is moved relative to the syringe body to expel an amount of the fluid from the reconstitution fluid reservoir into the medicament reservoir such that the amount of the fluid and the medicament form a reconstituted medication, a distal end of the plunger moves to abut a proximal end of the syringe body.

10. A syringe-based apparatus for delivering fluid comprising:
    (a) a housing, the housing having an open proximal end and a distal end defining an inner volume, wherein the housing defines a viewing window;
    (b) a needle coupled with the distal end of the housing;
    (c) a glass sleeve having a proximal end and a distal end, the glass sleeve being insertable into the open proximal end of the housing into the inner volume of the housing, wherein the glass sleeve comprises a valve at the distal end of the glass sleeve;
    (d) an actuator mechanism, the actuator mechanism being coupled with the housing, the actuator mechanism comprising a syringe body and a plunger, the plunger extending into the sleeve through the proximal end;
    (e) a locking mechanism, wherein the locking mechanism is operably configured to fixedly couple the plunger and the syringe body when the plunger is urged distally;
    (f) a medicament reservoir, the medicament reservoir being defined at least partially by the glass sleeve positioned within the housing and the actuator mechanism, wherein the medicament reservoir retains an amount of a medicament selected from the group consisting of glucagon, ziprasidone HCl, and ceftriaxone; and
    (g) a reconstitution fluid reservoir retaining an amount of a fluid selected from the group consisting of sterile water, saline, and lidocaine, the reconstitution fluid reservoir being defined at least partially by the syringe body and the plunger of the actuator mechanism;
    wherein the plunger is moveable relative to the syringe body to expel the amount of the fluid from the reconstitution fluid reservoir into the medicament reservoir such that the amount of the fluid and the amount of the medicament form a reconstituted medication;
    wherein the actuator mechanism is moveable relative to the housing to expel the reconstituted medication from the medicament reservoir through the needle.

11. The apparatus of claim 10, wherein the reconstitution fluid reservoir retains from about 1 ml to about 2 ml of sterile water or saline.

12. The apparatus of claim 10, wherein the reconstitution fluid reservoir retains from about 1 ml to about 2 ml of lidocaine.

13. The apparatus of claim 10, wherein the medicament reservoir retains an amount of glucagon.

14. The apparatus of claim 10, wherein the medicament reservoir retains an amount of ziprasidone HCl.

15. The apparatus of claim 10, further comprising a spring-loaded needle guard movably coupled with the housing.

16. The apparatus of claim 10, wherein the medicament is visible within the medicament reservoir through the viewing window.

17. The apparatus of claim 10, wherein the plunger is fixedly engaged with the syringe body by a locking mechanism when actuated distally.

18. The apparatus of claim 10, wherein the amount of the fluid is from about 1 ml to about 2 ml of fluid.

* * * * *